United States Patent
Devary et al.

(10) Patent No.: US 10,933,117 B2
(45) Date of Patent: Mar. 2, 2021

(54) ENDOPLASMIC RETICULUM STRESS AS A PREDICTIVE TOOL IN CANCER THERAPY AND A COMBINATION THERAPY FOR THE TREATMENT OF CANCER

(71) Applicant: IMMUNE SYSTEM KEY LTD., Jerusalem (IL)

(72) Inventors: Yoram Devary, Jerusalem (IL); Uziel Sandler, Jerusalem (IL)

(73) Assignee: IMMUNE SYSTEM KEY LTD., Jerusalem (IL)

( * ) Notice: Subject to any disclaimer, the term of this patent is extended or adjusted under 35 U.S.C. 154(b) by 114 days.

(21) Appl. No.: 16/050,255

(22) Filed: Jul. 31, 2018

(65) Prior Publication Data
US 2018/0333452 A1 Nov. 22, 2018

Related U.S. Application Data

(63) Continuation-in-part of application No. PCT/IL2017/050129, filed on Feb. 2, 2017.

(60) Provisional application No. 62/291,190, filed on Feb. 4, 2016.

(51) Int. Cl.
*A61K 38/10* (2006.01)
*A61P 35/00* (2006.01)
*A61K 31/337* (2006.01)
*G01N 33/53* (2006.01)
*C12Q 1/6886* (2018.01)
*G01N 33/574* (2006.01)
*A61K 38/17* (2006.01)
*A61K 45/06* (2006.01)
*A61K 31/704* (2006.01)
*A61K 39/395* (2006.01)

(52) U.S. Cl.
CPC ............ *A61K 38/10* (2013.01); *A61K 31/337* (2013.01); *A61K 31/704* (2013.01); *A61K 38/1709* (2013.01); *A61K 39/39558* (2013.01); *A61K 45/06* (2013.01); *A61P 35/00* (2018.01); *C12Q 1/6886* (2013.01); *G01N 33/53* (2013.01); *G01N 33/574* (2013.01); *G01N 33/57496* (2013.01); *C12Q 2600/106* (2013.01); *C12Q 2600/158* (2013.01); *G01N 2800/52* (2013.01)

(58) Field of Classification Search
CPC .............................. A61K 38/10; A61P 35/00
USPC ....................................................... 424/173.1
See application file for complete search history.

(56) References Cited

U.S. PATENT DOCUMENTS

| | | | |
|---|---|---|---|
| 9,878,015 B2* | 1/2018 | Devary | ................... A61P 35/04 |
| 2009/0018060 A1* | 1/2009 | Devary | ................... A61P 31/04 |
| | | | 514/6.9 |
| 2009/0181472 A1 | 7/2009 | Cheng et al. | |

FOREIGN PATENT DOCUMENTS

| | | |
|---|---|---|
| CN | 102375061 A | 3/2012 |
| WO | 02/077176 A2 | 10/2002 |
| WO | 02/082076 A2 | 10/2002 |
| WO | 2006/046239 A2 | 5/2006 |
| WO | 2007/091240 A2 | 8/2007 |
| WO | 2007/122622 A1 | 11/2007 |
| WO | 2008/042508 A1 | 4/2008 |
| WO | 2008/075349 A1 | 6/2008 |
| WO | 2015/083167 A1 | 6/2015 |

OTHER PUBLICATIONS

Eisenhauer et al., "New response evaluation criteria in solid tumours: Revised RECIST guideline", European Journal of Cancer, vol. 45, pp. 228-247, (2009).

(Continued)

*Primary Examiner* — Yan Xiao
(74) *Attorney, Agent, or Firm* — Vorys, Sater, Seymour and Pease LLP; Anthony P. Venturino

(57) ABSTRACT

Provided are methods, agents and kits for use in assessing the effect of treatment on cancer patients. Further provided is a combination therapy for reducing the administered standard of care doses of anti-cancer agents in treated cancer patients.

8 Claims, 16 Drawing Sheets

Specification includes a Sequence Listing.

(56) References Cited

OTHER PUBLICATIONS

Han et al., "Inhibition of endoplasmic reticulum chaperone protein glucose-regulated protein 78 potentiates anti-angiogenic therapy in renal cell carcinoma through inactivation of the PERK/eIF2alpha pathway", Oncotarget, vol. 6, No. 33, pp. 34818-34830, (2015).

Lee et al., "GRP78 as a Novel Predictor of Responsiveness to Chemotherapy in Breast Cancer", Cancer Res, vol. 66, No. 16, pp. 7849-7853, (2006).

Lee et al., "GRP78 Induction in Cancer: Therapeutic and Prognostic Implications", Cancer Res, vol. 67, No. 8, pp. 3496-3499, (2007).

Lee et al., "GRP78 as potential predictor for breast cancer response to adjuvant taxane therapy", Int. J. Cancer, vol. 128, pp. 726-731, (2011).

Mehta et al., "Predictive and prognostic molecular markers for cancer medicine", Ther Adv Med Oncol, vol. 2, No. 2, pp. 125-148, (2010).

Sandler et al., "NEROFE—A novel human hormone-peptide with anti-cancer activity", Journal of Experimental Therapeutics and Oncology, vol. 8, pp. 327-339, (2010).

Sandler et al., "A Novel Human Hormone-peptide NEROFE with Strong anti Cancer Activity", Recent Advances in Clinical Medicine, ISSN: 1790-5125, pp. 156-161, (2010).

Sato et al., "GRP78 Signaling Hub: A Receptor for Targeted Tumor Therapy", Advances in Genetics, vol. 69, pp. 98-114, (2010).

Zheng et al., "The endoplasmic reticulum stress markers GRP78 and CHOP predict disease-free survival and responsiveness to chemotherapy in breast cancer", Breast Cancer Res Treat, vol. 145, pp. 349-358, (2014).

Anonymous: "Doxorubicin Dosage Guide with Precautions—Drugs.com", Mar. 24, 2020 (Mar. 24, 2020).

\* cited by examiner

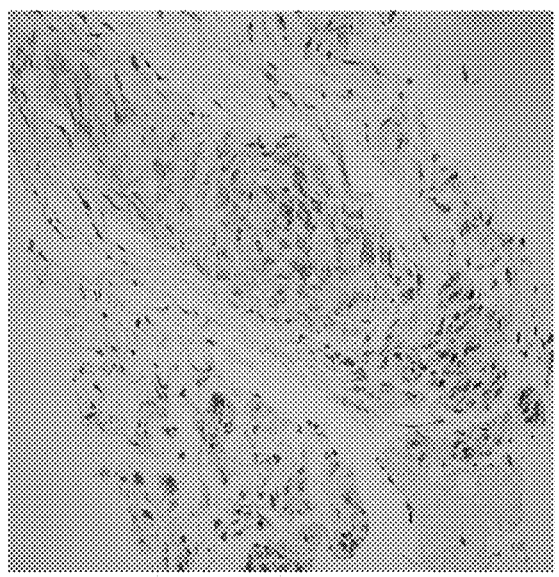
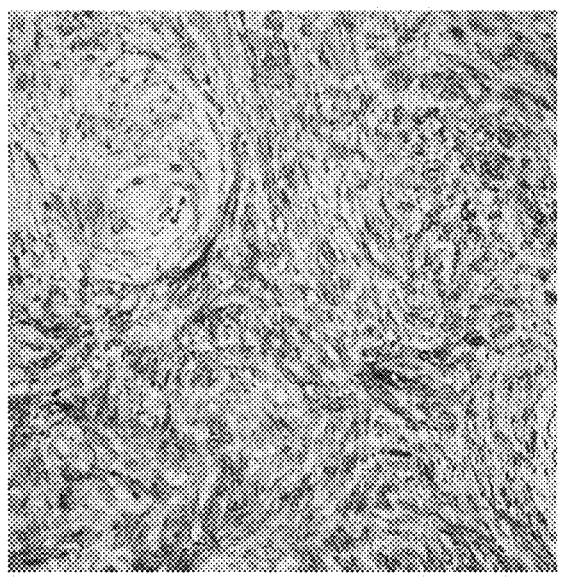
Fig. 2A            Fig. 2B
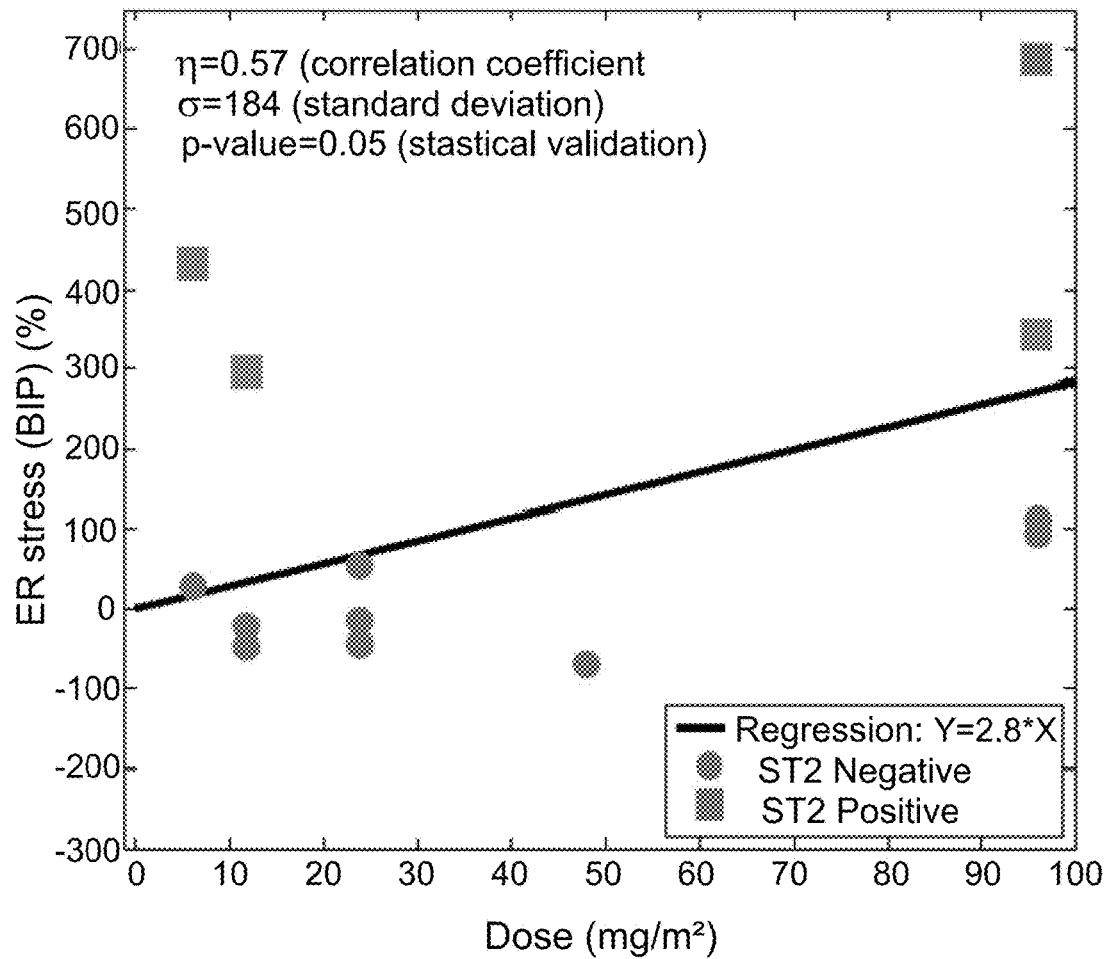
Fig. 3

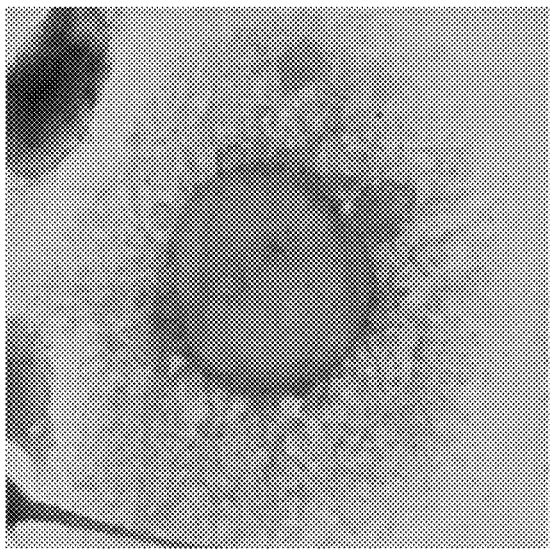
Fig. 9A Control OV90
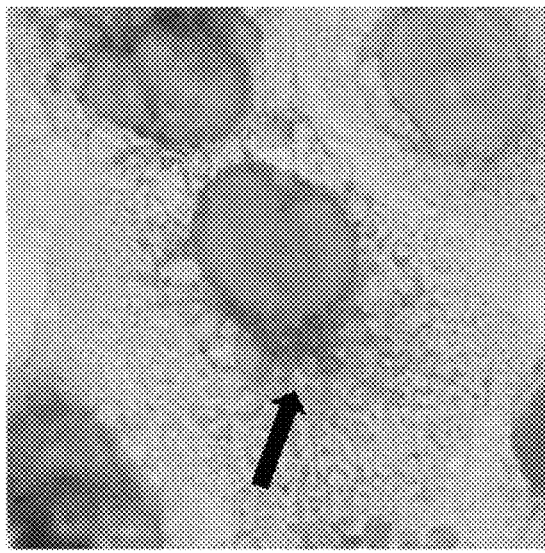
Fig. 9B 24+72hrs 50 µg/ml dTCApFs
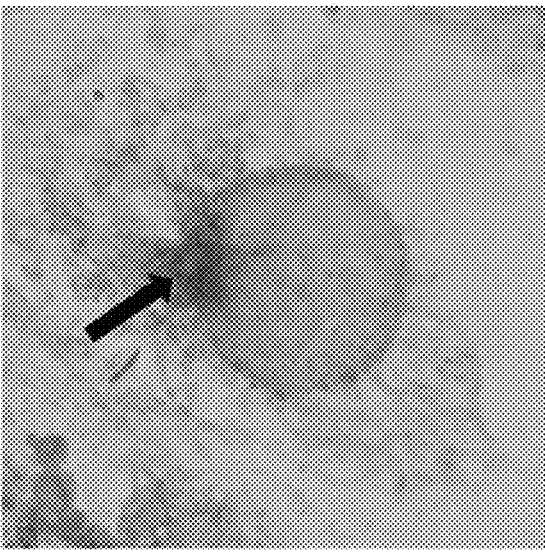
Fig. 9C OV90 ST2 KO
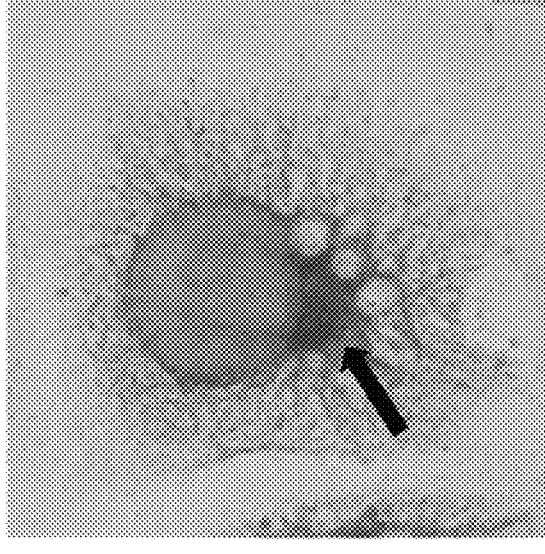
Fig. 9D

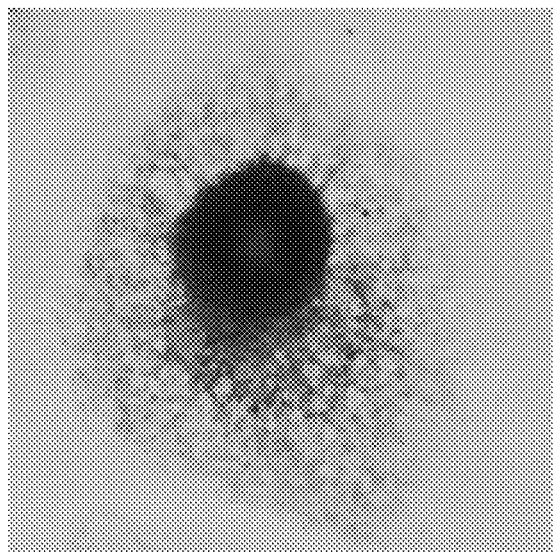
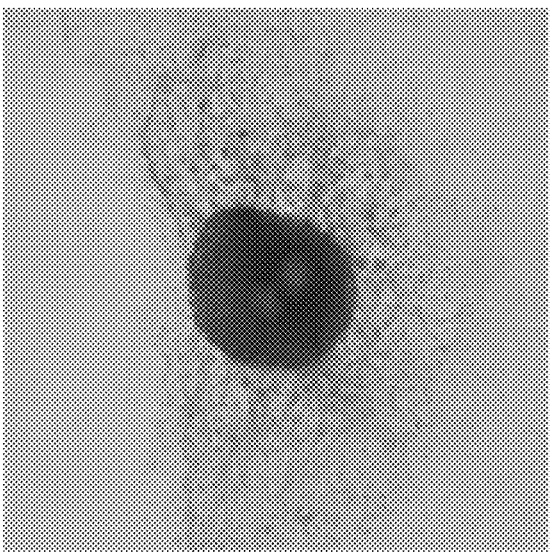
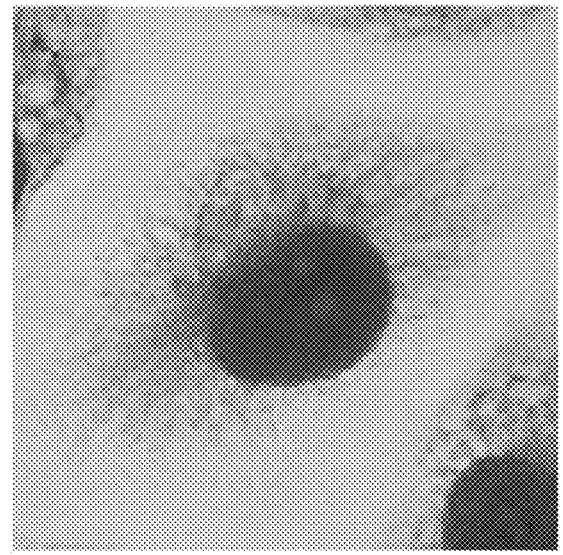
Fig. 10A OV90 — Control
Fig. 10B 24+72hrs 50 µg/ml dTCApFs
Fig. 10C OV90 ST2 KO
Fig. 10D

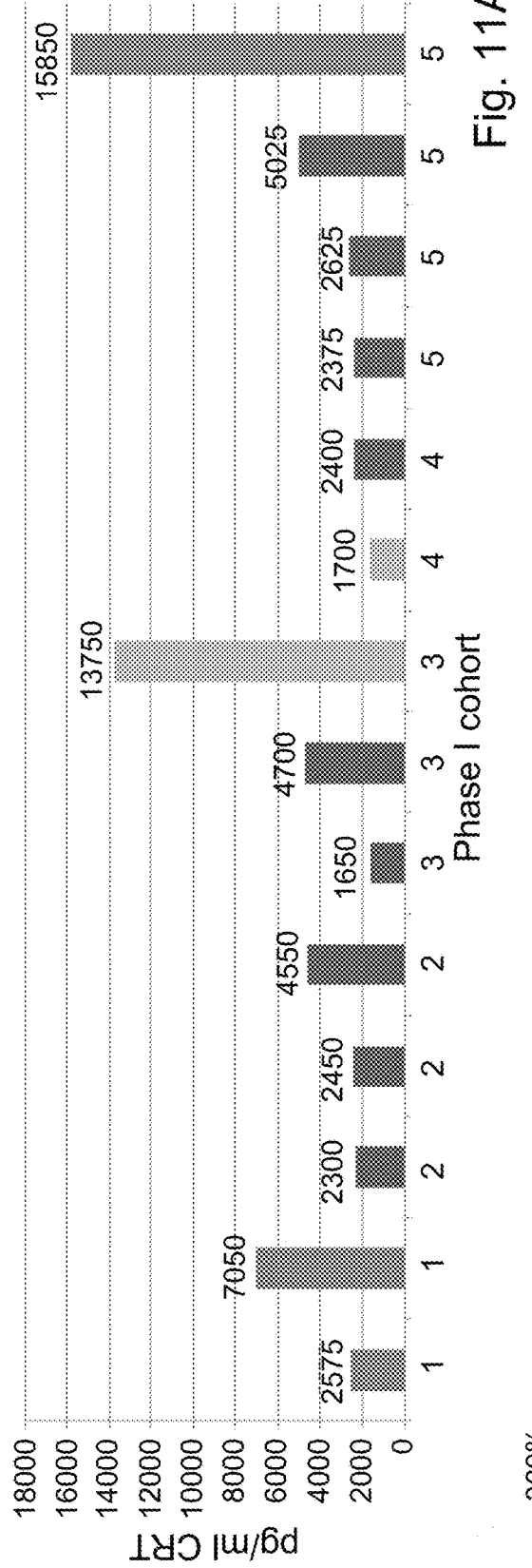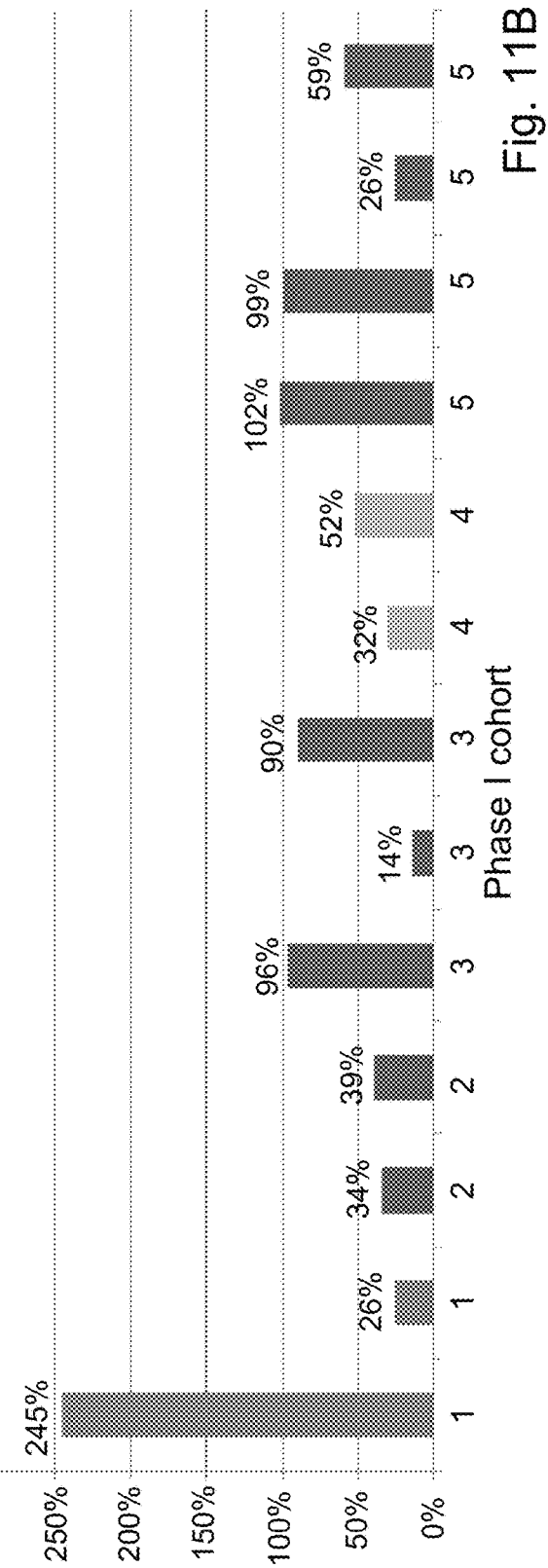

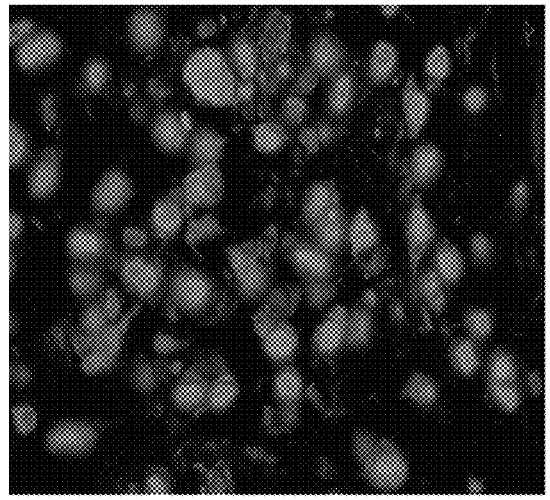
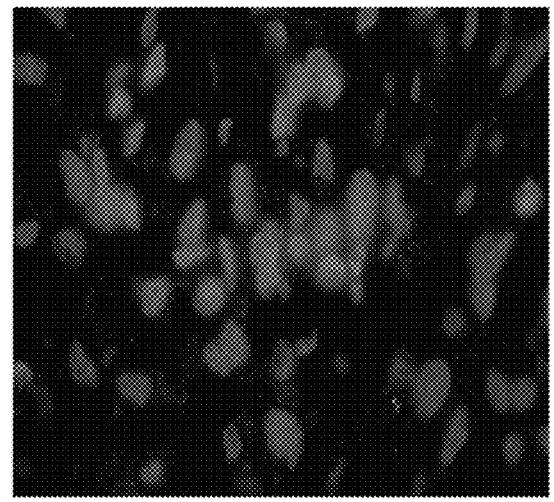
Fig.16A    Fig.16B
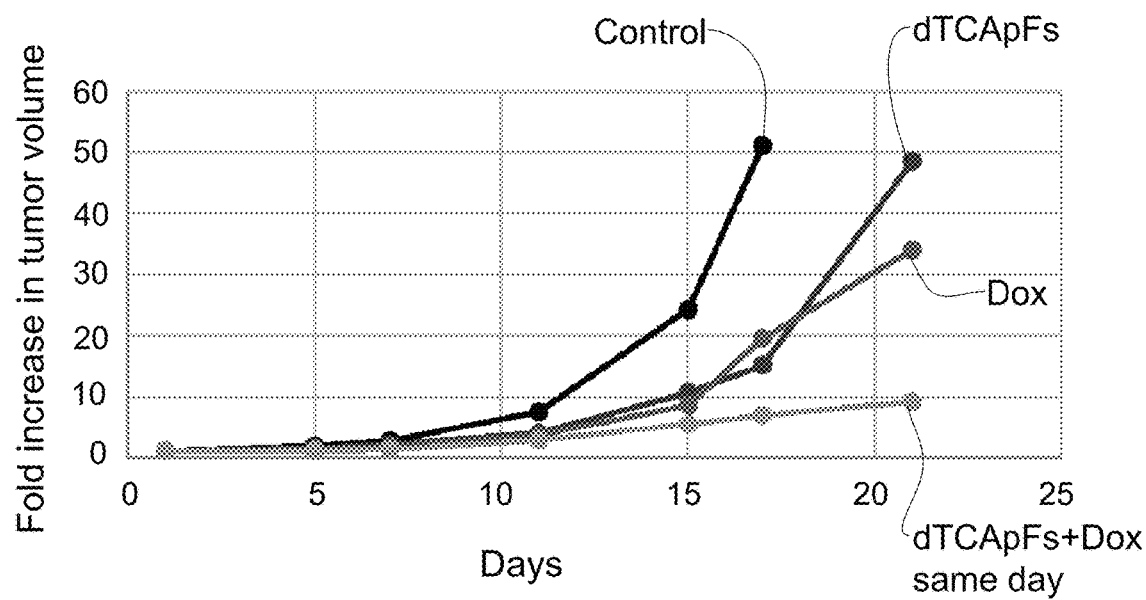
Fig.17

SEQUENCE LISTING

```
<160> NUMBER OF SEQ ID NOS: 1

<210> SEQ ID NO 1
<211> LENGTH: 14
<212> TYPE: PRT
<213> ORGANISM: Artificial Sequence
<220> FEATURE:
<223> OTHER INFORMATION: synthetic peptide termed "dTCApFs".
<220> FEATURE:
<221> NAME/KEY: MISC_FEATURE
<222> LOCATION: (1)..(1)
<223> OTHER INFORMATION: x is equal to D-Trp
<220> FEATURE:
<221> NAME/KEY: MISC_FEATURE
<222> LOCATION: (2)..(2)
<223> OTHER INFORMATION: x is equal to D-Trp
<220> FEATURE:
<221> NAME/KEY: MISC_FEATURE
<222> LOCATION: (3)..(3)
<223> OTHER INFORMATION: x is equal to D-Thr
<220> FEATURE:
<221> NAME/KEY: MISC_FEATURE
<222> LOCATION: (4)..(4)
<223> OTHER INFORMATION: x is equal to D-Phe
<220> FEATURE:
<221> NAME/KEY: MISC_FEATURE
<222> LOCATION: (5)..(5)
<223> OTHER INFORMATION: x is equal to D-Phe
<220> FEATURE:
<221> NAME/KEY: MISC_FEATURE
<222> LOCATION: (6)..(6)
<223> OTHER INFORMATION: x is equal to D-Leu
<220> FEATURE:
<221> NAME/KEY: MISC_FEATURE
<222> LOCATION: (7)..(7)
<223> OTHER INFORMATION: x is equal to D-Pro
<220> FEATURE:
<221> NAME/KEY: MISC_FEATURE
<222> LOCATION: (8)..(8)
<223> OTHER INFORMATION: x is equal to D-Ser
<220> FEATURE:
<221> NAME/KEY: MISC_FEATURE
<222> LOCATION: (9)..(9)
<223> OTHER INFORMATION: x is equal to D-Thr
<220> FEATURE:
<221> NAME/KEY: MISC_FEATURE
<222> LOCATION: (10)..(10)
<223> OTHER INFORMATION: x is equal to D-Leu
<220> FEATURE:
<221> NAME/KEY: MISC_FEATURE
<222> LOCATION: (11)..(11)
<223> OTHER INFORMATION: x is equal to D-Trp
<220> FEATURE:
<221> NAME/KEY: MISC_FEATURE
<222> LOCATION: (12)..(12)
<223> OTHER INFORMATION: x is equal to D-Glu
```

```
<220> FEATURE:
<221> NAME/KEY: MISC_FEATURE
<222> LOCATION: (13)..(13)
<223> OTHER INFORMATION: x is equal to D-Arg
<220> FEATURE:
<221> NAME/KEY: MISC_FEATURE
<222> LOCATION: (14)..(14)
<223> OTHER INFORMATION: x is equal to D-Lys

<400> SEQUENCE: 1

Xaa Xaa Xaa Xaa Xaa Xaa Xaa Xaa Xaa Xaa Xaa Xaa Xaa Xaa
1               5                   10
```

ENDOPLASMIC RETICULUM STRESS AS A PREDICTIVE TOOL IN CANCER THERAPY AND A COMBINATION THERAPY FOR THE TREATMENT OF CANCER

SEQUENCE LISTING

The Sequence Listing submitted in text format (.txt) filed on Jul. 31, 2018, named "SequenceListing.txt", created on Jul. 17, 2018 (1.60 KB), is incorporated herein by reference.

TECHNOLOGICAL FIELD

The present disclosure relates to personalized medicine. More specifically, the present disclosure provides methods, kits and compositions for use in predicting the effect of cancer therapy. In addition the present disclosure relates to combination therapy for reducing the standard of care doses of an anti-cancer agent in treated cancer patients.

BACKGROUND ART

References considered to be relevant as background to the presently disclosed subject matter are listed below:
[1] Mehta, S. et al., 2010, Therapeutic Advances in Medical Oncology 2(2): 125-148.
[2] Lee, A. S. 2007, Cancer Research 67(8): 3496-3499.
[3] Zheng, Y. Z. et al., 2014, Breast Cancer Research and Treatment 145: 349-358.
[4] Sato, M. et al., 2010, Advances in Genetics 69: 97-114.
[5] Han, K. S. et al., 2015, Oncotarget 6:34818-30.
[6] WO 2008/042508.
[7] US 2009/0181472.
[8] WO 02/082076.
[9] WO 02/077176.
[10] WO 2006/046239.
[11] WO 2007/122622
[12] WO 2007/091240.
[13] WO 2008/075349.
[14] Sandler, U. et al., 2010, Recent advances in clinical medicine, ISSN: 1790-5125.
[15] Sandler, U. et al., 2010, J Experimental Therapeutics and Oncology 8:327-339.
[16] WO 2015/083167.
[17] Eisenhauer, E. A. et al., 2009, European Journal of Cancer 45: 228-247.

Acknowledgement of the above references herein is not to be inferred as meaning that these are in any way relevant to the patentability of the presently disclosed subject matter.

BACKGROUND

Technological advances greatly increased the understanding of the molecular basis of tumor progression and numerous tumor and treatment response biomarkers have been identified to date (1).

These markers can be generally divided into two types, being prognostic markers which aim to objectively evaluate the patient's overall outcome, such as the probability of cancer recurrence after standard treatment and predictive markers which aim to evaluate the likelihood of benefit from a specific clinical intervention (1).

Among the cellular markers implicated with cancer development and prognosis is the glucose-regulated protein GRP78, also referred to as BiP (binding immunoglobulin protein), which primarily resides in the endoplasmic reticulum (ER). GRP78, which belongs to the HSP70 protein family, facilitates proper protein folding, prevents intermediates from aggregating, and targets misfolded protein for proteasome degradation. In addition, GRP78 serves as an ER stress signaling regulator. GRP78 promotes tumor proliferation, survival, metastasis and resistance to a wide variety of therapies and thus GRP78 expression may serve as a biomarker for tumor behavior and treatment response (2).

Consistent with the above, cancer cells adapt to chronic stress in the tumor environment by inducing expression of GRP78 (2), which functions as a potent anti-apoptotic factor and confers drug resistance (3). Indeed, it has been shown that the presence of GRP78 autoantibodies in cancer patients' sera is generally associated with poor prognosis (4). GRP78/BiP upregulation following anti-angiogenic therapy has been demonstrated in multiple studies. For example, Han et al. (5), showed that sunitinib treatment induced hypoxia in Caki-1 xenografts that was followed by elevated expression of GRP78/BiP in the treated group in comparison to the control group.

Therefore, GRP78 was proposed as a marker for various conditions, inter alia for determining whether a subject with cancer is at risk of developing resistance to hormonal therapy (6), as a prognostic marker for evaluating tumor grade in the case of head and neck cancer (7) or as a tumor marker of various cancers (8, 9). However, the mechanism by which GRP78 acts during cancer progression or cancer treatment is still not clear.

A peptide termed "T101" that is encoded by a cDNA unique for the human thymus was previously identified. This peptide as well as derivatives thereof were implicated, inter alia, for the treatment of cancer via the role of T101 as a stimulator of the immune system (WO 2006/046239, 10). WO 2006/046239 demonstrates that T101 is able to stimulate the immune system and to reduce tumor size, suggesting that the peptide affects the proliferation of cancer cells. WO 2006/046239 also suggests an immune-based role for T101, for example in protecting patients during the course of standard chemotherapy.

Treatment of cancer by using T101 was also suggested in WO 2007/122622 (11), which demonstrates, inter alia, the effect of T101 on the development of various types of tumors. The peptide T101 was also described in WO 2007/091240 (12), relating to treatment of immunological diseases and in WO 2008/075349 (13) as well as in the publications by Sandler et al. (14 and 15), relating to treating or preventing a disease involving a cell having T1/ST2 receptor.

In addition, a peptide derivative of T101, termed "Nerofe", has been reported to decrease the secretion of proteins that are known to be associated with cancer metastasis by cancer cells and to directly inhibit migration of cancer cells in vitro. In addition the peptide was shown to affect the serum level of vascular endothelial growth factor (VEGF) in cancer patients (WO 2015/083167, 16), and was suggested for use in a method of preventing or treating cancer metastasis.

GENERAL DESCRIPTION

By one of its aspects the present invention provides a method for predicting the response of a cancer patient to treatment with an isolated peptide comprising the amino acid sequence denoted by SEQ ID NO. 1 or a functional derivative thereof or a pharmaceutically acceptable salt of said isolated peptide, said method comprising the steps of:

(a) determining the expression level of at least one endoplasmic reticulum (ER) stress marker in at least one biological sample of said patient to obtain an expression value, wherein at least one of said biological samples is obtained after the initiation of said treatment;
(b) determining if the expression value of said at least one ER stress marker obtained in step (a) is higher or lower with respect to a predetermined standard expression value of said at least one ER stress marker;
wherein an expression value of said at least one ER stress marker obtained in (a) higher than an expression value of said at least one ER stress marker in a predetermined standard indicates that said patient is a responder to said treatment.

In some embodiments, an expression value of said at least one ER stress marker in said at least one biological sample higher than an expression value of said at least one ER stress marker in said predetermined standard indicates that said treatment should be continued.

In other embodiments the at least one ER stress marker is binding immunoglobulin protein (BiP), phosphorylated α subunit of eukaryotic initiation factor 2 (p-eIF2a), phosphorylated Inositol Requiring 1 (p-IRE), phosphorylated PKR-like ER kinase (p-PERK) or C/EBP homologous protein (CHOP) or any combination thereof. Various embodiments of the present disclosure relate to an ER stress marker which is binding immunoglobulin protein (BiP).

In some embodiments the expression level of said at least one ER stress marker in step (a) is determined in at least two temporally separated biological samples of said patient. In other specific embodiments one of said at least two biological samples is obtained before initiation of said treatment. In further embodiments the at least two temporally separated biological samples are separated by a week, two, three or four weeks, by a month, two, three or four months.

In various embodiments the method as herein defined further comprises administering the isolated peptide comprising the amino acid sequence denoted by SEQ ID NO. 1 or a functional derivative thereof or a pharmaceutically acceptable salt of said isolated peptide to said patient. In some embodiments the isolated peptide comprising the amino acid sequence denoted by SEQ ID NO. 1 or a functional derivative thereof or a pharmaceutically acceptable salt of said isolated peptide is administered at a dose of about 5 mg/m² to about 100 mg/m². In other embodiments the isolated peptide comprising the amino acid sequence denoted by SEQ ID NO. 1 or a functional derivative thereof or a pharmaceutically acceptable salt of said isolated peptide is administered at a frequency of once, twice or trice per week.

In further embodiments treatment as herein defined is with an isolated peptide consisting of the amino acid sequence denoted by SEQ ID NO. 1 or with a pharmaceutically acceptable salt of said isolated peptide.

In various embodiments of the present disclosure cancer is selected from the group consisting of pancreatic cancer, ovarian cancer, spindle cell neoplasm of neural origin, spindle cell neoplasm, metastatic colorectal cancer, colon cancer, colorectal cancer, colon adenocarcinoma, rectal cancer, rectal adenocarcinoma, lung cancer, non-small cell lung carcinoma, spinal cord neoplasm, breast cancer, skin cancer, renal cancer, multiple myeloma, thyroid cancer, prostate cancer, adenocarcinoma, head and neck cancer, gastrointestinal cancer, stomach cancer, cancer of the small intestine, hepatic carcinoma, liver cancer and malignancies of the female genital tract. In other specific embodiments cancer is selected from the group consisting of spindle cell neoplasm of neural origin, metastatic colorectal cancer, colon cancer, lung cancer, rectal cancer, pancreatic cancer and spinal cord neoplasm. In still further embodiments cancer cells in the patient are ST2 positive cells.

In some embodiments the method according to the invention comprises contacting at least one detecting agent specific for said at least one ER stress marker with said at least one biological sample or with any nucleic acid or protein product obtained therefrom. In various embodiments the at least one detecting agent specific for said at least one ER stress marker is an antibody or an antibody conjugated to a detectable moiety, wherein said antibody specifically recognizes and binds said ER stress marker.

The present disclosure further provides a detecting agent specific for an ER stress marker for use in a method of predicting the response of a cancer patient to treatment with an isolated peptide comprising the amino acid sequence denoted by SEQ ID NO. 1 or a functional derivative thereof or a pharmaceutically acceptable salt of said isolated peptide, said method comprising the steps of:
(a) determining the expression level of said ER stress marker with said detecting agent in at least one biological sample of said patient to obtain an expression value, wherein at least one of said biological samples is obtained after the initiation of treatment;
(b) determining if the expression value of said ER stress marker obtained in step (a) is higher or lower with respect to a predetermined standard expression value of said ER stress marker; wherein an expression value of said ER stress marker obtained in (a) higher than an expression value of said ER stress marker in a predetermined standard indicates that said patient is a responder to said treatment.

The present disclosure further provides a kit comprising:
(a) at least one detecting agent specific for determining the expression value of at least one ER stress marker in a biological sample; and optionally at least one of:
(b) predetermined standard expression values of said at least one ER stress marker determined for cancer patients before initiation of treatment and upon administration of an isolated peptide comprising the amino acid sequence denoted by SEQ ID NO. 1 or any functional derivative thereof or a pharmaceutically acceptable salt of said isolated peptide;
(c) at least one control sample.

In some embodiments the kit for determining the expression value of at least one ER stress marker further comprising at least one reagent for determining the level of expression of at least one ER stress marker in a biological sample.

In other embodiments the kit for determining the expression value of at least one ER stress marker further comprises:
(d) an isolated peptide comprising the amino acid sequence denoted by SEQ ID NO. 1 or a functional derivative thereof, or a pharmaceutically acceptable salt of said isolated peptide.

In further embodiments the kit for determining the expression value of at least one ER stress marker further comprises instructions for use.

In various embodiments the kit as herein defined is for use in predicting the response of a cancer patient to treatment with an isolated peptide comprising the amino acid sequence denoted by SEQ ID NO. 1 or a functional derivative thereof or a pharmaceutically acceptable salt of said isolated peptide.

The present disclosure further provides a combination therapy comprising an anti-cancer agent and an isolated peptide comprising the amino acid sequence denoted by SEQ ID NO. 1 or a functional derivative thereof or a pharmaceutically acceptable salt of said isolated peptide for use in a method of treating cancer, wherein said anti-cancer agent is administered at a dose lower than the standard of care dose of said anti-cancer agent.

In some embodiments the combination therapy for use is wherein the administered dose of said anti-cancer agent is lower than the standard of care dose of said anti-cancer agent by at least about 1%-50%, about 5%-45%, about 10%-40%, about 15%-35% or about 20%-30%.

In other embodiments the combination therapy for use is wherein said anti-cancer agent is a chemotherapeutic agent, a tyrosine kinase inhibitor, an immunotherapy agent, a hormone agent, a biological agent, a differentiation factor, an anti-angiogenic factor, an anti-autophagy agent or an immune-stimulatory agent. In further embodiments the combination therapy for use is wherein said anti-cancer agent is Taxol.

In still further embodiments the combination therapy for use is wherein said isolated peptide and said anti-cancer agent are administered concomitantly or consecutively.

In various embodiments of the aspect of combination therapy for use cancer is pancreatic cancer, ovarian cancer, spindle cell neoplasm of neural origin, spindle cell neoplasm, metastatic colorectal cancer, colon cancer, colorectal cancer, colon adenocarcinoma, rectal cancer, rectal adenocarcinoma, lung cancer, non-small cell lung carcinoma, spinal cord neoplasm, breast cancer, skin cancer, renal cancer, multiple myeloma, thyroid cancer, prostate cancer, adenocarcinoma, head and neck cancer, gastrointestinal cancer, stomach cancer, cancer of the small intestine, hepatic carcinoma, liver cancer or malignancies of the female genital tract. In specific embodiments of the aspect of combination therapy for use cancer is ovarian cancer or pancreatic cancer. In still further embodiments of the aspect of combination therapy for use cancer comprises ST2 positive cancer cells.

In some embodiments of the aspect of combination therapy for use the isolated peptide consists of the amino acid sequence denoted by SEQ ID NO. 1 or a pharmaceutically acceptable salt thereof.

In other embodiments of the aspect of combination therapy for use the isolated peptide or a pharmaceutically acceptable salt thereof is administered at a dose of about 5 mg/m$^2$ to about 100 mg/m$^2$. In further embodiments of the aspect of combination therapy for use the isolated peptide or a pharmaceutically acceptable salt thereof is administered at a frequency of once, twice or trice per week.

By another one of its aspects the present disclosure provides a therapeutic kit comprising:
(a) an anti-cancer agent; and
(b) an isolated peptide comprising the amino acid sequence denoted by SEQ ID NO. 1 or a functional derivative thereof or a pharmaceutically acceptable salt of said isolated peptide.
In some embodiments the therapeutic kit is wherein said kit further comprises instructions for use.

In other embodiments the therapeutic kit is for use in a method of treating cancer, wherein said anti-cancer agent is administered at a dose lower than the standard of care dose of said anti-cancer agent.

By still a further aspect the present disclosure provides a method of treatment of cancer in a patient in need thereof, comprising administering to said patient a therapeutically effective amount of an isolated peptide comprising the amino acid sequence denoted by SEQ ID NO. 1 a functional derivative thereof or a pharmaceutically acceptable salt of said isolated peptide in combination with an anti-cancer agent, wherein said isolated peptide reduces the standard of care administered dose of said anti-cancer agent.

BRIEF DESCRIPTION OF THE DRAWINGS

In order to better understand the subject matter that is disclosed herein and to exemplify how it may be carried out in practice, embodiments will now be described, by way of non-limiting example only, with reference to the accompanying drawings, in which:

FIG. 2A-FIG. 2B are micrographs of biopsy taken from a patient designated 002-006 suffering from spinal cord neoplasm. FIG. 2A describes binding immunoglobulin protein (BiP) staining of a biopsy obtained from the patient prior to receiving dTCApFs and FIG. 2B describes BiP staining of a biopsy obtained after 11 months of treatment with dTCApFs. The antibody used for staining was an anti-BiP antibody (Abcam).

FIG. 3 is a graph showing the correlation between change in the serum level of the ER stress marker BiP and the dose of dTCApFs.

FIG. 9A-FIG. 9D are immunocytochemistry images using an antibody directed to β-cop of control OV90 cells (FIG. 9A), OV90 cells treated with the dTCApFs peptide as indicated (FIG. 9B), of control OV90 ST2 knock-out (KO) cells (FIG. 9C) and of OV90 ST2 knock-out (KO) cells treated with the dTCApFs peptide as indicated (FIG. 9D).

FIG. 10A-FIG. 10D are immunocytochemistry images using an antibody directed to GRP78 BiP of control OV90 cells (FIG. 10A), OV90 cells treated with the dTCApFs peptide as indicated (FIG. 10B), of control OV90 ST2 knock-out (KO) cells (FIG. 10C) and of OV90 ST2 knock-out (KO) cells treated with the dTCApFs peptide as indicated (FIG. 10D).

FIG. 11A-FIG. 11B are bar graphs showing the serum CRT level in dTCApFs-treated patients at the end of the treatment (FIG. 11A) and the change in the CRT level in dTCApFs-treated patients (FIG. 11B).

FIG. 16A-FIG. 16B are micrographs showing fluorescence of KRAS in mice inoculated with MDA231 cells (hTNBC cells) that were not treated (FIG. 16A) or treated with a combination of dTCApFs and doxorubicin (FIG. 16B).

FIG. 17 is a graph showing the change in tumor volume during the indicated period of time, in mice inoculated with B16 cells and treated with dTCApFs (once a week at 15 mg/kg), doxorubicin (once a week at 3 mg/kg) or with a combination of dTCApFs and doxorubicin when dTCApFs and doxorubicin were administered on the same day. "Control" represents treatment of mice with 5% mannitol. Abbreviations: Dox, doxorubicin; dTCApFs+Dox same day, a combination of dTCApFs and doxorubicin administered on the same day.

DETAILED DESCRIPTION OF EMBODIMENTS

Figure 1:
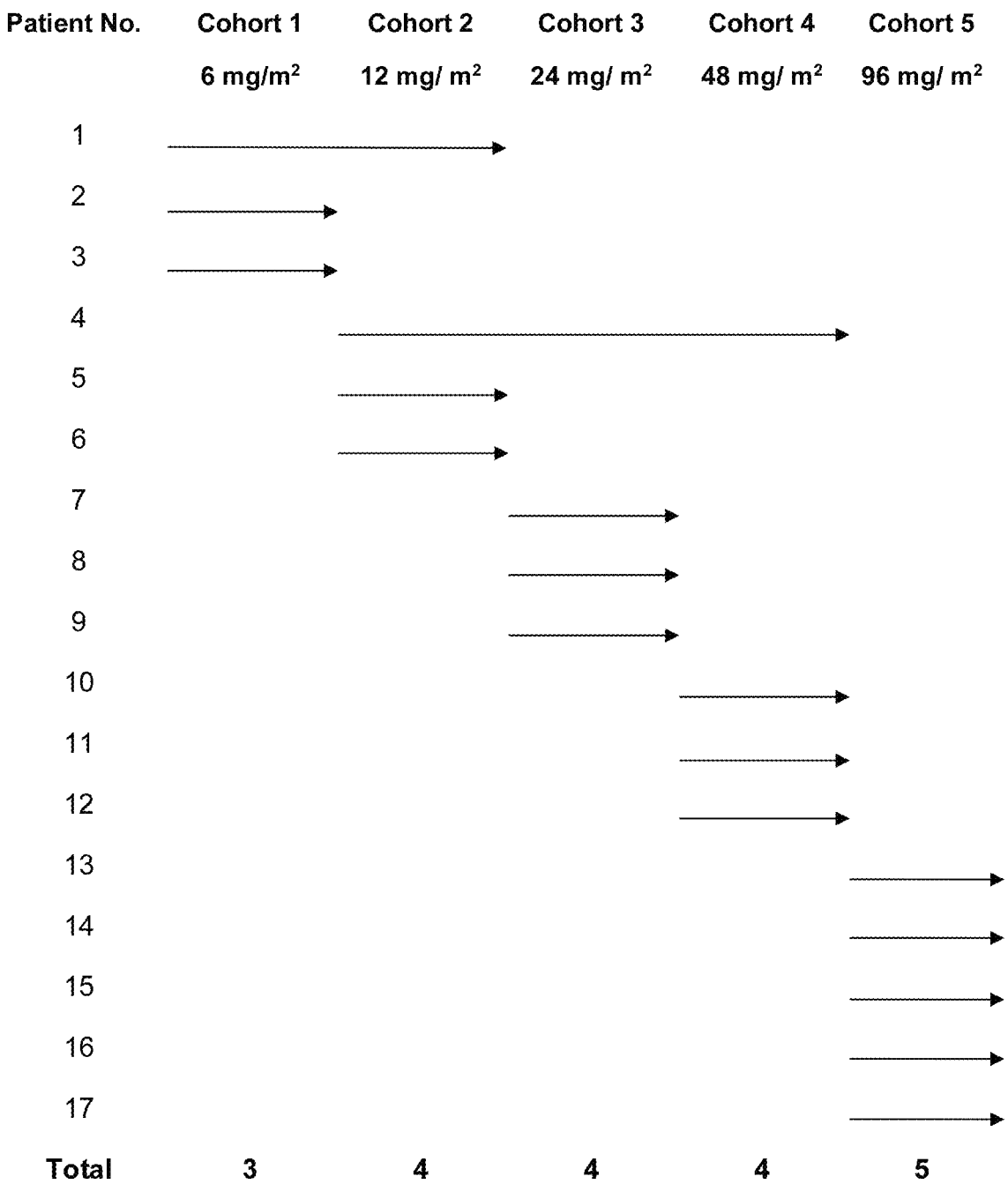
FIG. 1 is a summary of patients' randomization and assignments, showing patient number and assignment to a specific cohort as well as the dosing used in the study.

The present disclosure is based on the surprising finding that treatment with the peptide termed herein dTCApFs (or Nerofe), which has the all D amino acid sequence of Trp Trp Thr Phe Phe Leu Pro Ser Thr Leu Trp Glu Arg Lys (denoted by SEQ ID NO: 1) increased endoplasmic reticulum (ER) stress in a variety of cancers, as evidenced from an increase in the level of expression of the ER stress marker binding immunoglobulin protein (BiP). Remarkably, the observed increase in the ER stress marker BiP was found to correlate with an inhibition of tumor growth in dTCApFs-treated patients, as demonstrated by the decrease in tumor size at the end of the treatment period.

Thus, inter alia, the present disclosure shows that an ER stress marker, for example BiP, may be used as a biomarker for assessing the effect of treatment with the peptide dTCApFs in cancer patients.

Therefore in one of its aspects the present disclosure provides a method for predicting the response of a cancer patient to treatment with an isolated peptide comprising the amino acid sequence denoted by SEQ ID NO. 1 or a functional derivative thereof or a pharmaceutically acceptable salt of said isolated peptide, said method comprising the steps of:

(a) determining the expression level of at least one endoplasmic reticulum (ER) stress marker in at least one biological sample of said patient to obtain an expression value, wherein at least one of said biological samples is obtained after the initiation of said treatment;

(b) determining if the expression value of said at least one ER stress marker obtained in step (a) is higher or lower with respect to a predetermined standard expression value of said at least one ER stress marker;

wherein an expression value of said at least one ER stress marker obtained in (a) higher than an expression value of said at least one ER stress marker in a predetermined standard indicates that said patient is a responder to said treatment.

In other words, the present disclosure provides a method for determining, at an early stage (e.g. after about a month from treatment initiation as exemplified below or at further time-points), whether the cancer patient responds to treatment (i.e., whether the treatment is suitable) and to determine further treatment options based on these conclusions, e.g. whether it is advisable or not to proceed with this type of therapy.

Adjusting suitable treatment protocols is highly valuable and clinically desired in view of the fact that a large number of treatment protocols are often associated with undesired side effects, and moreover, may be unsuccessful. Thus, optimizing a treatment protocol at early stages after initiation of treatment and/or throughout or after a treatment period may avoid inadequate treatments, reduce unnecessary side effects and drug burden and improve the chance of success.

The term "prediction" or "predicting" as used herein with reference to the response of a cancer patient to treatment refers to the determination or evaluation of the likelihood that a patient will respond either favorably, namely will have a beneficial response, or unfavorably (namely will not experience a beneficial response) to treatment as herein defined. A patient with an overall beneficial response to treatment as herein defined is referred to as a "responder" while a patient that responds unfavorably to treatment is referred to as a "non-responder".

The term "response" in the context of the present disclosure refers to the patient's overall outcome as a result of treatment, which may be assessed using any clinical parameters known to a skilled practitioner in the field of the invention. Thus the term "responder" in the context of treatment as herein defined refers to a patient experiencing an overall improvement in at least one clinical parameter as compared to an untreated subject diagnosed with the same condition (e.g., the same type, stage, degree and/or classification of the cancer disease as herein defined), or as compared to the clinical parameters of the same subject prior to treatment initiation (or at the first day thereof, prior to the first administration) or as compared to the clinical parameters of a patient population for which an improvement in at least one clinical parameter was not achieved (defined herein as "non-responders").

The term "non-responder" to treatment refers to a patient not experiencing an improvement in at least one of the clinical parameter and is diagnosed with the same conditions (e.g., the same type, stage, degree and/or classification of the pathology), or experiencing the clinical parameters of the same subject prior to treatment as herein defined.

The meaning of an "improvement in clinical parameters" in the context of cancer is well known in the art, and includes but is not limited to reduction in tumor size; inhibition, at least partially, of tumor growth; reduction in the number of tumors; decrease in acceptable disease markers (namely any marker known in the art that is used for diagnosis or monitoring of a disease); inhibition (at least partial) of tumor cell metastasis; enhancement of anti-tumor immune response; relief, at least partial, of one or more symptoms associated with the tumor; increase in the length of survival following treatment; decreased mortality at a given point of time following treatment; etc. Thus in some embodiments a beneficial response is a decrease in tumor burden which may be assessed according to the RECIST guideline (17).

As detailed above the present disclosure provides a method for predicting the response of a cancer patient to treatment as herein defined by first determining the expression level of at least one endoplasmic reticulum (ER) stress marker in at least one biological sample of said patient to obtain an expression value, wherein at least one of said biological samples is obtained after the initiation of treatment. Then in step (b) it is determined whether the expression value of said at least one ER stress marker obtained in step (a) is higher or lower with respect to a predetermined standard expression value of said at least one ER stress marker. According to the method of the invention, when an expression value of said at least one ER stress marker obtained in (a) is higher than an expression value of said at least one ER stress marker in a predetermined standard, said patient is diagnosed as a "responder" to treatment.

It must be understood that expression values as defined below that are higher or lower in comparison with a corresponding predetermined standard expression value (or a cut-off value) of a control sample predict whether the patient is a "responder" or a "non-responder".

Therefore the method comprises examining whether the expression value of any one of the tested ER stress markers is within the range of the expression value of a standard population or a cutoff value for such population or higher than the expression value of a standard population or a cutoff value for such population. The expression value is referred to as "higher" than a corresponding predetermined standard expression value wherein the expression value obtained for a certain ER stress marker at a certain time point of treatment equals to or is higher by any one of about 1% to 99.9%, specifically, about 1% to about 5%, about 5% to 10%, about 10% to 15%, about 15% to 20%, about 20% to 25%, about 25% to 30%, about 30% to 35%, about 35% to 40%, about 40% to 45%, about 45% to 50%, about 50% to 55%, about 55% to 60%, about 60% to 65%, about 65% to 70%, about 75% to 80%, about 80% to 85% about 85% to 90%, about 90% to 95%, about 95% to 99%, or about 99% to 99.9% or more than an expression value obtained at a corresponding time point of treatment for a standard population (namely a predetermined standard expression value).

Accordingly the term "lower" refers to any expression value below a predetermined standard expression value, for example by any one of about 1% to 99.9%, specifically, about 1% to about 5%, about 5% to 10%, about 10% to 15%, about 15% to 20%, about 20% to 25%, about 25% to 30%, about 30% to 35%, about 35% to 40%, about 40% to 45%, about 45% to 50%, about 50% to 55%, about 55% to 60%, about 60% to 65%, about 65% to 70%, about 75% to 80%, about 80% to 85% about 85% to 90%, about 90% to 95%, about 95% to 99%, or about 99% to 99.9%.

In other words, the specific expression values of the tested samples are compared to a predetermined cutoff or standard values. As used herein the term "comparing" denotes any examination of the expression level and/or expression values obtained for samples tested according to the invention in order to discover similarities or differences between at least two different samples. It should be noted that comparing according to the present invention encompasses the possibility to use a computer based approach.

The term "predetermined standard expression value" or "predetermined standard expression values" as herein defined refers to expression levels, optionally normalized to obtain expression values as defined below, of an ER stress marker in a population of responders to treatment as herein defined, preferably at time points corresponding to the time point(s) at which the expression values according to the method of the invention are obtained. For example but not limited to the expression levels obtained for the patients enrolled in the clinical trial described herein below. These patients serve as exemplary predetermined standard responder population or predetermined standard expression value for the ER stress marker BiP in samples obtained before the treatment and samples obtained at day 29 of treatment.

It should be noted that a predetermined standard expression value, sometimes referred to simply as "cutoff" herein, is a value that meets the requirements for both high diagnostic sensitivity (true positive rate) and high diagnostic specificity (true negative rate). It should be noted that the terms "sensitivity" and "specificity" are used herein with respect to the ability of one or more ER stress markers, to correctly classify a sample as belonging to a pre-established population associated with responsiveness to treatment as herein defined.

In certain alternative embodiments, a control sample (or a control biological sample) may be used (instead of, or in addition to, predetermined standard expression value). Accordingly, the expression values of the ER stress marker are compared to the expression values in the control sample. The control sample may be obtained from at least one of a healthy subject, a subject suffering from the same pathologic disorder and is not treated by the isolated peptide as herein defined, the treated patient prior to treatment, a subject that responds to treatment and a non-responder subject.

As indicated above the present disclosure is based on the surprising finding that treatment with the peptide dTCApFs (denoted by SEQ ID NO: 1) increased stress in the endoplasmic reticulum (ER) in tumors obtained from a variety of cancer patients, in correlation with positive patients' response to the treatment. The ER has an important role in the folding and maturation of newly synthesized proteins. ER stress, as known in the art, refers to the disruption of ER homeostasis that is manifested by the accumulation of misfolded and unfolded proteins in the ER. ER stress activates complex signaling networks, for example the network referred to as the Unfolded Protein response (UPR), which acts to reduce ER stress and to restore homeostasis.

The unfolded protein response (UPR) is initiated by three ER transmembrane proteins: Inositol Requiring 1 (IRE1), PKR-like ER kinase (PERK), and Activating Transcription Factor 6 (ATF6). During unstressed conditions, the ER chaperone, immunoglobin binding protein (BiP) binds to the luminal domains of these master regulators keeping them inactive. Upon ER stress, BiP dissociates from these sensors resulting in their activation.

The activated UPR regulates downstream effectors with the following three distinct functions: adaptive response, feedback control, and cell fate regulation. The UPR adaptive response includes inter alia upregulation of molecular chaperones and protein processing enzymes to increase folding. Feedback control involves the negative regulation of UPR activation as ER homeostasis is being re-established. Cell fate regulation by the UPR plays an important role in the pathogenesis of ER stress-related disorder. As known in the art, when the cell encounters ER stress that the UPR can mitigate, the cell will survive. However, during unresolvable ER stress conditions, the UPR fails to reduce ER stress and restore homeostasis, promoting cell death.

Other pathways associated with ER stress are the endoplasmic-reticulum-associated protein degradation (ERAD) which is a cellular pathway that targets misfolded proteins of the endoplasmic reticulum for ubiquitination and subsequent degradation by a protein-degrading complex (namely the proteasome) and ER stress-mediated apoptosis.

Thus, the term "endoplasmic reticulum stress marker" or "ER stress marker" refers to any molecule associated with endoplasmic reticulum stress response, for example but not limited to any molecule associated with the signaling network referred to as the unfolded protein response (UPR) that acts to reduce ER stress and restore homeostasis, any molecule associated with endoplasmic-reticulum-associated protein degradation (ERAD) or any molecule associated with ER stress-mediated apoptosis.

In some embodiments the ER stress marker as herein defined is glucose-regulated protein (GRP-78) also termed binding immunoglobulin protein (BiP), Inositol Requiring 1 (IRE1), PKR-like ER kinase (PERK), the α subunit of eukaryotic initiation factor 2 (eIF2α), type II ER transmembrane transcription factor (ATF6) or C/EBP homologous protein (CHOP).

As detailed above an increase in the level of expression of the binding immunoglobulin protein (BiP) ER marker was detected in patients administered with the peptide dTCApFs, in correlation with an inhibition of tumor growth in these patients.

Therefore in various embodiments the methods, detecting agent specific for an ER stress marker for use and kit according to the present disclosure are wherein said ER stress marker is binding immunoglobulin protein (BiP). The term binding immunoglobulin protein (BiP) and glucose-regulated protein GRP78 are used interchangeably and refer to the same ER stress marker.

The term "Binding immunoglobulin protein" (BiP), also known as 78 kDa glucose-regulated protein (GRP-78) or heat shock 70 kDa protein 5 (HSPA5), refers to a protein that in humans is encoded by the HSPA5 gene and that acts as a molecular chaperone located in the lumen of the endoplasmic reticulum (ER). BiP binds newly synthesized proteins as they are translocated into the ER, and maintains them in a state competent for subsequent folding and oligomerization. BiP is also an essential component of the translocation machinery, and plays a role in transport across the ER membrane of aberrant proteins destined for degradation by the proteasome. BiP is an abundant protein under all growth conditions, but its synthesis is markedly induced under conditions that lead to the accumulation of unfolded polypeptides in the ER. In specific embodiments of the present disclosure BiP is human BiP, having the accession UniProtKB number P11021.

Specifically, by another one of its aspects the present disclosure provides a method for predicting the response of a cancer patient to treatment with an isolated peptide comprising the amino acid sequence denoted by SEQ ID NO. 1 or a functional derivative thereof or a pharmaceutically acceptable salt of said isolated peptide, said method comprising the steps of:

(a) determining the expression level of BiP in at least one biological sample of said patient to obtain an expression value, wherein at least one of said biological samples is obtained after the initiation of said treatment;

(b) determining if the expression value of BiP obtained in step (a) is higher or lower with respect to a predetermined standard expression value of BiP;

wherein an expression value of BiP obtained in (a) higher than an expression value of BiP in a predetermined standard indicates that said patient is a responder to said treatment.

In other specific embodiments the ER stress marker according to the present disclosure is Inositol Requiring 1 (IRE1). IRE1, a type I ER transmembrane kinase, senses ER stress by its N-terminal luminal domain. Upon sensing the presence of unfolded or misfolded proteins, IRE1 dimerizes and autophosphorylates to become active.

In other specific embodiments the ER stress marker according to the present disclosure is PKR-like ER kinase (PERK). PERK is also a type I ER transmembrane kinase, which when activated by ER stress, oligomerizes, autophosphorylates and then directly phosphorylates Ser51 on the α subunit of eukaryotic initiation factor 2 (eIF2α).

Thus in further specific embodiments the ER stress marker according to the present disclosure is the α subunit of eukaryotic initiation factor 2 (eIF2α).

In still further specific embodiments, the ER stress marker according to the present disclosure is type II ER transmembrane transcription factor (ATF6). ATF6 has two isoforms, ATF6α and ATF6β.

In other specific embodiments the ER stress marker according to the present disclosure is the ER stress-mediated apoptosis such as C/EBP homologous protein (CHOP).

In still further specific embodiment the ER stress marker as herein defined is a phosphorylated protein, for example p-eIF2α, p-IRE1 or p-PERK.

Therefore in the above and other embodiments the ER stress marker according to the present disclosure is binding immunoglobulin protein (BiP), phosphorylated α subunit of eukaryotic initiation factor 2 (p-eIF2α), phosphorylated Inositol Requiring 1 (p-IRE), phosphorylated PKR-like ER kinase (p-PERK) or C/EBP homologous protein (CHOP) or any combination thereof.

In some embodiments the method, detecting agent specific for an ER stress marker for use or kit according to the present disclosure indicate that said treatment should be continued. In other words, in some embodiments of the method, detecting agent specific for an ER stress marker for use or kit according to the present disclosure an expression value of said at least one ER stress marker in said at least one biological sample higher than an expression value of said at least one ER stress marker in said predetermined standard indicates that said treatment should be continued.

In some embodiments a patient is a responder to treatment in accordance with the present disclosure when the patient experiences at least one of cancer regression, progression-free survival, disease-free survival, complete response or partial response.

Alternatively, in case the expression value of said at least one ER stress marker in said at least one biological sample of a patient is lower than the expression value of the same ER stress marker in a predetermined standard, treatment should be arrested.

As noted above, the methods of the present disclosure are based on determining the expression level of at least one ER stress marker in biological samples. The terms "level of expression" or "expression level" are used interchangeably and generally refer to a numerical representation of the amount (quantity) of a polypeptide (protein) or polynucleotide which encodes an amino acid product or protein in a biological sample. "Expression" generally refers to the process by which gene-encoded information is converted into the structures present and operating in the cell and may be evaluated via measurement of the quantity of the polypeptide (protein) or polynucleotide which encodes thereof.

Determination of the expression level of at least one ER stress marker may also be based on the expression level of fragments of the polypeptide (protein) or the polynucleotide encoding thereof, or on the expression level of any post-translationally modified protein (e.g. phosphorylated protein) or fragments thereof.

Determining the expression level of an endoplasmic reticulum stress marker (e.g. BiP) or of any polypeptide fragment or derivative thereof or of any nucleic acid encoding thereof may be performed by any method known in the art, using a detecting agent specific for the endoplasmic reticulum stress marker being examined. For example, determining the expression level of an ER stress marker may be performed using ELISA, immunoassay, immunofluorescence, immunohistochemistry, immunoprecipitation, northern blot, western blot, PCR, immuno-PCR, or surface plasmon resonance.

In particular, determining the expression level of the ER stress marker BiP may be performed as described below using an ELISA-based method or using labelled antibodies (e.g. labelled antibodies directed to BiP). Determining the expression level of an ER stress marker (e.g. BiP) may also be based on determining the expression level of a nucleic acid (e.g. mRNA) that encodes for BiP protein or by determining the expression level of any polypeptide fragment or derivative of BiP in a biological sample.

In certain and specific embodiments, the step of determining the level of expression to obtain an expression value by the method of the invention further comprises an additional and optional step of normalization. According to this embodiment, in addition to determination of the level of expression of the at least one ER stress marker as herein defined, the level of expression of at least one suitable control reference gene (e.g., housekeeping genes) is being determined in the same sample. According to such embodiment, the expression level of the at least one stress marker of the invention obtained in step (a) is normalized according to the expression level of said at least one reference control gene obtained in the additional optional step in said test sample, thereby obtaining a normalized expression value. Optionally, similar normalization is performed also in at least one control sample or a representing standard when applicable (namely the predetermined standard as herein defined).

Thus the term "expression value" refers to the result of a calculation that uses as an input the "level of expression" or "expression level" obtained experimentally and by normalizing the "level of expression" or "expression level" by at least one normalization step as detailed herein, the calculated value termed herein "expression value" is obtained.

More specifically, as used herein, "normalized values" or "expression values" are the quotient of raw expression values of ER stress markers, divided by the expression value of a control reference gene from the same sample, such as a stably-expressed housekeeping control gene. The division of the raw expression level of an ER stress marker by the control reference gene raw expression level yields a quotient or a measure which is essentially free from any technical failures or inaccuracies and constitutes a normalized expression value of said marker gene. This normalized expression value may then be compared with normalized cutoff values, i.e., cutoff values calculated from normalized expression values. In certain embodiments, the control reference gene may be a gene that maintains stable in all samples analyzed in the microarray analysis.

In specific embodiments the method and kit as herein defined comprise contacting at least one detecting agent specific for said at least one ER stress marker with said at least one biological sample or with any nucleic acid or protein product obtained therefrom.

As indicated below the determination of the ER stress marker BiP was based on the use of antibodies directed to BiP. Therefore in some embodiments of the method, detecting agent specific for an ER stress marker for use and kit according to the present disclosure the detecting agent specific for the (at least one) ER stress marker is an antibody or an antibody conjugated to a detectable moiety, wherein said antibody specifically recognizes and binds said ER stress marker.

By the term "detecting agent specific for an ER stress marker" as herein defined it is meant any agent specific for an ER stress marker that may be used for quantifying the level of the relevant ER stress marker expression in a sample (for example but not limited to a nucleic acid agent specific for detecting an mRNA encoding the relevant ER stress marker or a specific antibody that binds and recognizes the relevant ER stress marker or a fragment thereof).

Still further, it must be understood that any of the detecting agent specific for an ER stress marker or reagents used by the kits and in any step of the methods of the invention are non-naturally occurring products or compounds, As such, none of the detecting molecules of the invention are directed to naturally occurring compounds or products.

In some embodiments the ER stress marker is BiP and the term "detecting agent specific for BiP" means any agent specific for BiP that may be used for quantifying the level of BiP expression in a sample (e.g. a nucleic acid agent specific for detecting an mRNA coding for BiP or a specific antibody that binds and recognizes BiP or fragment thereof).

The term "antibody" is used herein in its broadest sense and encompasses but is not limited to a single chain antibody, a monoclonal antibody, a bi-specific antibody, a chimeric antibody, a synthetic antibody, a polyclonal antibody, a humanized antibody, a fully human antibody, or active fragments or homologues thereof. In the above and other embodiments the antibody as herein defined is a non-naturally occurring antibody. An antibody conjugated to a detectable moiety refers to any antibody conjugated to a detectable moiety so as to have a tag which is detectable by fluorescence, chemiluminescence and the like (also referred to herein as a "labelled antibody").

The term "contacting" means to bring, put, incubate or mix together. As such, a first item is contacted with a second item when the two items are brought or put together, e.g., by touching them to each other or combining them. In the context of the present invention, the term "contacting" includes all measures or steps which allow interaction between the at least one of the detection molecules for the ER stress markers (and optionally one suitable control reference gene) and the nucleic acid or amino acid molecules of the tested sample(s).

Thus by another one of its aspects the present disclosure provides a detecting agent specific for an ER stress marker for use in a method (performed in vitro) of predicting the response of a cancer patient to treatment with an isolated peptide comprising the amino acid sequence denoted by SEQ ID NO. 1 or a functional derivative thereof or a pharmaceutically acceptable salt of said isolated peptide, said method comprising the steps of:
(a) determining the expression level of said ER stress marker with said detecting agent in at least one biological sample of said patient to obtain an expression value, wherein at least one of said biological samples is obtained after the initiation of treatment;
(b) determining if the expression value of said ER stress marker obtained in step (a) is higher or lower with respect to a predetermined standard expression value of said ER stress marker;
wherein an expression value of said ER stress marker obtained in (a) higher than an expression value of said ER stress marker in a predetermined standard indicates that said patient is a responder to said treatment.

The method of the present invention further relates to repeated determination of the patient's response to treatment as herein defined, at various time points during treatment, namely in "temporally separated" biological samples of the patient, thereby monitoring the continued response of the patient. When the expression value of the at least one ER stress marker obtained in step (a) of the method as herein defined for each one of the temporally separated biological samples is higher than the expression value of the same at least one ER stress marker in a predetermined standard obtained for a corresponding population (responders) at corresponding time point(s) along treatment, treatment may be continued.

For example the difference in the ER stress marker levels, e.g., BiP level, may be calculated by comparing the expression levels of the ER stress marker between two biological samples obtained from the same patient. The first biological sample is a control biological sample obtained from the patient prior to treatment or at the first day of treatment (before the first administration) or the first biological sample is a predetermined standard expression level of the relevant ER stress marker, obtained from patients having the same condition and clinical status prior to treatment. The second biological sample is a biological sample of said patient obtained after the initiation of treatment. The above procedure may be repeated.

For example and as exemplified below, the second biological sample may be obtained about four weeks (e.g. on day 29) after initiation of treatment and the first biological sample (the control biological sample) is obtained prior to treatment or at the first day of said treatment before the first administration. Specifically, when the ER stress marker is BiP, the difference is BiP expression levels is measured as follows: [(BiP level at day 29)−(BiP level at day 1)]*100/(BiP level at day 1)

Therefore in specific embodiments the at least one biological sample in step (a) of the method as herein defined is obtained about four weeks after the initiation of said treatment.

In various embodiments, the method, detecting agent specific for an ER stress marker for use or kit according to the present disclosure is wherein the expression level of said at least one ER stress marker in step (a) is determined in at least two temporally separated biological samples of said patient.

The term "temporally separated" in the context of biological samples as herein defined refers to biological samples obtained at different time points, for example but not limited to prior to treatment and at day 29 of treatment.

In other embodiments the method, detecting agent specific for an ER stress marker for use or kit according to the present disclosure are wherein one of said at least two biological samples is obtained before initiation of said treatment, where "initiation of treatment" or "treatment initiation" should be taken to mean the administration of the first dose of the isolated peptide as herein defined. By the term "before initiation of said treatment" it is meant before the first administration of the isolated peptide. In some embodiments the term "before initiation of said treatment" refers to the first day of treatment before the first administration is made.

In other specific embodiments the method, detecting agent specific for an ER stress marker for use or kit according to the present disclosure is wherein said at least two temporally separated biological samples are separated by a week, two, three or four weeks, by a month, two, three or four months. In further embodiments the method, detecting agent specific for an ER stress marker for use or kit according to the present disclosure is wherein said at least two temporally separated biological samples are separated by more than four months.

The term "biological sample" is used herein in its broadest sense and refers to samples obtained from a mammal subject. Biological samples may be obtained from mammals (including humans) and encompass fluids, solids and tissues.

In some embodiments the biological sample is blood, plasma, serum, lymph fluid, urine, a tissue sample, a biopsy sample or a cell lysate.

As detailed above the biological sample is obtained after the initiation of treatment as herein defined, or before (prior to) the initiation of said treatment. Biological samples may be obtained by any method known in the art by a skilled physician.

Figure 12:
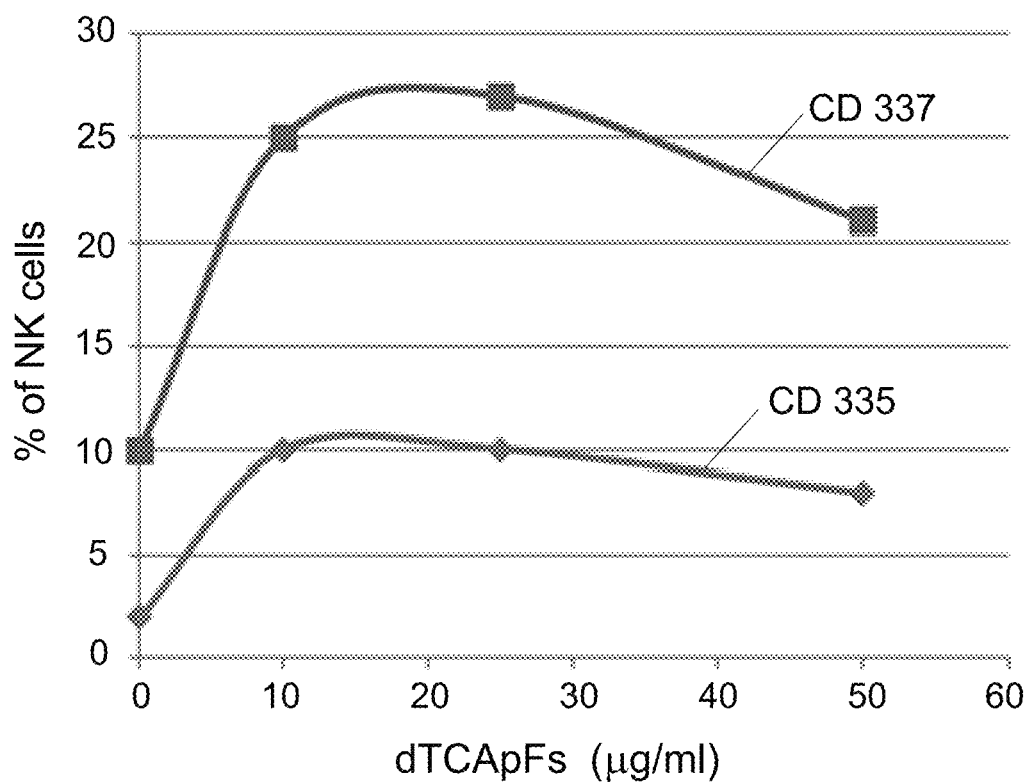
FIG. 12 is a graph showing the activation of natural killer cells (NK cells) in the presence of dTCApFs.

As described in the Examples below, the effect of dTCApFs was also examined on human natural killer (NK) cells. As shown in FIG. 12, an increase in expression of the receptors CD335 and CD337 was induced by dTCApFs. Natural killer cells provide a rapid response to viral-infected cells and respond to tumor formation. Without wishing to be bound by theory, the activation of the receptors CD335 and CD337 by dTCApFs is associated with increasing ER stress in these cells. Therefore in some embodiments measurement of the ER stress may be performed in patients' cells, e.g. NK cells.

Furthermore the term "at least one" with reference to a biological sample refers to one, two, three, four, five, six, seven, eight, nine or more biological samples. Mutatis mutandis the term "at least one" in the context of ER stress markers refers to one, two, three, four, five, six, seven, eight, nine or more ER stress markers.

According to the results shown in Example 1 below, a clear difference in the level of BiP was observed in a biopsy obtained from a spinal cord neoplasm patient before treatment was initiated (FIG. 2A) as compared to the level of BiP observed in a biopsy obtained from the same patient after 11 month of treatment (FIG. 2B). The above results demonstrate that the dTCApFs peptide increased ER stress in tumors obtained from a spinal cord neoplasm cancer patient.

In addition, the results shown in Example 2 below demonstrate that an increase in the level of BiP correlated with complete inhibition of tumor growth in patients having different cancers types that were treated with the peptide dTCApFs under the conditions specified herein.

As used herein to describe the present disclosure, "cancer" or "tumor" relate equivalently to a hyperplasia of a tissue or organ. If the tissue is a part of the lymphatic or immune systems, malignant cells may include non-solid tumors of circulating cells. Malignancies of other tissues or organs may produce solid tumors. In general, the methods and compositions of the present disclosure may be used in the treatment of non-solid and solid tumors.

In some embodiments cancer is selected from the group consisting of pancreatic cancer, ovarian cancer, spindle cell neoplasm of neural origin, spindle cell neoplasm, metastatic colorectal cancer, colon cancer, colorectal cancer, colon adenocarcinoma, rectal cancer, rectal adenocarcinoma, lung cancer, non-small cell lung carcinoma, spinal cord neoplasm, breast cancer, skin cancer, renal cancer, multiple myeloma, thyroid cancer, prostate cancer, adenocarcinoma, head and neck cancer, gastrointestinal cancer, stomach cancer, cancer of the small intestine, hepatic carcinoma, liver cancer and malignancies of the female genital tract.

In further embodiments of the present disclosure cancer is selected from the group consisting of spindle cell neoplasm of neural origin, metastatic colorectal cancer, colon cancer, lung cancer, rectal cancer, pancreatic cancer and spinal cord neoplasm.

In the clinical study described below a correlation was found between the anti-tumour activity of dTCApFs and the T1/ST2 expression status in patients' tumour cells. A direct correlation was found between T1/ST2-positivity, tumour size changes and induction of ER stress. These findings are consistent with the preclinical studies described below in Example 4 showing that incubation of ST2 gene knockout OV-90 cells with dTCApFs did not result in ER stress. Without wishing to be bound by theory these observations suggest that the T1/ST2 receptor may be a biomarker for selecting T1/ST2 positive patients who are more likely to positively respond to dTCApFs.

Therefore in still further embodiments the methods of the present disclosure further comprises determining the ST2 receptor status of the cells in biological sample(s) obtained from the patient under dTCApFs treatment. As detailed below, the changes from baseline in the levels of soluble T1/ST2 receptor and peripheral blood mononuclear cell (PBMC) T1/ST2 receptor expression are also monitored in pretreatment and/or on-treatment tumor tissue samples obtained from the patient undergoing treatment with dTCApFs.

Without wishing to be bound by theory, expression of the ST2 receptor on cancer cells facilitates dTCApFs entry into the cells. Therefore in some embodiments of the method, detecting agent specific for an ER stress marker for use or kit as herein defined the cancer cells in patients are ST2 positive cells.

The term "ST2 receptor" or T1/ST2 receptor (also referred to as "T1/ST2" and "ST2/T1") as herein defined refers to a member of the IL-IR superfamily, which possesses three extracellular immunoglobulin domains and an intracellular TIR domain. T1/ST2 has been indicated as being involved in cardiovascular disease. The term "ST2 positive cells" as herein defined refers to cells for which the presence of the ST2 receptor on the cells is identified by any method known in the art for example but not limited to the method described below.

In further embodiments the method or detecting agent specific for an ER stress marker for use according to the present disclosure is wherein the method further comprises administering the isolated peptide comprising the amino acid sequence denoted by SEQ ID NO. 1 or a functional derivative thereof or a pharmaceutically acceptable salt of said isolated peptide to the patient.

Therefore by still a further aspect the present disclosure provides a method for predicting the response of a cancer patient to treatment with an isolated peptide comprising the amino acid sequence denoted by SEQ ID NO. 1 or a functional derivative thereof or a pharmaceutically acceptable salt of said isolated peptide, said method comprising the steps of:

(a) administering said isolated peptide comprising the amino acid sequence denoted by SEQ ID NO. 1 or a functional derivative thereof or said pharmaceutically acceptable salt of said isolated peptide to the patient;

(b) determining the expression level of at least one endoplasmic reticulum (ER) stress marker in at least one biological sample of said patient to obtain an expression value, wherein at least one of said biological samples is obtained after the initiation of said treatment;

(c) determining if the expression value of said at least one ER stress marker obtained in step (b) is higher or lower with respect to a predetermined standard expression value of said at least one ER stress marker;

wherein an expression value of said at least one ER stress marker obtained in (a) higher than an expression value of said at least one ER stress marker in a predetermined standard indicates that said patient is a responder to said treatment.

The isolated peptide comprising the amino acid sequence denoted by SEQ ID NO. 1 or a functional derivative thereof or a pharmaceutically acceptable salt of said isolated peptide may be administered by any route of administration known to a person skilled in the art, for example intravenously (iv).

The isolated peptide as herein defined may be administered at an "effective amount" such that necessary to achieve the desired therapeutic result. The "effective amount" is determined by the severity of the disease in conjunction with the therapeutic objectives, the route of administration and the patient's general condition (age, sex, weight and other considerations known to the attending physician).

As detailed below, an on-going clinical trial is being performed by the inventors, in accordance with which the cancer type, dose, administration frequency, treatment length, administration and other parameters were determined. As detailed below, the dosing regimen was 6, 12, 24, 48 or 96 mg/m$^2$ (for example as shown in FIG. 1).

In various embodiments the isolated peptide comprising the amino acid sequence denoted by SEQ ID NO. 1 or a functional derivative thereof or a pharmaceutically acceptable salt of said isolated peptide is administered at a dose of about 5 mg/m$^2$ to about 100 mg/m$^2$, 90 mg/m$^2$, 80 mg/m$^2$, 70 mg/m$^2$, 60 mg/m$^2$ or about 10 mg/m$^2$ to about 50 mg/m$^2$.

In specific embodiments the method or detecting agent specific for an ER stress marker for use as herein defined is wherein said isolated peptide comprising the amino acid sequence denoted by SEQ ID NO. 1 or a functional derivative thereof or said pharmaceutically acceptable salt of said isolated peptide is administered at a dose of about 5 mg/m$^2$ to about 100 mg/m$^2$.

In further specific embodiments the isolated peptide comprising the amino acid sequence denoted by SEQ ID NO. 1 or a functional derivative thereof or a pharmaceutically acceptable salt of said isolated peptide is administered at a dose of about 6, 12, 24, 48 or 96 mg/m$^2$ dTCApFs.

In still further specific embodiments the method, detecting agent specific for an ER stress marker for use or kit as herein defined is wherein said isolated peptide comprising the amino acid sequence denoted by SEQ ID NO. 1 or a functional derivative thereof or a pharmaceutically acceptable salt of said isolated peptide is administered at a frequency of once, twice or trice per week.

In yet further specific embodiments the isolated peptide comprising the amino acid sequence denoted by SEQ ID NO. 1 or a functional derivative thereof or a pharmaceutically acceptable salt of said isolated peptide is administered at a frequency of 3 times per week.

As exemplified below treatment with dTCApFs (at 6, 12, 24, 48 and 96 mg/m$^2$, 3 times/week, in consecutive 28-day cycles) in locally advanced or metastatic solid tumors was safe and well-tolerated, with a dose dependent, linear PK. dTCApFs suppressed antigenic factors, induced anti-cancer cytokines production, and ER stress, which probably led to the clinical outcome observed in some of the patients. Positive T1/ST2 staining could serve as a predictive marker for response to dTCApFs.

Therefore the present invention further provides a method of treatment of cancer in a patient in need thereof, comprising administering to said patient a therapeutically effective amount of an isolated peptide comprising the amino acid sequence denoted by SEQ ID NO. 1, a functional derivative thereof or a pharmaceutically acceptable salt of said isolated peptide. In some embodiments the therapeutically effective amount of the isolated peptide is about 6, 12, 24, 48, or 96 mg/m$^2$. In yet further embodiments the isolated peptide is administered three times per week for a period of at least about four consecutive weeks. In still further specific embodiments the isolated peptide is the peptide termed herein dTCApFs consisting of the amino acid sequence denoted by SEQ ID NO: 1.

In other specific embodiments the therapeutically effective amount of the isolated peptide is about 24, 48, or 96 mg/m$^2$ or higher. In further specific embodiments the therapeutically effective amount is about 24 mg/m$^2$ (or higher), for a period of at least about four weeks and the patient is further administered with the isolated peptide at a higher therapeutically effective amount of about 48, 96 mg/m$^2$ or higher.

The terms "treat", "treating", "treatment" as used herein mean ameliorating, alleviating or eliminating one or more clinical parameters, symptoms or indications of disease activity in a patient having cancer. The clinical parameters associated with cancer as known in the art and as detailed above are for example tumor size, tumor growth, number of tumors, disease markers, tumor cell metastasis etc. By "patient" it is meant any mammal for which administration of the isolated peptide as herein defined, or any pharmaceutical composition of the invention is desired, namely patient afflicted with cancer as herein defined, in particular human patients.

Monitoring the treatment as herein defined may be performed by any means known in the art for monitoring cancer patient's response to treatment, for example according to the RECIST guideline (17).

As detailed below the present disclosure concerns inter alia results associated with an on-going clinical trial performed with the peptide dTCApFs, having the all D amino acid sequence of Trp Trp Thr Phe Phe Leu Pro Ser Thr Leu Trp Glu Arg Lys (as denoted by SEQ ID NO: 1).

The term "isolated peptide" as herein defined encompasses an isolated peptide comprising the amino acid sequence denoted by SEQ ID NO. 1 (namely the amino acid sequence Trp Trp Thr Phe Phe Leu Pro Ser Thr Leu Trp Glu Arg Lys in an all D conformation), termed herein "dTCApFs" or "Nerofe" and functional derivatives of the amino acid sequence denoted by SEQ ID NO. 1 or pharmaceutically acceptable salts of said isolated peptide.

Any pharmaceutically acceptable salt of the isolated peptide as herein defined are encompassed by the present disclosure, in particular the acetate salt of the peptide.

In some embodiment the isolated peptide consists of the amino acid sequence denoted by SEQ ID NO. 1, having the all D amino acid sequence of Trp Trp Thr Phe Phe Leu Pro Ser Thr Leu Trp Glu Arg Lys. In specific embodiments the isolated peptide according to the present disclosure is a pharmaceutically acceptable salt of the amino acid sequence denoted by SEQ ID NO. 1, for example the acetate salt thereof.

In other words in various embodiments the method, detecting agent specific for an ER stress marker for use or kit according to the invention is wherein said treatment is with an isolated peptide consisting of the amino acid sequence denoted by SEQ ID NO. 1 or with a pharmaceutically acceptable salt of said isolated peptide.

In other specific embodiments the present disclosure provides a method for predicting the response of a cancer patient to treatment with an isolated peptide consisting of the amino acid sequence denoted by SEQ ID NO. 1 or with a pharmaceutically acceptable salt of said isolated peptide, said method comprising the steps of:
(a) determining the expression level of BiP in at least one biological sample of said patient to obtain an expression value, wherein at least one of said biological samples is obtained after the initiation of said treatment;

(b) determining if the expression value of BiP obtained in step (a) is higher or lower with respect to a predetermined standard expression value of BiP;

wherein an expression value of BiP obtained in (a) higher than an expression value of BiP in a predetermined standard indicates that said patient is a responder to said treatment In other words, the present disclosure provides methods, detecting agent specific for an ER stress marker for use, composition and kit for predicting a cancer patient's response to treatment with an isolated peptide consisting of the amino acid sequence denoted by SEQ ID NO. 1 or with a pharmaceutically acceptable salt of said isolated peptide.

The term "peptide" as herein defined refers to a molecular chain of amino acid residues, which, if required, can be modified at each one of its amino acid residues, for example by manosylation, glycosylation, amidation (for example C-terminal amides), carboxylation or phosphorylation. The peptide may be obtained synthetically, through genetic engineering methods, expression in a host cell, or through any other suitable means. Methods for producing peptides are well known in the art.

The term "isolated" refers to molecules, such as amino acid sequences or peptides that are removed from their natural environment, isolated or separated.

The term "amino acid" as used herein, refers to naturally occurring and synthetic amino acid residues, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine.

The term amino acid encompasses L-amino acids and D-amino acids, which are mirror images of L-amino acids, where the chirality at carbon alpha has been inverted. D-amino acids are highly resistant to protease mediated degradation and have a low immunogenic response.

The terms "amino acid sequence" or "peptide sequence" also relate to the order in which amino acid residues, connected by peptide bonds, lie in the chain in peptides and proteins. The sequence is generally reported from the N-terminal end containing free amino group to the C-terminal end containing free carboxyl group.

By the term "comprising" it is meant that the isolated peptide in accordance with the present disclosure includes the peptide denoted by SEQ ID NO: 1, but may also include additional amino acid residues at the N-terminus or at the C-terminus of the peptide or at both termini.

As indicated above, the present disclosure also encompasses isolated peptides comprising derivatives of the peptide having the amino acid sequence denoted by SEQ ID NO. 1.

By the term "derivative" or "derivatives" it is meant to include peptides, which comprise the amino acid sequence denoted by SEQ ID NO: 1, but differ in one or more amino acids in their overall sequence, namely, which have deletions, substitutions (e.g. replacement of at least one amino acid by another amino acid), inversions or additions within the overall sequence of SEQ ID NO: 1. This term also encompasses the replacement of at least one amino acid residue in the overall sequence by its respective L amino acid residue.

In particular embodiments the present disclosure relates to a functional derivative of the amino acid sequence denoted by SEQ ID NO. 1, wherein said functional derivative has at least 70%, 75%, 80%, 85%, 90%, more preferably 95%, in particular 99% identity to the amino acid sequence denoted by SEQ ID NO: 1.

Amino acid "substitutions" are the result of replacing one amino acid with another amino acid having similar structural and/or chemical properties, i.e., conservative amino acid replacements. Amino acid substitutions may be made on the basis of similarity in polarity, charge, solubility, hydrophobicity, hydrophilicity, and/or the amphipathic nature of the residues involved. For example, each of the following eight groups contains amino acids that are conservative substitutions for one another:

1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M).

It is appreciated that these peptide derivatives must not alter the biological activity of the original peptide. The term "functional" means to denote that the modified peptide (namely the derivative) retains a biological activity qualitatively similar to that of the unmodified peptide. The biological activity of the derivative may be determined as herein described, namely by monitoring the effect of said derivative upon administration to an animal model, as known in the art.

In some embodiments the isolated peptide as herein defined or a pharmaceutically acceptable salt thereof is comprised in a pharmaceutical composition.

The term "pharmaceutical compositions" as herein defined refers to the isolated peptide comprising the amino acid sequence denoted by SEQ ID NO. 1 or a functional derivative thereof, or a pharmaceutically acceptable salt of said isolated peptide and optionally at least one pharmaceutically acceptable excipient or carrier as known in the art. As used herein "pharmaceutically acceptable carrier" includes any and all solvents, dispersion media, coatings, antibacterial and antifungal agents and the like. The use of such media and agents for pharmaceutical active substances is well known in the art. Except as any conventional media or agent is incompatible with the active ingredient, its use in the therapeutic composition is contemplated.

Pharmaceutical compositions used to treat subjects in need thereof according to the present disclosure optionally also comprise a buffering agent, an agent who adjusts the osmolarity thereof, and optionally, one or more pharmaceutically acceptable additives as known in the art.

Pharmaceutical compositions used to treat subjects in need thereof according to the invention, which may conveniently be presented in unit dosage form, may be prepared according to conventional techniques well known in the pharmaceutical industry, for example as detailed in the Examples below.

It should be understood that in addition to the ingredients particularly mentioned herein, the compositions according to the present disclosure may also include other agents conventional in the art having regard to the type of formulation in question.

Still further the present disclosure provides a kit comprising:

(a) at least one detecting agent specific for determining the expression value of at least one ER stress marker in a biological sample; and optionally at least one of:

(b) predetermined standard expression values of said at least one ER stress marker determined for cancer patients before initiation of treatment and upon administration of an isolated peptide comprising the amino acid sequence denoted by SEQ ID NO. 1 or any functional derivative thereof or a pharmaceutically acceptable salt of said isolated peptide;
(c) at least one control sample.

By the term "detecting agent specific for determining the expression value" of at least one ER stress marker it is meant any detecting agent specific for an ER stress marker as herein defined and optionally an additional detecting agent specific for determining the level of expression of at least one suitable control reference gene, as defined above.

The control sample may comprise a biological sample or any polypeptide/nucleic acid derived therefrom.

In specific embodiments the kit according to the present disclosure further comprises at least one reagent for determining the level of expression of at least one ER stress marker in a biological sample. Any reagents known in the art for such purpose are encompassed, for example but not limited to secondary antibodies dyes and fluorescent agents.

In further embodiment the kit according to the present disclosure further comprises:
(d) an isolated peptide comprising the amino acid sequence denoted by SEQ ID NO. 1 or a functional derivative thereof, or a pharmaceutically acceptable salt of said isolated peptide.

In other embodiments the kit according to the present disclosure further comprises instructions for use. Such instructions may comprise at least one of: instructions for carrying out the determination of the expression value of at least one ER stress marker in a biological sample; and instructions for comparing the expression values of at least one ER stress marker in a biological sample to the predetermined standard expression values of said at least one ER stress marker.

In still further embodiments the kit according to the present disclosure is wherein said at least one ER stress marker is BiP.

In other embodiments the kit according to the present disclosure is for use in predicting the response of a cancer patient to treatment with an isolated peptide comprising the amino acid sequence denoted by SEQ ID NO. 1 or a functional derivative thereof or a pharmaceutically acceptable salt of said isolated peptide.

As exemplified below higher abundance of ST2 receptors on cells facilitated the entry of the dTCApFs peptide to cells. Without wishing to be bound by theory, this may enable increasing ER stress in cancer cells of treated patients, and may enable lowering the doses of the administered isolated peptide or any additional agent administered therewith.

Most anti-cancer agents are strong medicines that have a fairly narrow dose range for safety and effectiveness reasons. Taking too little of an agent will not treat the cancer well and taking too much may cause life-threatening side effects. Chemotherapy is known for the adverse effects associated therewith. Common side effects are, among others, fatigue, pain, mouth and throat sores, diarrhea, nausea and vomiting. Ways for limiting or reducing the doses of administered chemotherapeutic agents are therefore desirable.

As indicated below, the beneficial therapeutic effect of the dTCApFs peptide on cancer cells and the understanding of its unique association with ER stress served as a basis for a further aspect of the present invention, according to which dTCApFs is combined with another anti-cancer therapeutic agent. Without wishing to be bound by theory, as a consequence of the effect of dTCApFs on ER stress, dTCApFs may allow a significant reduction in the administered amount of an additional anti-cancer agent, and thereby indirectly reduce the associated side effects thereof while maintaining the anti-tumor effect of the drug.

A study in which dTCApFs was administered in combination with an additional anti-cancer therapeutic agent, for example Taxol is described below. Surprisingly, while each one of the agents, namely dTCApFs and Taxol, had only a marginal effect on cell viability, combining dTCApFs with Taxol resulted in a synergistic effect and substantial reduction in cell viability. Therefore, a combination of dTCApFs with an anti-cancer agent allows the reduction of the standard of care administered dose of the anti-cancer agent during cancer therapy.

Therefore by still another one of its aspects the present disclosure provides a combination therapy comprising an anti-cancer agent and an isolated peptide comprising the amino acid sequence denoted by SEQ ID NO. 1 or a functional derivative thereof or a pharmaceutically acceptable salt of said isolated peptide for use in a method of treating cancer, wherein said anti-cancer agent is administered at a dose lower than the standard of care dose of said anti-cancer agent.

The term "combination therapy" as used herein refers to concomitant (simultaneous) or consecutive administration of two or more agents, namely an isolated peptide comprising the amino acid sequence denoted by SEQ ID NO. 1 or a functional derivative thereof and an anti-cancer agent. For example, concurrent administration can mean one dosage form containing the two or more agents or administration of a mixture of the two or more agents whereas consecutive administration means separate dosage forms administered to the patient at different time points and may be even by different routes of administration.

Thus in some embodiments of the present disclosure the isolated peptide of the invention and said anti-cancer agent are administered concomitantly or consecutively.

Thus the term "standard of care dose of said anti-cancer agent" as used herein refers to a dose recommended by a skilled physician for treatment of a certain type of cancer in a cancer patient based on considerations such as the anti-cancer agent(s) to be administered, the patient's age, gender, weight and relevant clinical parameters associated with the disease and the general health condition of the patient. While some anti-cancer agents are determined according to the patient body weight in kilograms, for some anti-cancer agent doses are determined based on body surface area (BSA), which doctors calculate using height and weight. BSA is expressed in meters squared ($m^2$). Dosages for children and adults differ, even after BSA is taken into account.

As indicated below, combining the peptide dTCApFs with Taxol resulted in a synergistic effect and substantial reduction in cell viability. Therefore, a combination therapy of the dTCApFs peptide with an anti-cancer agent may allow the reduction of the standard of care administered dose of the anti-cancer agent during cancer therapy.

In some embodiments of the present disclosure the combination therapy for use according to the present disclosure is wherein the administered dose of said anti-cancer agent is lower than the standard of care dose of said anti-cancer agent by at least about 1%-50%, about 5%-45%, about 10%-40%, about 15%-35% or about 20%-30%.

The term "anti-cancer agent" also known as "anticancer drug" or "antineoplastic drug" is used in its broader sense and encompasses any drug or agent that is effective in the treatment of malignant or cancerous disease. There are several classes of anticancer drugs, inter alia alkylating agents (e.g. Cyclophosphamide), antimetabolites (e.g. 5FU), natural products, immunotherapeutic agent, hormones and inhibitors.

In some embodiments the anti-cancer agent according to the present disclosure is a chemotherapeutic agent, a tyrosine kinase inhibitor, an immunotherapy agent (e.g. an antibody, an antibody fragment or a monoclonal antibody that down-regulates inhibitory immune receptors), a hormone agent, a biological agent, a differentiation factor, an anti-angiogenic factor, an anti-autophagy agent or an immune-stimulatory agent.

A "chemotherapeutic agent" as known in the art is a drug that targets cells at different phases of the process of forming new cells. Examples of chemotherapeutic agent include but are not limited to alkylating agents, antimetabolites (e.g. 5-FU), anti-tumour antibiotics, topoisomerase inhibitors, mitotic inhibitors (e.g. Paclitaxel or Taxol) or corticosteroids, to name but few.

The term "tyrosine kinase inhibitor" as known in the art refers to a drug that inhibits tyrosine kinases. Tyrosine kinases are enzymes responsible for the activation of many proteins by signal transduction cascades. The proteins are activated by adding a phosphate group to the protein (phosphorylation), a step that tyrosine kinase inhibitors inhibit.

The terms "an immunotherapy agent" or "immune-stimulatory agent" in the context of the present disclosure refers to cancer immunotherapy, which attempts to stimulate the immune system to destroy tumours.

The term "biological agent" in the context of cancer treatment as known in the art (sometimes referred to as "immune therapy") involves the use of living organisms, substances derived from living organisms, or laboratory-produced versions of such substances to treat disease. Some biological therapies for cancer use vaccines or bacteria to stimulate the body's immune system to act against cancer cells. Biological therapies that interfere with specific molecules involved in tumour growth and progression are also referred to as targeted therapies.

The term "anti-angiogenic factor" as known in the art refers to an agent that interferes with angiogenesis, the process of creation of new blood vessels. Anti-angiogenesis agents are types of targeted therapy that use drugs or other substances to stop tumours from making the new blood vessels they need to keep growing.

The term "anti-autophagy agent" as known in the art refers to a drug that interferes with the process autophagy, namely the regulated, destructive mechanism of the cell that disassembles unnecessary or dysfunctional components (e.g. bleomycin, doxorubicin).

In further embodiments the anti-cancer agent according to the present disclosure is a chemotherapeutic agent, a tyrosine kinase inhibitor, an immunotherapy agent, a hormone agent, a biological agent, a differentiation factor, an anti-angiogenic factor, an anti-autophagy agent or an immune-stimulatory agent In specific embodiments the anti-cancer agent is Taxol.

In some embodiments the present disclosure provides a combination therapy comprising an anti-cancer agent and an isolated peptide consisting of the amino acid sequence denoted by SEQ ID NO. 1 or a pharmaceutically acceptable salt of said isolated peptide for use in a method of treating cancer, wherein said anti-cancer agent is administered at a dose lower than the standard of care dose of said anti-cancer agent.

In further specific embodiments the present disclosure provides a combination therapy comprising taxol and an isolated peptide consisting of the amino acid sequence denoted by SEQ ID NO. 1 or a pharmaceutically acceptable salt of said isolated peptide for use in a method of treating cancer, wherein taxol is administered at a dose lower than the standard of care dose of said anti-cancer agent.

In some embodiments the isolated peptide or the pharmaceutically acceptable salt thereof is administered at a dose of about 5 mg/m$^2$ to about 100 mg/m$^2$.

In further embodiments the isolated peptide or a pharmaceutically acceptable salt thereof is administered at a frequency of once, twice or trice per week. In specific embodiments the isolated peptide or a pharmaceutically acceptable salt thereof is administered at a frequency of three times per week.

In still further embodiments the isolated peptide, the anti-cancer agent, or any pharmaceutically acceptable salt thereof, together or separately are comprised in a pharmaceutical composition.

In some embodiments the combination therapy for use according to the present disclosure is wherein said cancer is pancreatic cancer, ovarian cancer, spindle cell neoplasm of neural origin, spindle cell neoplasm, metastatic colorectal cancer, colon cancer, colorectal cancer, colon adenocarcinoma, rectal cancer, rectal adenocarcinoma, lung cancer, non-small cell lung carcinoma, spinal cord neoplasm, breast cancer, skin cancer, renal cancer, multiple myeloma, thyroid cancer, prostate cancer, adenocarcinoma, head and neck cancer, gastrointestinal cancer, stomach cancer, cancer of the small intestine, hepatic carcinoma, liver cancer or malignancies of the female genital tract.

In other embodiments, the combination therapy for use according to the present disclosure is wherein said cancer is ovarian cancer or pancreatic cancer. In further embodiments, the combination therapy for use according to the present disclosure is wherein said cancer is breast cancer, preferably wherein said breast cancer is triple negative breast cancer (TNBC).

In further embodiments the combination therapy for use according to the present disclosure is wherein said cancer comprises ST2 positive cancer cells.

In still further embodiments the combination therapy for use according to the present disclosure is wherein said isolated peptide consists of the amino acid sequence denoted by SEQ ID NO. 1 or a pharmaceutically acceptable salt thereof.

In further embodiments the combination therapy for use according to the present disclosure is wherein said isolated peptide or a pharmaceutically acceptable salt thereof is administered at a dose of about 5 mg/m$^2$ to about 100 mg/m$^2$.

In still further embodiments the combination therapy for use according to the present disclosure is wherein said isolated peptide or a pharmaceutically acceptable salt thereof is administered at a frequency of once, twice or trice per week.

The present disclosure further provides a therapeutic kit comprising:
(a) an anti-cancer agent; and
(b) an isolated peptide comprising the amino acid sequence denoted by SEQ ID NO. 1 or a functional derivative thereof or a pharmaceutically acceptable salt of said isolated peptide.

In some embodiments the therapeutic kit as herein defined further comprises instructions for use.

In some embodiments the therapeutic kit as herein disclosed is for use in a method of treating cancer, wherein said anti-cancer agent is administered at a dose lower than the standard of care dose of said anti-cancer agent.

The present disclosure further provides a method of treatment of cancer in a patient in need thereof, comprising administering to said patient a therapeutically effective amount of an isolated peptide comprising the amino acid sequence denoted by SEQ ID NO. 1 a functional derivative thereof or a pharmaceutically acceptable salt of said isolated peptide in combination with an anti-cancer agent, wherein said isolated peptide reduces the standard of care administered dose of said anti-cancer age.

The term "about" as used herein indicates values that may deviate up to 1%, more specifically 5%, more specifically 10%, more specifically 15%, and in some cases up to 20% higher or lower than the value referred to, the deviation range including integer values, and, if applicable, non-integer values as well, constituting a continuous range.

Disclosed and described, it is to be understood that this invention is not limited to the particular examples, methods steps, and compositions disclosed herein as such methods steps and compositions may vary somewhat. It is also to be understood that the terminology used herein is used for the purpose of describing particular embodiments only and not intended to be limiting since the scope of the present invention will be limited only by the appended claims and equivalents thereof.

The terms "comprises", "comprising", "includes", "including", "having" and their conjugates mean "including but not limited to". This term encompasses the terms "consisting of" and "consisting essentially of". The phrase "consisting essentially of" means that the composition or method may include additional ingredients and/or steps, but only if the additional ingredients and/or steps do not materially alter the basic and novel characteristics of the claimed composition or method. Throughout this specification and the Examples and claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

It must be noted that, as used in this specification and the appended claims, the singular forms "a", "an" and "the" include plural referents unless the content clearly dictates otherwise.

Throughout this specification and the Examples and claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

The following examples are representative of techniques employed by the inventors in carrying out aspects of the present invention. It should be appreciated that while these techniques are exemplary of preferred embodiments for the practice of the invention, those of skill in the art, in light of the present disclosure, will recognize that numerous modifications can be made without departing from the spirit and intended scope of the invention.

EXAMPLES

Without further elaboration, it is believed that one skilled in the art can, using the preceding description, utilize the present invention to its fullest extent. The following preferred specific embodiments are, therefore, to be construed as merely illustrative, and not limitative of the claimed invention in any way.

Standard molecular biology protocols which are known in the art and not specifically described herein are generally followed as in Sambrook & Russell, 2001.

Experimental Procedures

Biopsy
  Biopsies were obtained from patients by procedures well known in the art, by a skilled physician.
BiP Staining of Tissues Obtained by Biopsy
Solutions and Reagents
  Xylene (Sigma #534056);
  Ethanol, anhydrous denatured, histological grade (100% Solufix #E003 and 95% Sigma #32294);
  Deionized water (dH$_2$O);
  Hematoxylin Gill2 (Sigma #GHS216);
  Wash Buffer: 1×TBS/0.1% Tween-20 (1×TBST): For preparation of 1 L, 50 ml 20×TBS (Amresco #J640) were added to 950 ml dH$_2$O, 1 ml Tween-20 (Amresco #J640) was added and the buffer was mixed;
  Antibody Diluent: SignalStain® Antibody Diluent #8112;
  Antigen Unmasking:
    Citrate: 10 mM Sodium Citrate Buffer: For the preparation of 1 L, 2.94 gr sodium citrate trisodium salt dihydrate (C$_6$H$_5$Na$_3$O$_7$.2H$_2$O) were added to 1 L dH$_2$O. pH was adjusted to 6.0.
    TE: 10 mM Tris/1 mM EDTA, pH 9.0: For the preparation of 1 L, 1.21 gr Trizma® base (C$_4$H$_{11}$NO$_3$) and 0.372 g EDTA were added to 1 L dH$_2$O.
  3% Hydrogen Peroxide: For the preparation of 100 mL solution, 10 ml 30% H$_2$O$_2$ (Sigma #216763) were added to 90 ml dH$_2$O;
  Blocking Solution: Background Buster (Innovex #NB306);
  Primary antibody: Anti BiP antibody for Immunohistochemistry (Anti-BIP ab21685, abcam);
  Biotinylated secondary antibody: SignalStain® Boost Immunohistochemistry (IHC) Detection Reagent (HRP, Rabbit) #8114;
  DAB Reagent (Sigma #D6190);
  Eukitt Mounting Media (Sigma #03989);
Deparaffinization/Rehydration
  Slides were not allowed to dry at any time during this procedure. Sections of biopsy tissues were prepared as known in the art and were deparaffinized/hydrated as follows: sections were incubated in three washes of xylene for 5 minutes each, further incubated in two washes of 100% ethanol for 10 minutes each, next incubated in two washes of 95% ethanol for 10 minutes each and finally sections were washed twice in dH$_2$O for 5 minutes each.
Antigen Unmasking
  For Citrate, Slides were boiled in 10 mM sodium citrate buffer pH 6.0, then maintained at a sub-boiling temperature for 10 minutes. Slides were cooled on the bench top for 30 minutes. For Tris EDTA (TE), slides were boiled in 10 mM TE/1 mM EDTA, pH 9.0 then maintained at a sub-boiling temperature for 18 minutes. Slides were cooled on the bench for 30 minutes.

Staining

Sections were washed in dH$_2$O three times for 5 minutes each, incubated in 3% hydrogen peroxide for 10 minutes, washed in dH$_2$O twice for 5 minutes each and washed in wash buffer for 5 minutes. Then, each one of the sections was blocked with 100-400 µl blocking solution for 30 minutes at room temperature. The Blocking solution was removed and 100-400 µl primary antibody (namely anti-BiP) diluted 1:500 in antibody diluent was added to each one of the sections. The treated sections were incubated overnight at 4° C. Next, the antibody solution was removed and the sections were washed in wash buffer three times for 5 minutes each. Biotinylated secondary antibody (100-400 µl) was added to each one of the sections and the treated sections were incubated 30 minutes at room temperature in the presence of the secondary antibody. Then, the secondary antibody solution was removed and the sections were washed three times with wash buffer for 5 minutes each. Next, the reagent 3,3'-diaminobenzidine (DAB, 100-400 µl) was added to each one of the sections and the staining was monitored closely. As soon as the sections developed, slides were immersed in dH$_2$O. Sections were optionally counterstained in hematoxylin per manufacturer's instructions and then washed in dH$_2$O two times for 5 minutes each.

Dehydration of Sections

Sections were incubated in 95% ethanol two times for 10 seconds each, the incubation was repeated in 100% ethanol, incubating sections two times for 10 seconds each. The incubation was then repeated in xylene, incubating sections two times for 10 seconds each and then the coverslips were mounted for analysis.

Preparation of the dTCApFs Peptide and Composition Comprising Thereof

The peptide dTCApFs or NEROFE™ (both terms are used herein interchangeably and refer to the same peptide as indicated above) is a 14 amino acid residues long peptide, in which all of the amino acid residues are at their D configuration, having the amino acid sequence of Trp Trp Thr Phe Phe Leu Pro Ser Thr Leu Trp Glu Arg Lys (or WWTFFLP-STLWERK in a single letter code, as denoted by SEQ ID NO: 1).

The peptide was synthesized as follows. dTCApFs Acetate, the final drug product for use in clinical studies, was manufactured, packaged, tested, labeled and released under Good Manufacturing Practices (GMP) by Nextar Ltd., Israel.

dTCApFs powder for solution for injection was supplied either as a lyophilized 5 mL vial containing 15 mg (at a concentration of 7.5 mg/mL) or 10 mL vial containing 80 mg (at a concentration of 40 mg/mL) of the active substance with 4.8% mannitol, for reconstitution to a final volume of 2 mL with water for injection (WFI), per vial.

The reconstituted 2 mL vial of dTCApFs powder for solution for injection must thereafter be diluted to a final volume of 100 or 250 mL in aqueous Dextrose 5% for infusion. dTCApFs was supplied by Nextar Ltd for the designated clinical site for use in a phase one clinical study.

The drug product is a white sterile, non-pyrogenic lyophilized cake for single reconstitution in water for injection. Following reconstitution, it has the appearance of clear, colorless solution. Vials are type I clear injection glass 5 mL or 10 mL vials, stoppered with 20 mm lyophilization type rubber stoppers, with a 20 mm aluminum flip-off cap. Each ten vials are secondary packaged in a white, labeled outer box. Vial and secondary packaging box clinical study GCP standard labeling is performed under controlled conditions by Nextar Ltd.

On-Going Clinical Trial Outline

Patients

The study included adults patients (≥18 years) with pathologically confirmed locally advanced and/or metastatic solid malignancies, who failed or could not tolerate previous standard therapy. Key inclusion criteria included evaluable/measurable disease and Eastern Cooperative Oncology Group (ECOG) performance status (PS)≤1. Patients with liver cancer/hepatic metastases were eligible if liver function met certain criteria, and patients with brain metastases were eligible if radiation therapy was completed ≥4 weeks prior to enrollment and the patient received ≤4 mg/day of dexamethasone. Key exclusion criteria included receiving anti-cancer treatment 14 days prior to initiation of study drug and life expectancy of <16 weeks. Patients characteristics are summarized in Table 1 below.

TABLE 1

Patients demographics and baseline characteristics

| | dTCApFs dose | | | | |
|---|---|---|---|---|---|
| | 6 mg/m$^2$ n = 3 | 12 mg/m$^2$ n = 3 | 24 mg/m$^2$ n = 3 | 48 mg/m$^2$ n = 3 | 96 mg/m$^2$ n = 3 |
| Age, years | | | | | |
| Median (range) | 63 (62-77) | 61 (58-62) | 65 (57-67) | 72 (51-94) | 64 (55-77) |
| Mean (SE) | 68 (5) | 67 (4) | 67 (2) | 72 (8) | 64 (9) |
| Gender, male/female, n/n | 3/0 | 2/1 | 1/2 | 2/1 | 3/2 |
| Tumor, type, n | | | | | |
| Colorectal | 3 | 2 | 0 | 2 | 1 |
| Pancreatic | 0 | 0 | 1 | 0 | 4 |
| Other[a] | 0 | 1 | 2 | 1 | 0 |
| Prior therapies, n | | | | | |
| Chemotherapy | 3 | 4 | 4 | 1 | 3 |
| Radiotherapy | 1 | 2 | 1 | 1 | 0 |
| Surgery | 2 | 2 | 1 | 1 | 2 |
| Treatment with biological agents | 0 | 0 | 1 | 0 | 0 |
| Treatment with small molecules such as tyrosine kinase inhibitors | 0 | 0 | 0 | 1 | 0 |

[a]Includes neoplasms in the small intestine, lung, liver, and spinal cord.

Study Design

The present clinical study is a formal open label phase I dose escalation study. The primary objective was to determine the maximum tolerated dose (MTD) and safety profile of dTCApFs. Assessments included drug exposure, adverse events (AEs; graded according to the Common Terminology Criteria for Adverse Events (CTCAE), and characterization of dose-limiting toxicities (DLTs). Other objectives included assessment of serum levels of angiogenic factors after dTCApFs administration, pharmacokinetics (PK) and pharmacodynamics (PD) analyses, as well as assessment of receptor staining and tumor response.

The dose escalation study followed a traditional "3+3" scheme and included doses of 6, 12, 24, 48, and 96 mg/m$^2$ intravenous (i.v.) dTCApFs, 3 times/week in consecutive 28-day cycles. Patients' assignments are presented in FIG. 1. In all 3-patient cohorts, there were 2-4 weeks between the first dose for the first and second patients, and ≥1 week for the third patient. New dose levels started after follow up of ≥28 days for 3 patients at the previous level. MTD was defined as the highest dose level at which ≥1 of 3 subjects experience a DLT during their first cycle of treatment. Patients who did not complete their first cycle of treatment for reasons unrelated to AEs were replaced. In addition, PK parameters, including area under the curve (AUC), maximal plasma concentration (Cmax), and plasma half-life (t½) were determined. PK parameters were estimated using non-compartmental models.

In other words patients were administered i.v. with dTCApFs at 6 mg/m$^2$, 3 times per week, as long as their disease was not progressing. If a dose of 12 mg/m$^2$ was proven to be safe and the disease was progressing then the patient was administered with 12 mg/m$^2$. For example, patient number 1 in FIG. 1 was administered with two cycles of treatment (at 6 and 12 mg/m$^2$ dTCApFs). Patient number 4 in FIG. 1 received three cycles of treatment (at 12, 24 and 48 mg/m$^2$ dTCApFs).

Clinical activity of dTCApFs was assessed every 8 weeks by physical examination, computed tomography (CT), or magnetic resonance imaging (MRI) techniques (for evaluable disease only), using RECIST v1.1; and, where appropriate, informative tumor markers every cycle. This study was approved by the institutional review board of Rabin Medical Center, and the Ministry of Health, Israel and conducted at the Davidoff Center, Rabin Medical Center in accordance with the Declaration of Helsinki. All patients signed an informed consent before enrollment. The study was registered at ClinicalTrials.gov (NCT01690741).

Administration dTCApFs powder for solution for injection is supplied as a lyophilized 5 mL vial containing either 15 mg (7.5 mg/mL) or 10 mL vial containing 80 mg (40 mg/mL) of the active substance with 4.8% mannitol, for reconstitution to a final volume of 2 mL with water for injection per vial as described above. The reconstituted 2 mL vial of dTCApFs powder for solution for injection must thereafter be diluted to a final volume 100 mL in aqueous Dextrose 5% for infusion for dose levels up to and including 48 mg/m2. For dose levels above 48 mg/m2, the final dilution volume was 250 mL. dTCApFs for injection was administered intravenously (iv) during 60 minutes.

Pharmacokinetic Analyses

PK parameters, including AUC(0-24), Cmax, Cmin, Tmax and $t_{1/2}$ are estimated using non-compartmental models. Comparisons across dose levels are made to assess proportionality. A summary of the PK parameters is provided in Table 2 below.

TABLE 2

Pharmacokinetics of dTCApFs on the first day of cycles 1 and 2 (each cycle was 28 days).

| | dTCApFs dose | | | | |
|---|---|---|---|---|---|
| | 6 mg/m$^2$ n = 3 | 12 mg/m$^2$ n = 4 | 24 mg/m$^2$ n = 4 | 48 mg/m$^2$ n = 4 | 96 mg/m$^2$ n = 3 |
| | Cycle 1, Day 1 | | | | |
| AUC$_0$, ng · h/mL | 3813 | 12,905 | 49,630 | 79,935 | 206,742 |
| C$_{max}$, ng/mL | 1209 | 6048 | 14,609 | 18,267 | 32,964 |
| T$_{1/2}$, h | 2.3 | 2.1 | 3.2 | 4.9 | 6.0 |
| | Cycle 2, Day 1 | | | | |
| AUC$_0$, ng · h/mL | 9719 | 11,452 | 57,069 | 100,093 | 294,682 |
| C$_{max}$, ng/mL | 1536 | 6048 | 14,609 | 22,113 | 32,016 |
| T$_{1/2}$, h | 2.8 | 2.0 | 3.7 | 4.6 | 8.5 |

Pharmacodynamic Analyses

Changes from baseline in the levels of circulating cytokine and soluble T1/ST2 receptor and peripheral blood mononuclear cell (PBMC) T1/ST2 receptor expression are presented for interpretation and correlated with PK and antitumor activity analyses. If pretreatment and/or on-treatment tumor tissue samples are obtained, results of T1/ST2 receptors assays are presented for clinical interpretation.

Biomarker Analysis

Blood samples were collected from patients and placed on ice for 10 minutes on a regular basis as described below. Serum was collected by centrifuging at 3000 rpm for 10 minutes at 4° C., was kept in a separate vial at ≤−20° C., and shipped to Immune System Key Ltd at −20° C., where they were thawed, aliquoted, and stored at ≤−20° C. Repeated freeze-thaw cycles were avoided.

Immunohistochemistry (IHC) staining was performed for T1/ST2 receptor using a full length anti-ST2 antibody (GenMed, Plymouth, Minn.). Serum levels of various factors were measured with enzyme-linked immunosorbent assay (ELISA). Additional factors that were measured included: Vascular endothelial growth factor (VEGF), Vascular endothelial growth factor D (VEGF-D), epidermal growth factor (EGF), angiopoietin-1, fibroblast growth factor 1 (FGF-1), fibroblast growth factor 2 (FGF-2), platelet-derived growth factor AA (PDGF-AA), platelet-derived growth factor BB (PDGF-BB), transforming growth factor β1 (TGF-β1) (all using ELISA kits by R&D systems, Abingdon, UK); granulocyte-macrophage colony-stimulating factor (GM-CSF), interleukin 2 (IL-2), interleukin 12p70 (IL-12p70), interleukin 21 (IL-21) and tumor necrosis factor α (TNF-α) (Millipore, Billerica, Mass.); and glucose regulated protein 78 (GRP78)/BiP (Enzo, New York, N.Y.). A summary of serum levels of various angiogenic factors and cytokines measured in patients undergoing treatment with the peptide is presented in Table 3 below.

TABLE 3

Mean change in serum levels of angiogenetic factors and cytokines with dTCApFs administration

| | dTCApFs dose | | | | |
|---|---|---|---|---|---|
| | 6 mg/m² n = 3 | 12 Mg/m² n = 3 | 24 Mg/m² n = 3 | 48 Mg/m² n = 3 | 96 Mg/m² n = 5 |
| | Change in serum level from pre- to post- treatment with dTCApFs, % | | | | |
| Angiogenic factors | | | | | |
| Angioeitin-1 | +960 | −80 | −77 | −50 | +70 |
| FGF-1 | +120 | −62 | −20 | −27 | +457 |
| FGF-2 | +199 | −74 | −34 | −13 | +44 |
| PDGF-AA | +1379 | −92 | −79 | −73 | +57 |
| PDGF-BB | +2271 | −95 | −82 | −78 | +185 |
| VEGF-A | +265 | −47 | −62 | −72 | −2 |
| TGF-β1 | +18 | −80 | −59 | −20 | No data |
| VEGF-D | +117 | −40 | −54 | −63 | +3 |
| Cytokines | | | | | |
| GM-CSF | +2173 | −97 | +11 | +5613 | +974 |
| IL12-p70 | +469 | −76 | +83 | +477 | +332 |
| Il-2 | No data | −100 | No data | +242 | +577 |
| Il-21 | +100 | −61 | +84 | +1326 | +29 |
| TNF-α | +4 | −5 | +31 | +74 | +97 |

FGF, fibroblast growth factor; GM-CSF, granulocyte-macrophage colony-stimulating factor; IL, interleukin, PDGF, platelet-derived growth factor; TGF, transforming growth factor; VEGF, vascular endothelial growth factor; TNF, tumor necrosis factor.

Immunogenicity

Changes from baseline in the levels of circulating anti-dTCApFs antibodies are presented for interpretation.

Antitumor Activity Analyses

Subjects with evaluable or measurable disease are assessed according to the response evaluation criteria in solid tumors (RECIST) version 1.1 every 2 cycles, where a cycle is defined as 4 weeks of treatment with three administrations per week. Tumor lesion measurements and changes from baseline are summarized by cycle and dose cohort. A summary of the adverse events by dTCApFs dose group is provided in Table 4 below.

TABLE 4

Summary of adverse event by dTCApFs dose group

| | dTCApFs dose | | | | |
|---|---|---|---|---|---|
| | 6 mg/m² n = 3 | 12 mg/m² n = 3 | 24 mg/m² n = 3 | 48 mg/m² n = 3 | 96 mg/m² n = 5 |
| Grade 1 | | | | | |
| Blood disorders | | | | | |
| Anemia | 3 | 0 | 0 | 0 | 0 |
| Increased INR | 0 | 0 | 0 | 1 | 0 |
| GI disorders | | | | | |
| Abdominal pain | 0 | 1 | 2 | 0 | 0 |
| Bowel obstruction | 1 | 0 | 0 | 0 | 0 |
| Diarrhea | 0 | 2 | 0 | 0 | 2 |
| GI hemorrhage | 1 | 0 | 0 | 0 | 0 |
| Vomiting | 2 | 0 | 0 | 0 | 1 |
| Genera disorders | | | | | |
| Dehydration | 0 | 0 | 0 | 0 | 1 |
| Fatigue | 0 | 1 | 0 | 1 | 0 |
| Hypertension | 3 | 1 | 1 | 0 | 1 |

TABLE 4-continued

Summary of adverse event by dTCApFs dose group

| | dTCApFs dose | | | | |
|---|---|---|---|---|---|
| | 6 mg/m² n = 3 | 12 mg/m² n = 3 | 24 mg/m² n = 3 | 48 mg/m² n = 3 | 96 mg/m² n = 5 |
| Nervous system disorders | | | | | |
| Neuropathy Grade 2 | 0 | 1 | 1 | 0 | 0 |
| Pain | | | | | |
| Pain, leg | 0 | 2 | 0 | 0 | 0 |
| Pain, upper back | 0 | 0 | 0 | 0 | 1 |
| Respiratory system disorders | | | | | |
| Cough | 0 | 1 | 0 | 0 | 0 |
| Skin disorders | | | | | |
| Pruritus | 0 | 0 | 0 | 0 | 1 |
| Urticaria | 0 | 0 | 0 | 0 | 2 |
| Hepatic and urinary disorders | | | | | |
| ALT increase | 0 | 0 | 0 | 0 | 1 |
| AST increase | 0 | 0 | 0 | 0 | 1 |
| Bilirubin increase | 0 | 0 | 0 | 1 | 1 |
| Liver dysfunction | 0 | 0 | 0 | 0 | 1 |
| Urinary tract infection Grade 3 | 0 | 1 | 0 | 0 | 0 |
| Blood disorders | | | | | |
| Increased INR | 0 | 0 | 0 | 1 | 0 |
| General disorders | | | | | |
| Hypertension | 2 | 1 | 1 | 0 | 2 |
| Hepatic and urinary disorders | | | | | |
| Bilirubin increase | 0 | 0 | 0 | 1 | 1 |
| GI disorders | | | | | |
| Bowel obstruction | 1 | 0 | 0 | 0 | 0 |
| Diarrhea | 0 | 1 | 0 | 0 | 1 |
| GI hemorrhage Grade 4 | 1 | 0 | 0 | 0 | 0 |
| GI disorders | | | | | |
| Vomiting | 0 | 0 | 0 | 0 | 1 |

ALT, alanine transaminase; AST, aspartate aminotransferase; GI, gastrointestinal; INR, international normalized ratio.

Objective tumor response rates (complete response and partial response), duration of objective tumor response, time to objective tumor response, and progression-free survival are presented. Time-to-event estimates and survival curves are generated using the Kaplan-Meier method and Cox model with calculated crude Hazard ratio and calculated adjusted Hazard ratio (adjusted for confounder variables). Subjects with informative tumor marker assessments (eg, CA125 or PSA) undergo appropriate assessments every cycle. Tumor marker parameters, when evaluable, are summarized by cycle and dose cohort. An exploratory evaluation of the relationship between PK, PD and clinical effects of dTCApFs is performed. A summary of the progression-free survival (PFS) of patients enrolled in the study is presented in Table 5 below.

TABLE 5

PFS on the last regimen before enrolling the study and on dTCApFs. Greyed rows represent patients who experienced PFS on dTCApFs which was comparable or exceeded that of their last regimen pre enrollment.

| Patient no. | PFS on the last regimen pre enrollment, days | PFS on dTCApFs, days |
|---|---|---|
| 1 | 480 | 53 |
| 2 | 134 | 25 |
| 3 | 110 | 170 |
| 4 | 0 | 330 |
| 5 | 52 | 51 |
| 6 | 384 | 110 |
| 7 | 54 | 90 |
| 8 | 80 | 52 |
| 9 | 375 | 60 |
| 10 | 1800 | 14 |

TABLE 5-continued

PFS on the last regimen before enrolling the study
and on dTCApFs. Greyed rows represent patients who
experienced PFS on dTCApFs which was comparable or
exceeded that of their last regimen pre enrollment.

| Patient no. | PFS on the last regimen pre enrollment, days | PFS on dTCApFs, days |
|---|---|---|
| 11 | 41 | 52 |
| 12 | 42 | 50 |
| 13 | 96 | 42 |
| 14 | 365 | 40 |
| 15 | 1 | 80 |
| 16 | 105 | 45 |
| 17 | 564 | 41 |

PFS, progression-free survival

Statistical Analysis

Descriptive statistics were used for all analyses and were performed with SAS® version 9.1 (SAS Institute Inc., Cary, N.C.). Regression analysis was used to study 2-way correlation between tumor change per month, administered doses of dTCApF, and levels of the ER-stress biomarker (BiP). The statistical significance of the correlation was validated using F-statistics.

Determination of the GRP78/Bip Marker Blood Level by ELISA

Determination of the plasma level of BiP in patients undergoing treatment by the dTCApFs peptide was performed as follows.

Samples Collection

Blood was collected from patients treated with dTCApFs in lavender top vacutainer tubes, then placed on ice for 10 minutes. Then the vacutainer was centrifuged at 3000 rpm for 10 minutes at 4° C. The plasma fraction was collected onto a separate vial and kept at ≤−20° C. until shipped to the R&D department with World Courier at −20° C. When received, serum samples were thawed, aliquot of 56 μl were made in 0.5 ml vials and stored at ≤−20° C. Repeated freeze-thaw cycles were avoided. Blood was collected on days 1, 15 and 29 of the first cycle and on day 29 of the subsequent cycles.

Determination of Blood Levels of GRP78/BIP

Determination of blood levels of GRP78/BIP was performed using the kit GRP/BIP ELISA kit (cat #ADI-900-214 Enzo. Aliquots of plasma samples were thawed at 4° C. and centrifuged at 10,000 G for 6 minutes at 4° C. The samples were then diluted 1:5 with Tris buffered saline containing BSA and detergents (kit assay) buffer. The samples were then loaded in duplicates onto the provided 96 well plate, which were pre-coated with donkey anti-sheep IgG. Calibration samples and blank samples were also loaded onto the plate, and then the antibody directed to BiP (yellow) was added to all of the wells, except the blank ones. The ELISA plate was sealed and incubated at room temperature (RT) with shaking at 750 rounds per minute (RPM) for 1 hour.

After the above incubation period the plate was not washed and BiP conjugate (blue) was added to all of the wells except the blank ones. The plate was incubated with shaking for 1 additional hour (RT).

After the additional incubation period, the wells content was aspirated and the wells were washed using an automated wash (Bio-plex pro II Wash station) by adding 300 μl Tris buffered saline containing detergents (the kit's wash buffer) to every well. The washing procedure was repeated three more times for a total of four washes. After the final wash, the wells were aspirated and the plate was tapped firmly upside down on a lint free paper towel to remove any residual wash buffer.

3,3',5,5'-Tetramethylbenzidine (TMB) solution was added into each well, and the plate was sealed and incubated for 19 minutes at RT in the dark with shaking. Stop solution was then added into each well, delta OD was read at 450 nm/570 nm. Blank wells values were subtracted from all results. Calibration curve was created and BiP ng/ml values were calculated accordingly and multiplied with dilution factor (×5).

Calculating the Difference in Plasma BiP Expression Level

The difference in the plasma expression level of BiP was determined by calculating the difference between BiP expression level measured in the plasma of a patient treated with dTCApFs on day 29 of treatment and BiP expression level measured in the plasma of a patient treated with dTCApFs on day 1 of treatment (prior to the first administration of the dTCApFs peptide) and by dividing the result by the above BiP expression level measured on day 1 of treatment (normalizing), namely as follows: [(BiP level at day 29)−(BiP level at day 1)]*100/(BiP level at day 1).

Determination of Calreticulin (CRT) Blood Level

Serum CRT levels were determined using the kit Elisa CRT kit (human) (OKEH01054, Aviva system Biology). Patients' samples from days 1 and 15 or 29 of cycle 1 (C1D1, C1D15 and C1D29) were thawed and centrifuged at 10 minutes at 10,000 G and loaded onto the plate according to the manufacturer's protocol.

Determination of Tumor Size

Tumor size was evaluated at the medical site according to the Response Evaluation Criteria in Solid Tumors (RECIST) guidelines (for example by performing a computerized tomography scan (CT)). The tumor size on the last day of the trial (namely after the last administration of the peptide) was compared to the tumor size on the first day of the trial (prior to the first administration of the peptide), in percentage.

Evaluation of the ST2 Status in Cancer Cells

The ST2 status in cancer cells was evaluated for biopsy samples obtained from patients by immunohistochemistry, using specific anti-human st2 receptor antibody. Following the staining step the biopsy was evaluated by a pathologist.

ImmunoCytoChemistry (ICC) of OV90 Cells Treated with dTCApFs

Materials for Cell Culture Growth and Treatment

Growing Media:
  DMEM high glucose, L-Glutamine (Gibco 41965-039);
  Sodium Pyruvate 11.0 mg/ml (100 mM) (Biological industries cat No. 03-042-1B);
  50 ml FBS (Biological industries cat no. 04-121-1A);
  0.5 ml Amphotericin B 2500 μg/ml (Biological industries cat no. 03-029-1);
  5 ml Gentamycin sulfate 50 mg/ml (Biological industries cat no. 03-035-1);

Treatment Media:
Treatment media was based on the growing media supplemented with 5% Mannitol (Sigma cat no. M4125-500 G). Media was filtered in 0.2 μm filter after adding Mannitol.

Additional Materials:
  Trypsin EDTA (Biological industries cat no. 03-052-1B);
  75 cm² culture Flasks (Nunc cat no. 178905);
  25 cm² culture Flasks (Nunc cat no. 136196);
  20 mg/ml dTCApFs in Mannitol (use aliquots, avoid repeated freeze-thaw cycle);
  human ovarian cancer cell lines OV90 were used: Regular OV90 (American type collection, ATCC) and T1/ST2 KO OV90 (manufactured by the inventors);

Materials for ICC:
  Slides: Nunc™ Lab-Tek™ II Chamber Slide System (154534 Nunc);
  Washing Buffer: PBS (02-023-5A Biological Industries);
  Fixing Solution: 3% Formaldehyde (252549 Sigma) in PBS;
  Permeabilization Solution: 0.25% Triton X-100 (0694 Amresco) in PBS;
  Blocking buffer: 1% BSA (A7906 Sigma), 22.52 mg/mL glycine(G8898-500 G Sigma) in PBS with 0.1% Tween-20 (0777 Amresco);
  Antibody buffer: 1% BSA (A7906 Sigma) in PBS with 0.1% Tween-20 (0777 Amresco);
  Primary antibodies: anti-58k Golgi marker (ab27043) diluted 1:500, anti-β-COP (ab6323) diluted 1:250, anti-GRP78 BiP (ab21685) diluted 1:1,000 (antibodies were purchased from Abcam);
  Secondary antibody: For 58k Golgi marker and β-COP: ZytoChem Plus (HRP) Polymer anti-Rabbit (ZUC032-006). For BIP: ZytoChem Plus (HRP) Polymer anti-Mouse (ZUC050-006);
  DAB (3,3'-Diaminobenzidine tetrahydrochloride, D3939 Sigma);
  Aqueous Mounting Medium (ab128982 Abcam).

Cell Culture Growth

OV90 and OV90 ST2 KO cells were grown in flasks in an incubator at 37° C., 5% $CO_2$ and 100% humidity until up to 70-80% density was reached. The medium was emptied from the flasks using a pipette. Next, 4 ml Trypsin EDTA was added to each flask and the flasks were placed in the incubator for few minutes until most of the cells were detached from the flasks. Tapping on the flasks to increase detaching of cells was avoided. Medium (10 ml) was then added to the flasks and cultures in medium and Trypsin were divided into 2 flasks, to each of which 15 ml fresh medium was added. The cells were incubated 2-3 days for growth until reaching 70-80% and the passage procedure was repeated as necessary.

Cell Treatment

Cell cultures grown as detailed above in medium and Trypsin were transferred into 50 ml conical tubes and the tubes were centrifuged at 300 g for 10 min in 4° C. Then the supernatant was discarded and 15 ml fresh medium was added to the cells pellet, in order to fluidize the pellet. The cells were counted and seeded at 10,000 cells/well on a chamber slide in 1 ml growing medium. The chamber slide were placed to rest in the hood for 1 hr then transferred to the incubator, overnight. The following day cell treatment medium was prepared comprising 50 µg/ml dTCApFs. The cells were treated by aspirating and discarding the medium from the chamber slides and by adding 0.5 ml cell treatment medium comprising dTCApFs (or control) to each well and then incubated for 48 hrs in the incubator. After that period an additional dose of treatment medium comprising dTCApFs was added to the treated cells wells and the cells were collected after further 24 hrs of incubation.

ImmunoCytoChemistry

Cells treated as detailed above were subjected to the following ICC protocol. After completing of the incubation period the medium was aspirated and the cells were washed by filling each well with washing buffer. Next, buffer was discarded and 300 µl Fixing solution were added to each well. Cells were incubated at RT for 15 minutes. The fixing solution was then discarded and wells were briefly rinsed twice. Next, 300 µl Permeabilization solution were added to each well and cells were incubated at RT for 10 minutes. The Permeabilization solution was discarded and wells were washed 3 times, 5 minutes for each wash. Blocking buffer (1 ml) was added to each well, and cells were incubated at RT for 1 hr. Before the end of the incubation time, the primary antibodies detailed above were diluted in antibody dilution buffer. Next, the blocking buffer was discarded from the wells and 120 µl primary antibody was added to each well. The cells were then covered with Parafilm (or duct tape) and incubated overnight at 4° C.

The next day, the primary antibody was discarded and the wells were washed three times with washing buffer, 5 minutes for each wash. The secondary antibody was then added to each well (1-2 drops) and the cell wells were incubated at RT for 30 min. Then the wells were washed 3 times with wash buffer, 5 minutes for each wash. DAB substrate (freshly prepared and filtered in 0.2 µm filter) was added to each well (1-2 drops) and the cell wells were incubated 5-15 minutes while checking development. The cell wells were washed with PBS for 5 minutes. The wells were then removed from the slide, and the slide was air dried. Mounting media was added and the slide was put on coverslip. Visualization was performed using a light microscope.

BrdU Incorporation Assay in the Presence of Taxol or dTCApFs

Human pancreatic cancer cells (BxPC3) and human ovarian cancer cells (OV90) were treated with dTCApFs or Taxol for 24 hours in the presence of BrdU, as detailed below.

Cells were placed at 2,000 cells/well in the middle of a 96 well plate with 100 µl DMEM (life science 41965-039) and 10% fetal calf serum (FBS, Biological industries 14-127-1A) for 24 hours in an incubator at 37° C. with 5% $CO_2$. The medium was then replaced to 200 µl DMEM with 2.5% FBS and Taxol (sigma T7402) at a final concentration of 2 nM or 4 nM in DMSO or dTCApFs (nextar ISK353-01 batch 351-01/1.68) at a final concentration of 25 µg/ml in DMSO. The medium in the control cells was replaced by DMEM and FBS as indicated above. The maximal concentration of DMSO in the cell wells was less than 0.5%. Four wells were used for each concentration.

Taxol- and dTCApFs-treated cells as well as the control cells were further incubated for 24 hours in the presence of BrdU as follows: 20 µl BrdU reagent (diluted 1:100 in DMEM supplemented with 2.5% FBS) was added to the cells and the plate was incubated 24 hours in 37° degrees incubator with 5% $CO_2$. BrdU ELISA was performed according to the kit protocol (Millipore #2752).

BrdU Incorporation Assay in the Presence of Taxol and dTCApFs

Human pancreatic cancer cells (BxPC3) and human ovarian cancer cells (OV90) were treated with dTCApFs and Taxol for 24 hr in the presence of BrdU, as detailed below.

Cells were placed at 2000 cells/well in the middle of a 96 well plate with 100 µl DMEM and 10% FBS for 24 hours in an incubator at 37° C. with 5% $CO_2$. The medium was then replaced to 200 µl DMEM with 2.5% FBS and dTCApFs at a final concentration of 25 µg/ml (nextar ISK353-01 batch 351-01/1.68) in DMSO. The maximal concentration of DMSO in the cells wells was less than 0.5%. Four wells were used for each concentration. Taxol at a final concentration of 2 nM or 4 nM (in 5 µl DMEM supplemented with 2.5% FBS) was then added to the cells containing dTCApFs and the treated cells were further incubated for 24 hours in the presence of BrdU as follows: 20 µl BrdU reagent diluted 1:100 in DMEM supplemented with 2.5% FBS were added to the cells 24 hours before the end of experiment. Finally, BrdU ELISA was performed according to kit protocol (Millipore #2752).

Example 1

The Peptide dTCApFs Increases Endoplasmic Reticulum (ER) Stress in Cancer Cells

As indicated above, a peptide termed "T101" that is encoded by a cDNA unique to the human thymus was identified and was reported, inter alia, to reduce cancer tumor size. In addition, a peptide derivative of T101, termed herein dTCApFs (or "Nerofe"), has been reported to decrease the secretion of proteins that are known to be associated with cancer metastasis by cancer cells and to directly inhibit migration of cancer cells in vitro (16).

As described above, an ongoing clinical trial is presently performed with the peptide dTCApFs. This peptide has the all D amino acid sequence of Trp Trp Thr Phe Phe Leu Pro Ser Thr Leu Trp Glu Arg Lys, as denoted by SEQ ID NO: 1 and was prepared as described above.

The peptide dTCApFs was administered to cancer patients as described above (Table 1) at the indicated dosing regimen, intravenously (iv), 3 times a week.

In order to investigate the effect of the dTCApFs peptide on cancer cells, biopsies were taken from a spinal cord tumor patient treated for 11 months with dTCApFs under the regimen described above. Tissue biopsies were obtained from the patient before treatment and after 11 months of treatment and were stained with anti-BiP antibody for detecting the level of BiP, a marker of endoplasmic reticulum (ER) stress.

As detailed above, the binding immunoglobulin protein (BiP), also known as GRP78, acts as a molecular chaperone in the ER and its synthesis is markedly induced under conditions that lead to the accumulation of unfolded polypeptides in the ER.

As shown in FIG. 2, a clear difference in the level of BiP was observed in a biopsy obtained from the patient before the treatment was initiated (FIG. 2A) and after 11 month of treatment (FIG. 2B), demonstrating that the dTCApFs peptide increased ER stress in tumors obtained from a spinal cord neoplasm cancer patient.

Example 2

An Increase in the ER Marker BiP Level Correlates with a Reduction in Tumor Size As detailed in Example 1 above, the dTCApFs peptide was shown to increase ER stress in tumor cells obtained from patients undergoing therapy with this peptide, based on the observed increase in the level of BiP. Surprisingly, the increase in the ER stress marker BiP was found to be in a high correlation with an inhibition of tumor growth in the treated patients, as detailed below.

The level of BiP was determined in the plasma of cancer patients participating in the clinical study using the dTCApFs peptide performed as detailed above on day 1 (prior to the first administration of dTCApFs) and on day 29 of treatment with dTCApFs. The plasma level of BiP obtained for a cancer patient on day 1 of treatment (the "baseline" level) was then subtracted from the plasma level of BiP obtained for the same cancer patient on day 29 of treatment.

In parallel, participating cancer patients were assessed for the size of their tumor using computerized tomography scan (CT), as described above, on day 1 (or just before initiation of treatment) and on last day of treatment. The difference in the tumor size (also referred to herein as "tumor change") was then calculated as described above. Briefly, the "tumor change" is a measure of the difference in tumor size obtained upon treatment by dTCApFs between the first day of treatment (day 1) to last day of treatment (duration of treatment was determined based on criteria such as mentioned above).

Overall, 39 patients were screened, of whom 17 enrolled and completed the study. The majority of patients (64%) were males, and the median (range) age was 65 (51-94) years. Almost half of the patients (47%) had colorectal (CRC) cancer and approximately a quarter (29%) had pancreatic cancer. All patients except one received several lines of anti-cancer therapy (e.g., chemotherapy, radiotherapy, biologic therapy) before enrolling (Table 1). The patients received 1-3 cycles of escalating dTCApFs doses (6 mg/m$^2$, 12 mg/m$^2$, 24 mg/m$^2$, 48 mg/m$^2$, and 96 mg/m$^2$) as detailed in FIG. 1.

As indicated above the serum levels of the GRP78/BiP protein (as an ER stress biomarker) was measured before initiation of dTCApFs treatment and after 29 days of treatment as indicated above. A statistically significant correlation was found between the administered dTCApFs doses and the change in serum GRP78/BiP levels ($P \leq 0.05$), as demonstrated in FIG. 3, as well as between changes in tumor size and changes in serum levels of GRP78/BiP ($P \leq 0.002$) (FIG. 4), suggesting that dTCApFs induced ER stress.

Figure 4:
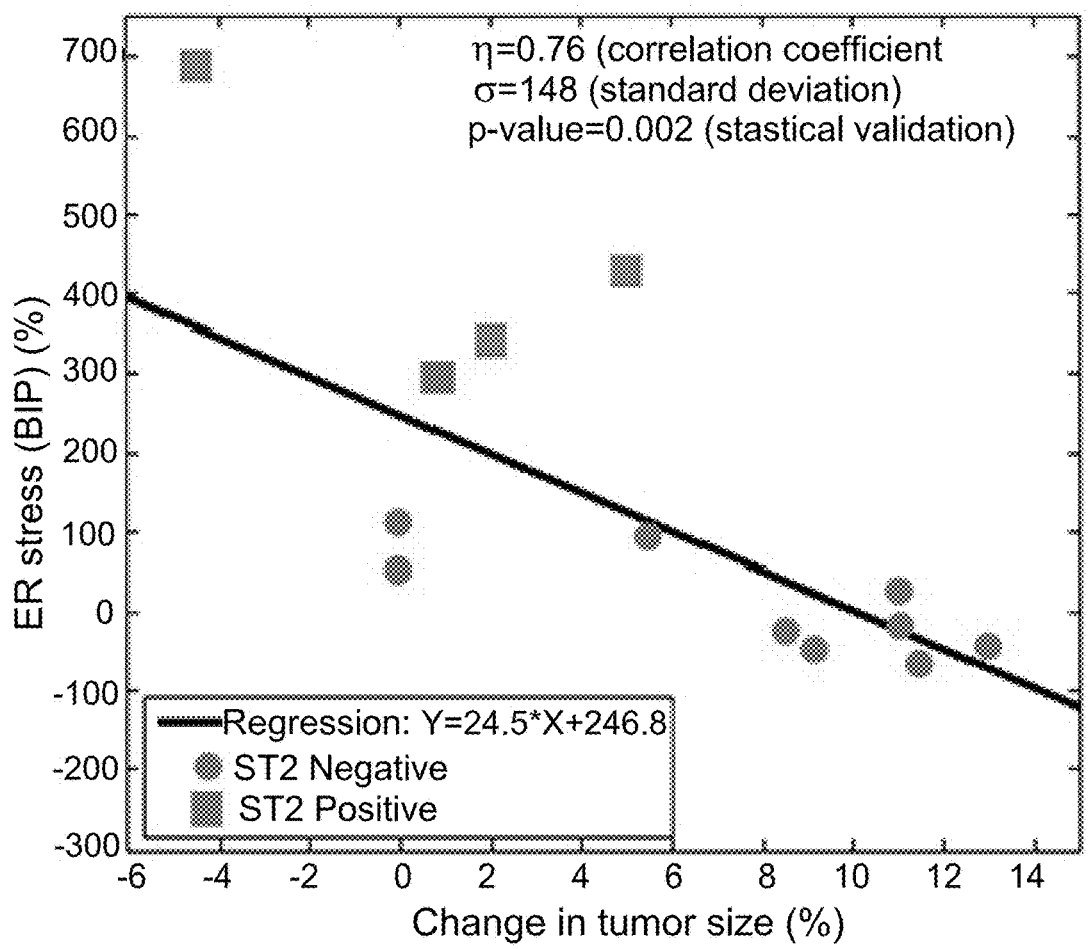
FIG. 4 is a graph showing the correlation between change in the serum level of the ER stress marker BiP and the change in tumor size.

As shown in FIG. 4, there was a (negative) linear correlation between the change in the level of BiP and the change in tumor size, namely, an increase in the level of BiP correlated with complete inhibition of tumor growth. These results demonstrate that dTCApFs acts inter alia by increasing the ER stress in cancer cells and without wishing to be bound by theory, via disrupting the Golgi complex, thereby leading to cancer cell death.

The serum levels of BiP in patients participating in the clinical trial determined at days 1 and 29 of treatment as described above are presented in Table 6 below.

TABLE 6

Serum levels of BiP in patients participating in the clinical trial

| Patient | Cohort | Cycle | Day | ng/ml BiP | stDev (log) |
|---------|--------|-------|-----|-----------|-------------|
| 002 | 1 | 1 | 1 | 21.30 | 0.06 |
| 002 | 1 | 1 | 29 | 26.94 | 2.74 |
| 006 | 2 | 1 | 1 | 9.85 | 6.75 |
| 006 | 2 | 1 | 29 | 38.91 | 3.00 |
| 007 | 2 | 1 | 1 | 51.03 | 2.77 |
| 007 | 2 | 1 | 29 | 38.68 | 0.64 |
| 011 | 2 | 1 | 1 | 45.78 | 1.01 |
| 011 | 2 | 1 | 29 | 23.89 | 0.44 |
| 012 | 3 | 1 | 1 | 13.81 | 0.55 |
| 012 | 3 | 1 | 29 | 21.17 | 0.23 |
| 013 | 3 | 1 | 1 | 48.33 | 0.31 |
| 013 | 3 | 1 | 29 | 26.94 | 3.55 |
| 015 | 3 | 1 | 1 | 56.53 | 2.25 |
| 015 | 3 | 1 | 29 | 46.62 | 1.16 |
| 017 | 4 | 1 | 1 | 86.18 | 0.24 |
| 017 | 4 | 1 | 29 | 27.94 | 0.15 |
| 022 | 5 | 1 | 1 | 22.90 | 0.15 |
| 022 | 5 | 1 | 29 | 48.62 | 1.25 |
| 023 | 5 | 1 | 1 | 20.67 | 0.65 |
| 023 | 5 | 1 | 29 | 39.86 | 0.11 |
| 035 | 5 | 1 | 1 | 38.44 | 0.46 |
| 035 | 5 | 1 | 29 | 169.21 | 0.47 |

Interestingly, as indicated in Table 3 above, treatment with dTCApFs at a dose of 6 mg/m$^2$ led to an increase in the serum levels of angiopoietin-1, FGF-1, FGF-2, PDGF-AA, PDGF-BB, VEGF-D, TGF-β, and VEGF. However, at doses of 12-48 mg/m², a decrease in the serum levels of these factors was observed, and at 96 mg/m², an increase in all factors except for VEGF-D was noted. Also, serum levels of all anti-cancer cytokines such as GM-CSF, IL2, IL-12p70, IL-21, and TNF-α increased with dTCApFs administration in all dose levels.

Figure 5:
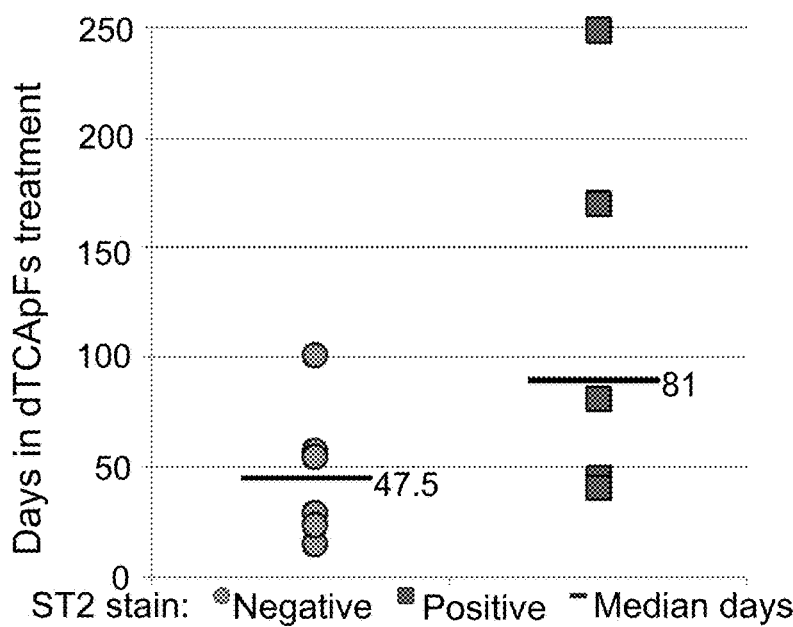
FIG. 5 is a graph showing the number of days of participation in the clinical trial for patients according to their T1/ST2 expression.

In order to explore the mode of activity (MOA) of dTCApFs, patients were examined by their T1/ST2 status. It was found that patients whose tumors were T1/ST2 positive (as determined by IHC) stayed in the trial longer than those whose tumors were T1/ST2 negative, as demonstrated in FIG. 5 and experienced stable disease (SD) during dTCApFs treatment.

The T1/ST2 receptor (also referred to herein as "ST2" and "ST2/T1") is a member of the Interleukin 1 receptors (IL-1R) superfamily. As known in the art, members of the interleukin-1 receptor (IL-1R) superfamily are characterized by extracellular immunoglobulin-like domains and intracellular Toll/Interleukin-1R (TIR) domain. Members of this family play important role in host defense, injury and stress. It has been previously reported that the thymus peptide T101, from which the peptide dTCApFs was derived, may serve as a ligand of the T1/ST2 receptor (13-15).

Therefore the levels of BiP were re-analyzed (namely the changes in tumor size vs administered dTCApFs dose) for each of the populations (T1/ST2-negative positive patients and T1/ST2-positive patients). The results are graphically presented in FIG. 6.

Figure 6:
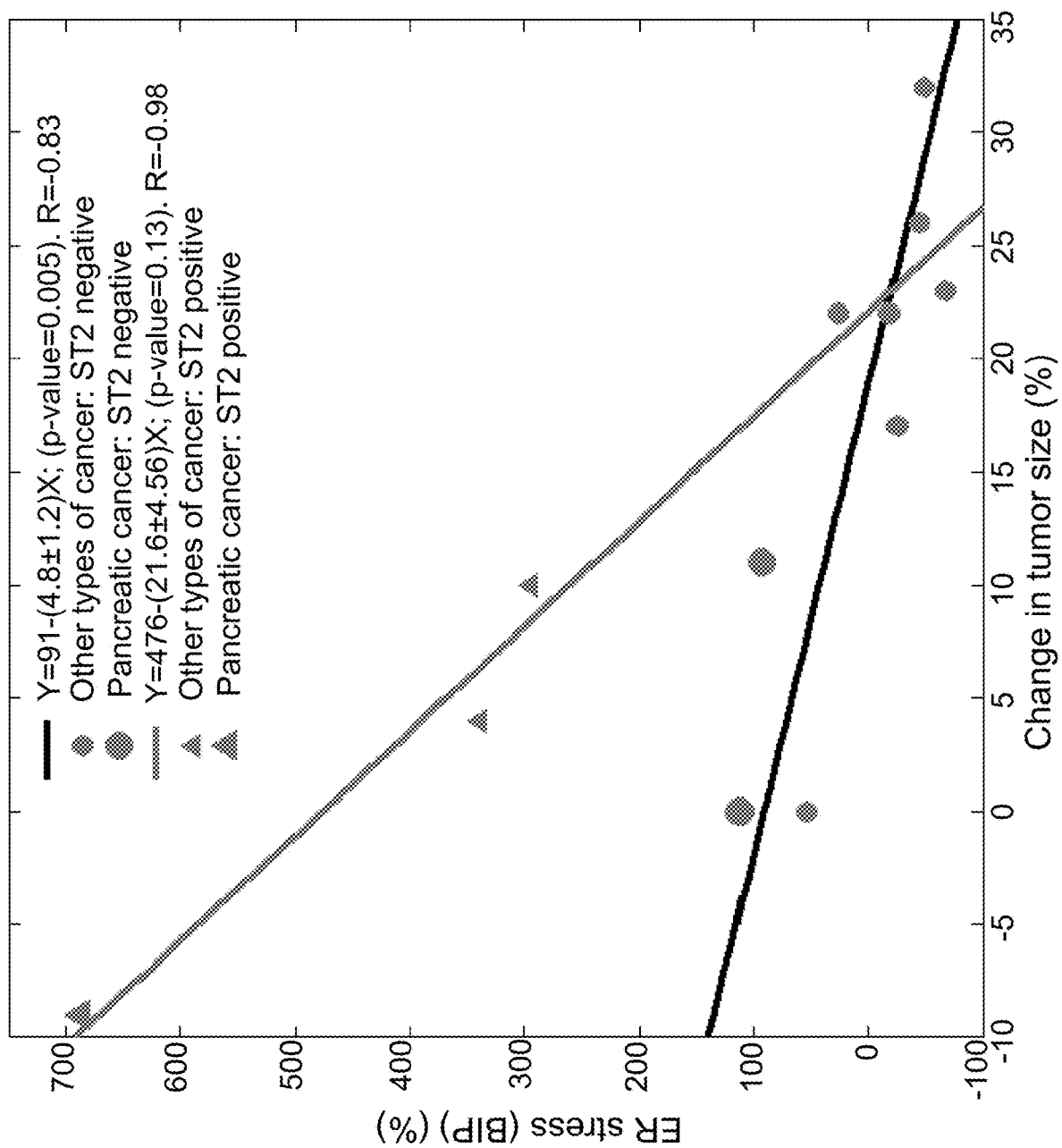
FIG. 6 is a graph showing the correlation between change in the serum level of the ER stress marker BiP and the change in tumor size for ST2 negative and ST2 positive populations.

As shown in FIG. 6, in which the ST2 positive and ST2 negative cancers were separated, correlating the BiP marker level to tumor change in cancer cells that were ST2 positive resulted in an R value of −0.98 and in cancer cells that were ST2 negative resulted in an R value of −0.83. The p-value of the ST2 positive graph is not optimal due to the small data set.

Without wishing to be bound by theory, this difference indicates that the higher abundance of the ST2 receptor on ST2 positive cells facilitates entry of the dTCApFs peptide into these cells, thus presumably requiring lower doses of the peptide.

It is noteworthy that even in cells defined as "ST2 negative" there is ample ST2 receptor for incorporating the dTCApFs peptide into the cells, albeit at a lower abundance than in the case of the ST2 positive cells.

The results presented above indicate that that the ER stress marker BiP may be used as a marker to the efficiency of the dTCApFs peptide in inhibiting tumor growth in cancer patients treated with this peptide. Since the effect is visible already at the first month of treatment, determining the level of BiP at an early stage of treatment may serve as an evaluation test or tool for assessment of treatment efficiency and to aid in determining further treatment steps for these patients, for example in determining whether treatment using dTCApFs should be continued.

Example 3

Safety and Tolerability of the Peptide dTCApFs

Various parameters were analyzed for patients participating in the clinical trial referred to in Example 2 above, including safety, PK and efficacy, as detailed below.

Safety and Tolerability

Mean number of treatment cycles per patients was 3.2±1.4. No dose-limiting toxicities (DLTs) were observed in any patient up to cohort 5. The adverse events (AEs) are summarized in Table 4 above. None were related to study drug. Hypertension, anemia, vomiting, diarrhea, and abdominal pain were the most reported grade 2 AEs, and hypertension was the most reported grade 3 AE. Vomiting was the only grade 4 AE, reported in 1 patient. Most of the AEs were self-resolved. Overall, treatment with dTCApFs was well-tolerated with no cumulative toxicity. MTD was not reached.

Pharmacokinetics

Figure 7:
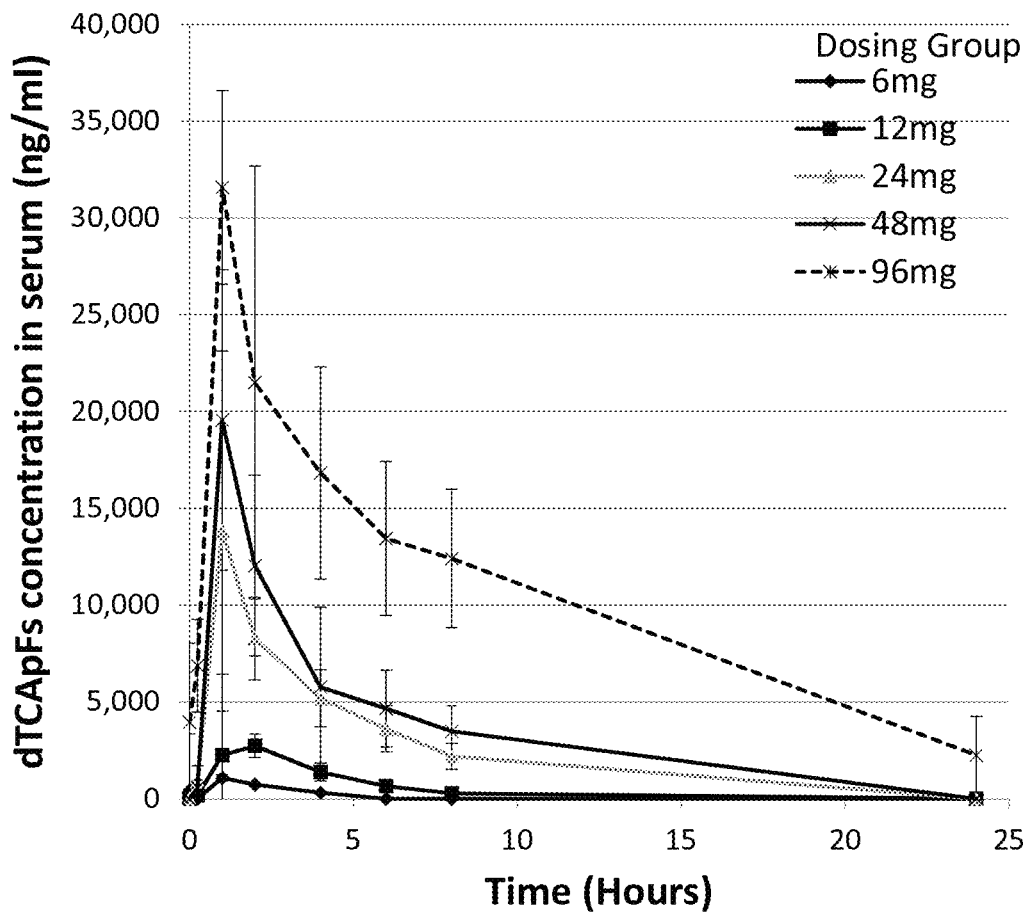
FIG. 7 is a graph showing the serum concentrations of dTCApFs over time by dose groups. Error bars represent SD.

PK results for the first day of cycles 1 and 2 are summarized in Table 2; $t_{1/2}$, Cmax and AUC0 were linearly related to dose. Dose-dependent plasma concentrations of dTCApFs were observed (FIG. 7).

Efficacy

Five of the 17 patients who were treated for ≥3 months (12, 24, and 48 mg/m²) experienced stable disease (SD) throughout the treatment period. Notably, one patient was suffering from lower back pain and weakness, apparently due to a spinal cord neoplasia pressing the spinal cord, received various pain-killers drugs (e.g., tramadol, oxycodone/naloxone, morphine, and pregabalin) and used a walker. After 6 months of treatments (12, 24, and 48 mg/m²) the patient improved her walk without the need of any pain-killer medication.

Figure 8:
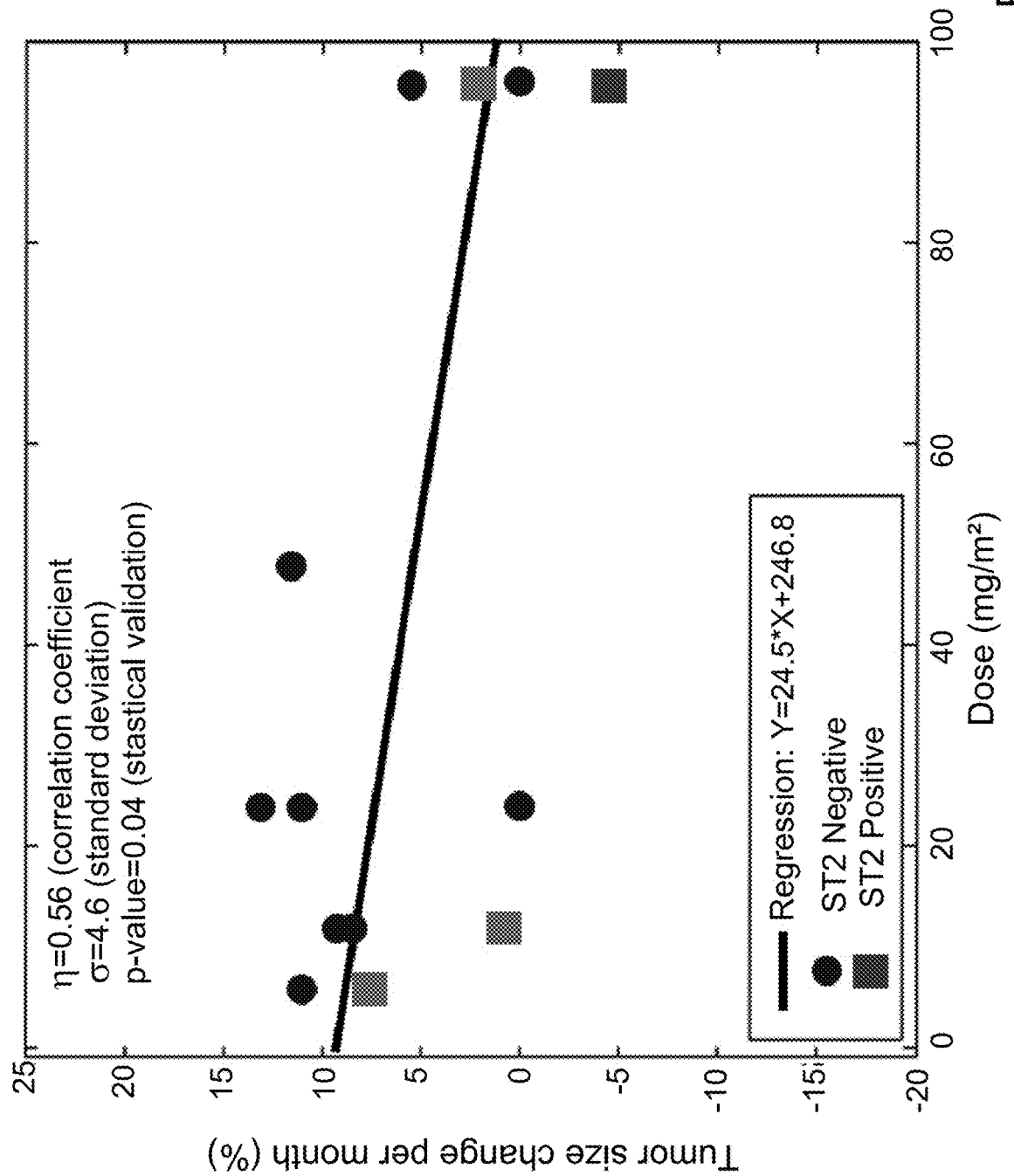
FIG. 8 is a graph showing correlation between changes in tumor size and the administered dose of dTCApFs.

Progression-free survival (PFS) analysis revealed that 6 patients experienced a longer PFS on dTCApFs compared to their prior regimen and one had PFS that was comparable to that on his prior regimen (these PFS values are indicated in Table 5 above in bold letters). In addition one patient who did not receive prior treatments was able to stay on the study drug for 330 days (stained positive) (Table 5). A regression analysis revealed a statistically significant correlation between changes in tumor size and the administered dTCApFs doses (FIG. 8).

Example 4

The Effect of the dTCApFs Peptide on ST2 Knock-Out Cells

As indicated above higher abundance of the ST2 receptor on ST2 positive cells may facilitate entry of the dTCApFs peptide into these cells. In order to further examine the effect of the presence of ST2 receptors on cancer cells on dTCApFs entry into cells, ST2 knock-out (KO) cells were prepared and the levels of various proteins in these cells in response to dTCApFs administration were examined, as detailed below.

Cells used for knock-out of the ST2 receptor were mammalian ovarian cells OV90 (adenocarcinoma). As detailed above, OV90 cells and KO OV90 cells were administered with dTCApFs and were then subjected to an Immunocytochemistry assay.

As evident by comparing FIG. 9A (control OV90 cells that were not administered with dTCApFs) to FIG. 9B (OV90 cells administered with dTCApFs), dTCApFs induced complete destruction of the Golgi apparatus, resulting in ER stress. FIG. 9B shows that the Golgi disappeared, and disrupted proteins accumulated on the ER, which is turn leads to ER stress. These results are based on analysis of the β-cop protein, which is one of the Golgi apparatus proteins.

In contrast to the above results, as demonstrated in FIG. 9C (control OV90 ST2 KO, not treated) and FIG. 9D (OV90 ST2 KO cells administered with the peptide) in OV90 ST2 KO cells, no effect of dTCApFs on the Golgi apparatus was observed (the arrows point to the intact Golgi apparatus).

FIG. 10 shows assessment of BiP expression in OV90 and in OV90 ST2 KO cells as a result of dTCApFs administration. While in OV90 cells a clear strengthening of the BiP stain is observed due to dTCApFs treatment as shown by comparison of FIG. 10A (without dTCApFs) to FIG. 10B (in the presence of dTCApFs), in OV90 ST2 KO cells there is no differences in the staining of BiP as a result of dTCApFs treatment, as deduced by comparing FIG. 10C and FIG. 10D. This means that OV90 ST2 KO cells did not respond to dTCApFs and no ER stress was thereby induced.

Without wishing to be bound by theory, the above results demonstrate how the ST2 receptor is related to ER stress in patients. Increased sensitivity of ST2 positive cells to dTCApFs and in turn the above results also explain the higher difference in expression levels of BiP observed in ST2 positive cells that are demonstrated in FIG. 6.

Example 5

The Effect of the dTCApFs Peptide on Normal Cells

The peptide dTCApFs was applied to healthy human peripheral immune cells and only minor cell death occurred, since apparently cancer cells are very sensitive to ER stress as opposed to normal healthy cells (data not shown). Therefore, without wishing to be bound by theory, dTCApFs appears to selectively affect cancer cells.

Example 6

The Level of the ER Marker CRT does not Correlate with the Administered Dose of the Nerofe Peptide Calreticulin (CRT) is a chaperone expressed under normal conditions in the ER of cells and assists in folding of newly synthesized proteins. Further to the results presented above which show an increase in the BiP ER stress marker as a result of treatment with dTCApFs, changes in CRT serum levels in human patients treated with dTCApFs were also examined. Dosing patients with different doses of dTCApFs (6 mg/mm$^2$-96 mg/mm$^2$) induced changes in CRT serum levels, however, without any correlation to the dose in which dTCApFs was administered, as opposed to BiP levels which showed linear correlation to dTCApFs administration and tumor size, as detailed above.

A bar graph showing the serum level of CRT at the end of the treatment by dTCApFs in cancer patients participating in the clinical study described above is shown in FIG. 11A and a bar graph showing the change in serum CRT levels in patients receiving dTCApFs treatment is shown in FIG. 11B.

In summary, no correlation was observed between the dose of dTCApFs and the level of serum CRT. In vitro experiments performed in mice showed that CRT levels in cells were not affected due to dTCApFs treatment, as opposed to BiP, the level of which increased as a result of treatment with dTCApFs (data not shown).

CRT is chaperone whose level is not increased in cells when treated with dTCApFs, while the level of BiP does increase in vitro and in vivo following treatment with dTCApFs. Although both are part of ER stress repair mechanism, dTCApFs selectively increases in-vitro and in-vivo of BiP and has no influence on CRT levels. The observation that no change in CRT level occurred correlates with change of serum levels of BiP and "no-change" of CRT. This mean that BiP change in level in patients correlates perfect with in vitro/in vivo activity of dTCApFs.

Example 7

The Peptide dTCApFs Activates NK Cells

Natural killer cells or "NK cells" are a type of cytotoxic lymphocyte critical to the innate immune system. The role of NK cells is analogous to that of cytotoxic T cells in the adaptive immune response. Among other functions, NK cells provide a rapid response to viral-infected cells and respond to tumor formation.

The effect of dTCApFs was also examined on human NK cells (CD56+CD16+, purchased from Lonza (2W-501)). NK cells were seeded on LGM-3 medium (supplemented with IL-2 and IL-15). The cells were treated with dTCApFs for 24 hours and further for 72 hours, followed by FACS analysis that focused on CD335 and CD337 antigens (Natural cytotoxicity triggering receptor 1 and Natural cytotoxicity triggering receptor 3, respectively). As shown in FIG. 12, an increase in expression of both receptors was induced by dTCApFs.

The CD335 and CD337 receptors are important for NK cells activity against cancer cells and virus infected cells. Induction of NK cells activity was also observed during the clinical trial described above for patient 006 (having a spinal cord neoplasm). During the clinical trial, biopsies of patients were stained with specific anti human NK cells antibodies before their entry to the clinical trial and after treatment was administered. A strong stain of NK cells in patients' biopsies after being administered with dTCApFs was observed (data not shown).

Example 8

Combining dTCApFs with Taxol Results in a Synergistic Effect

The beneficial therapeutic effect of the dTCApFs peptide on cancer cells prompted a further study, in which dTCApFs was administered to cancer cells in combination with an additional anti-cancer therapeutic agent, namely Taxol, under the conditions described above.

Taxol, also known as Paclitaxel, is an anti-cancer ("antineoplastic" or "cytotoxic") chemotherapeutic drug. Paclitaxel is classified as a "plant alkaloid," a "taxane" and an "antimicrotubule agent" used for the treatment of breast, ovarian, lung, bladder, prostate, melanoma, esophageal, as well as other types of solid tumor cancers.

The effect of the administered agents was monitored by a Bromodeoxyuridine (BrdU) incorporation assay, used for detecting active DNA synthesis and thereby cell proliferation and viability.

Figure 13A:
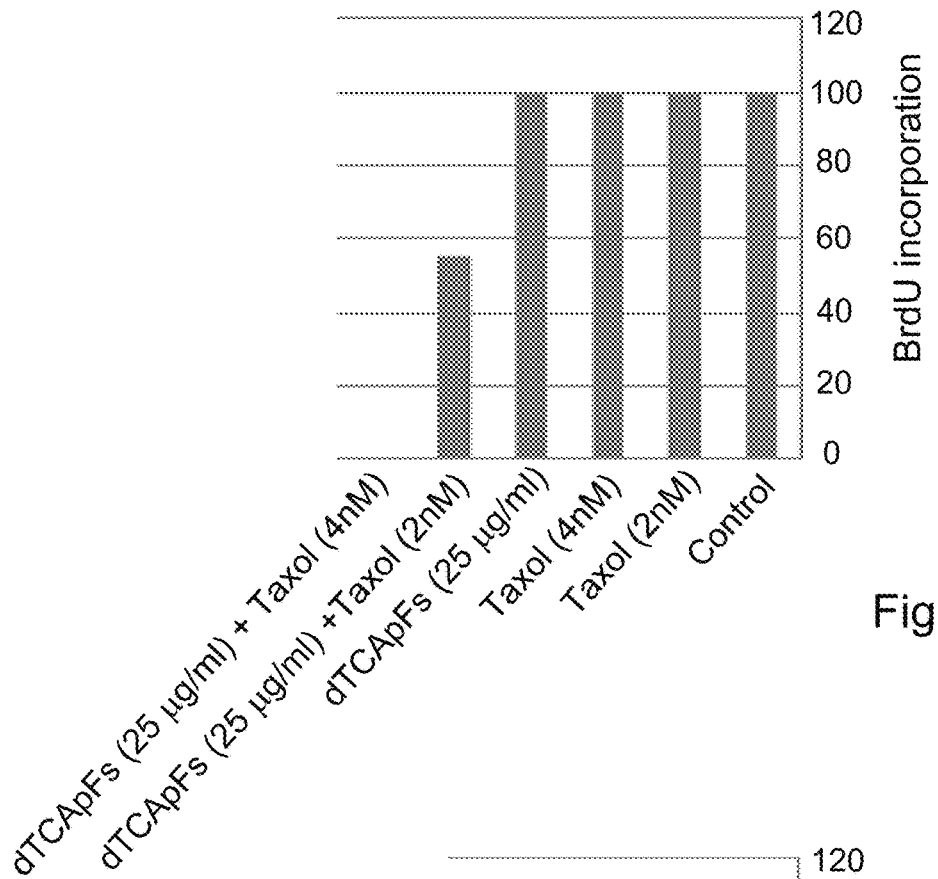
FIG. 13A-FIG. 13B are bar graphs showing the level of BrdU incorporation in human ovarian cancer cells (FIG. 13A) and human pancreatic cancer cells (FIG. 13B) in the presence of Taxol (2 nM or 4 nM), dTCApFs (25 µg/ml) or a combination thereof (dTCApFs at 25 µg/ml and Taxol at 2 or 4 nM).
Figure 13B:
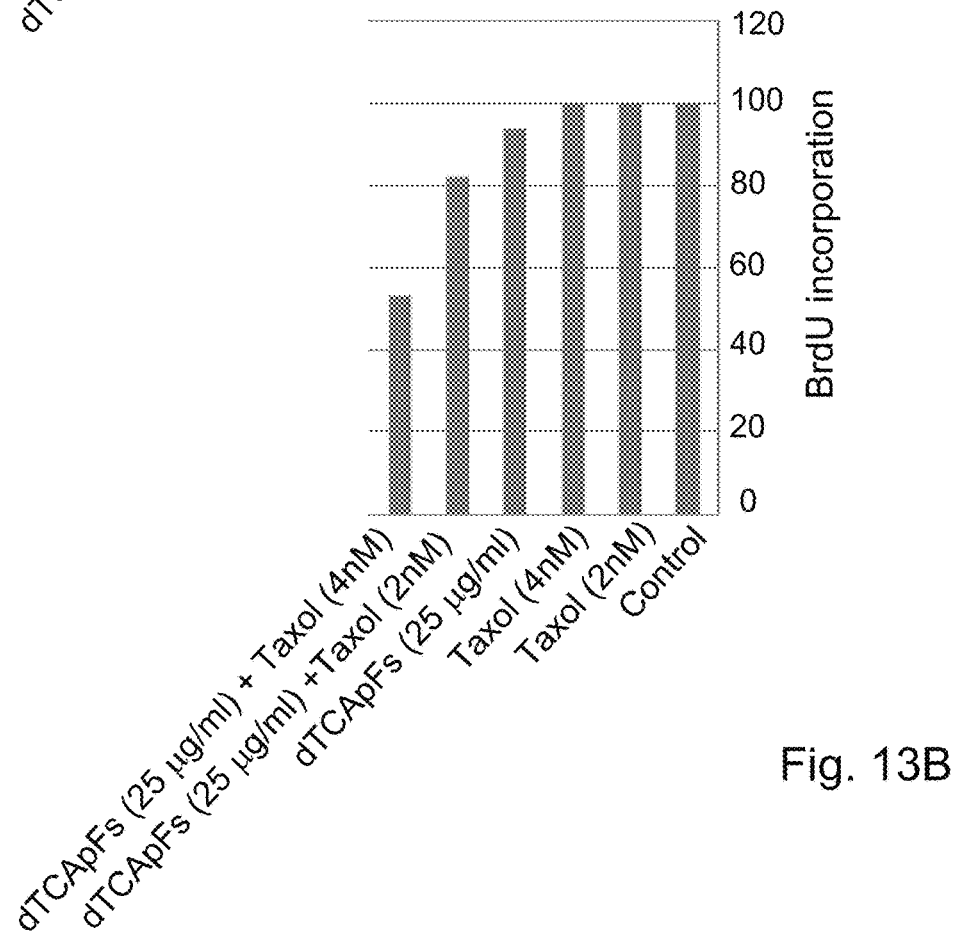

Two types of cancer cells were used for evaluating the combined effect of the dTCApFs peptide and Taxol, human ovarian cancer cells (OV90, FIG. 13A) and human pancreatic cancer cells (BxPC3, FIG. 13B).

When Taxol was administered alone to human ovarian cancer cells (FIG. 13A) or to human pancreatic cancer cells (FIG. 13B) no effect on cell viability was observed as compared to the control non-treated cells, based on the results of the BrdU incorporation assay performed.

In addition, as shown in Figure, 13A when the dTCApFs peptide (at 25 µg/ml) was administered alone to human ovarian cancer cells no effect on cell viability was observed as compared to the control non-treated cells.

However, when the dTCApFs peptide (at 25 µg/ml) was administered in combination with Taxol (at 2 nM) to human ovarian cancer cells, a decrease of approximately 50% in BrdU incorporation was observed (FIG. 13A). This effect was enhanced for a combination of dTCApFs (at 25 µg/ml) with Taxol at a concentration of 4 nM, for which no BrdU incorporation was observed.

Furthermore, as shown in Figure, 13B when the dTCApFs peptide (25 µg/ml) was administered alone to human pancreatic cancer cells, only a minor effect on cell viability was observed as compared to the control non-treated cells.

However, when dTCApFs (at 25 μg/ml) was administered in combination with Taxol (at 2 nM) to human ovarian cancer cells, a decrease of approximately 20% in BrdU incorporation was observed (FIG. 13B). This effect was more pronounced when a combination of dTCApFs at 25 μg/ml with Taxol at a concentration of 4 nM was used, reaching a reduction of over 40% in BrdU incorporation.

These results suggest a synergistic effect by the dTCApFs peptide on the activity of Taxol, which by itself did not have any effect on proliferation, thereby allowing a reduction of the dose of Taxol used in chemotherapy. Without wishing to be bound by theory this synergistic effect may be explained by the induction of ER stress by dTCApFs, as demonstrated above, which contributes to promoting cell death.

Example 9

The Effect of dTCApFs and Doxorubicin on Triple Negative Breast Cancer Tumors

Triple Negative Breast Cancer (TNBC) is defined by the lack of expression of estrogen receptor (ER) and progesterone receptor (PR) and the lack of expression or amplification of human epidermal growth factor receptor 2 (HER2). Treatment of TNBC is presently based on a number of agents that are approved for general breast cancer patients. However, in the absence of specific targets for treatment, TNBC is currently considered as an aggressive cancer subtype with limited treatment options and very poor prognosis following treatment with standard regimens.

The peptide dTCApFs was further assayed for treatment of TNBC as detailed below, in combination with doxorubicin (also termed Adriamycin, Caelyx, Myocet, etc.), which is a chemotherapy currently used for treatment of various cancer types, including breast cancer.

Therefore, 32 nude mice were inoculated subcutaneously (S.C.) with 9 million human TNBC cells (human MDA231, ATCC) per mouse. Cells were cultured as known in the art, for example, as described above. When the tumors exceeded a volume of 40 mm³, the mice were randomly divided into five groups, as follows. The "Control" group (n=5) was treated with 5% mannitol; the "dTCApFs" group (n=5) was treated once a week with dTCApFs at 15 mg/kg; the "Dox" group (n=5) was treated once a week with doxorubicin (Sigma Aldrich) at 3 mg/kg; the "dTCApFs+Dox next day" (n=8) group was treated with dTCApFs at 15 mg/kg and 24 hours later also with doxorubicin, at 3 mg/kg; and the "dTCApFs+Dox same day" (n=9) group was treated with dTCApFs at 15 mg/kg and with doxorubicin at 3 mg/kg, on same day.

Figure 14:
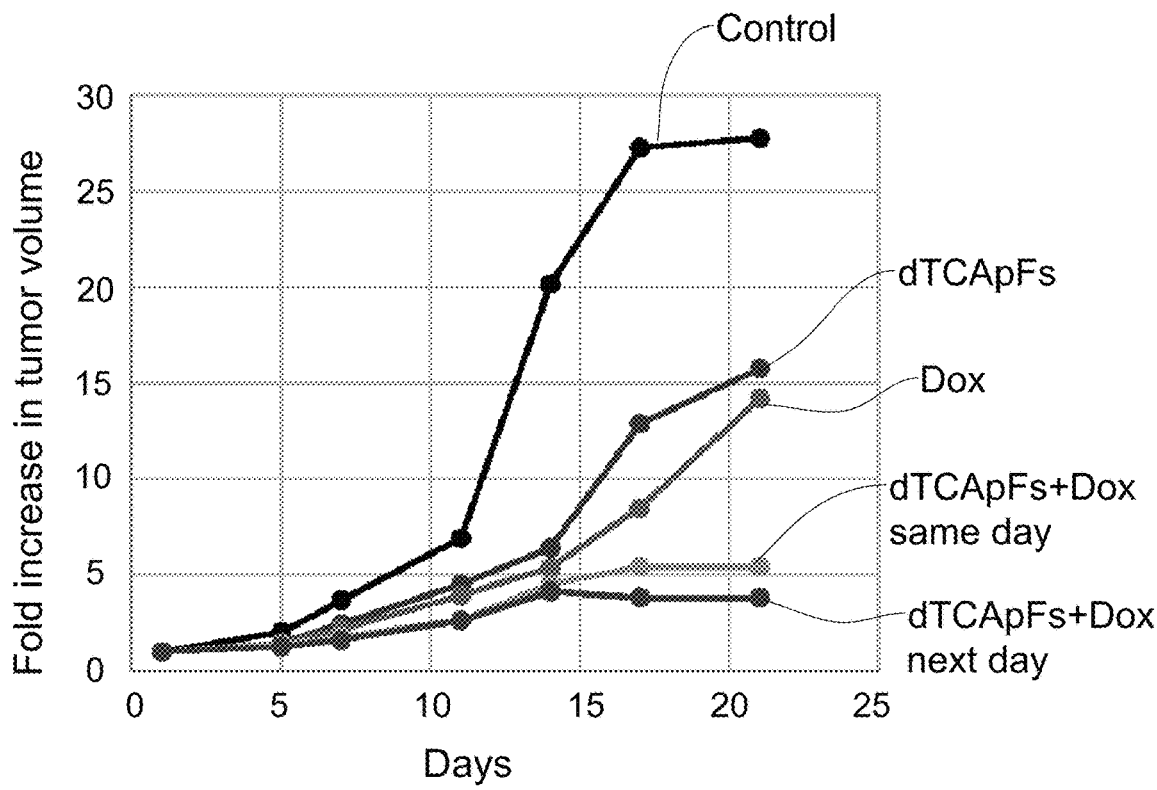
FIG. 14 is a graph showing the change in tumor volume during the indicated period of time, in mice inoculated with human triple negative breast cancer (hTNBC) cells and treated with dTCApFs (once a week, at 15 mg/kg), doxorubicin (once a week, at 3 mg/kg) or with a combination of dTCApFs and doxorubicin when doxorubicin and dTCApFs were administered on the same day or when doxorubicin was administered 24 hours after dTCApFs. "Control" represents treatment of mice with 5% mannitol. Abbreviations: Dox, doxorubicin; dTCApFs+Dox same day, a combination of dTCApFs and doxorubicin administered on the same day; dTCApFs+Dox next day, a combination of dTCApFs and doxorubicin where doxorubicin was administered 24 hours after administration of dTCApFs.

As shown in FIG. 14, the combination of dTCApFs and doxorubicin, resulted in substantial attenuation in tumor volume increase in mice, either when the mice were administered with the two agents on the same day or when mice were treated with dTCApFs and 24 hours later also with doxorubicin. These results are significant in view of the clear increase in tumor volume observed when the mice were treated with each one of the agents alone (at the same dosing), namely either with dTCApFs or with doxorubicin.

Figure 15:
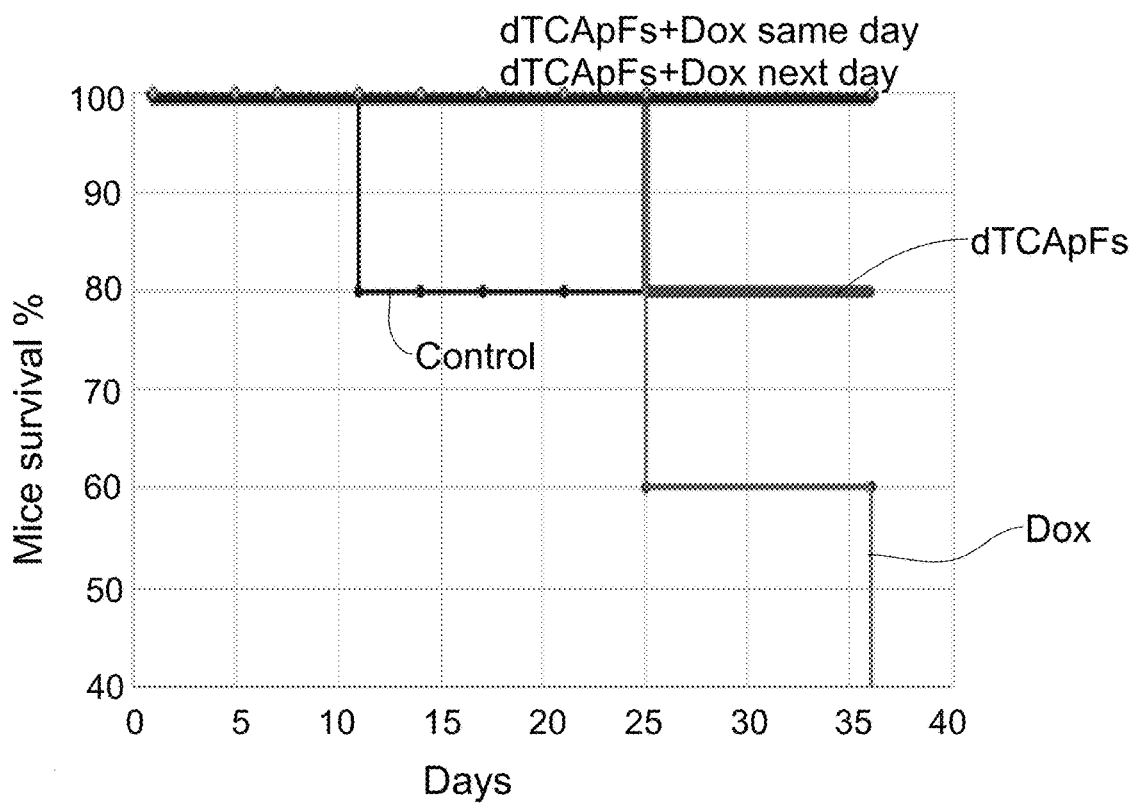
FIG. 15 is a graph showing survival rate of mice inoculated with hTNBC tumor and treated with Nerofe and doxorubicin during the indicated period of time. Mice were treated with dTCApFs (once a week at 15 mg/kg), doxorubicin (once a week at 3 mg/kg) or with a combination of dTCApFs and doxorubicin when doxorubicin was administered on the same day as dTCApFs or 24 hours after dTCApFs. "Control" represents treatment of mice with 5% mannitol. Abbreviations: Dox, doxorubicin; dTCApFs+Dox same day, a combination of dTCApFs and doxorubicin administered on the same day; dTCApFs+Dox next day, a combination of dTCApFs and doxorubicin where doxorubicin was administered 24 after administration of dTCApFs.

Furthermore, as evident from the survival curve in FIG. 15, mice treated with the combination of dTCApFs and doxorubicin exhibited 100% survival, either when the mice were administered with the two agents on the same day or when the mice were treated first with dTCApFs and 24 hours later also with doxorubicin.

Interestingly, in mice inoculated with MDA231 TNBC cells, which are positive for KRAS and treated with a combination of dTCApFs and doxorubicin, under the conditions specified above, KRAS expression was down-regulated, as evident from comparing FIG. 16B (mice inoculated with MDA231 cells and treated with a combination of dTCApFs and doxorubicin, in which almost no KRAS fluorescence is observed) to FIG. 16A (mice inoculated with MDA231 cells, control in which KRAS fluorescence is observed).

As known in the art, the gene KRAS has a central role in many cancer types, including pancreatic cancer and colon cancer, etc. Down-regulation of the gene product of KRAS by the combination as detailed above is indicative of the strong anti-cancer activity of the combination of the invention.

Example 10

The Effect of dTCApFs and Doxorubicin on Melanoma Tumors

Melanoma, also known as malignant melanoma, is a cancer type that develops from melanocytes, which are pigment-containing cells. Melanomas typically occur in the skin.

In order to examine the effect of a combination of dTCApFs and doxorubicin on melanoma tumor volume, the following experiments were performed in mice. C57bl/6 mice (28) were inoculated SC with 0.2 million B16 cells (ATCC) per mouse. B16 melanoma is a murine tumor cell line used for research as a model for human skin cancers. When tumors exceeded a volume of 50 mm³, the mice were randomly divided into 4 groups, as follows. "Control" group (n=6) was treated with 5% mannitol; "dTCApFs" treated group (n=6) was treated once a week with dTCApFs (at 15 mg/kg); "Dox" treated group (n=6) was treated once a week with doxorubicin (at 3 mg/kg); and dTCApFs+Dox same day" group (n=10) was treated once a week with dTCApFs and doxorubicin (at 15 mg/kg and 3 mg/kg, respectively), when both agents were administered on the same day.

As shown in FIG. 17, while tumor volume clearly increased in the presence of each one of the agents dTCApFs or doxorubicin at the doses indicated above, the combination of dTCApFs and doxorubicin resulted in substantial (and synergistic) attenuation in tumor volume increase in mice (without increasing the concentration of any one of the agents in the combination).

Example 11

The Effect of dTCApFs in Combination with an Anti PDL1 Antibody on Melanoma Tumors As known in the art, programmed death 1 (PD-1) protein, which is a T-cell co-inhibitory receptor, and one of its ligands (PD-L1), play a central role in the ability of tumor cells to evade the host's immune system. It has been previously shown that blocking the interactions between PD-1 and PD-L1 enhances immune function and mediates antitumor activity in vitro and in vivo. Therefore antibodies directed to PDL1 function as immune-stimulatory agents.

The effect of dTCApFs in combination with an anti-PD-L1 antibody was explored in a mice model for melanoma, as detailed below. C57Bl6 mice (14) were inoculated SC with 0.2 million B16 cells per mouse. When tumors exceeded a volume of 50 mm³, mice were divided randomly into 3 groups, as follows: the "Control" group (n=5) was treated with 5% mannitol; the "anti PDL1 antibody" group (n=4) was treated with an anti-PDL1 antibody (BXcell) twice a week (at 20 mg/kg); and the "anti-PDL1 antibody+dTCApFs" group (n=5) was treated with dTCApFs and an anti-PDL1 antibody, where dTCApFs was administered three times per week, at 1 mg/kg and the anti-PDL1 antibody was administered twice a week, at 20 mg/kg. The terms "anti-PD-L1 antibody" and "anti-PD-L1 antibodies" are used interchangeably.

In other words, the combination of the anti-PDL1 antibodies and the peptide dTCApFs was administered to mice twice a week on the same day, at doses of 20 and 1 mg/kg for the anti-PDL1 antibodies and dTCApFs, respectively, and the weekly regimen also included an additional dose of the peptide dTCApFs, at 1 mg/kg.

Figure 18:
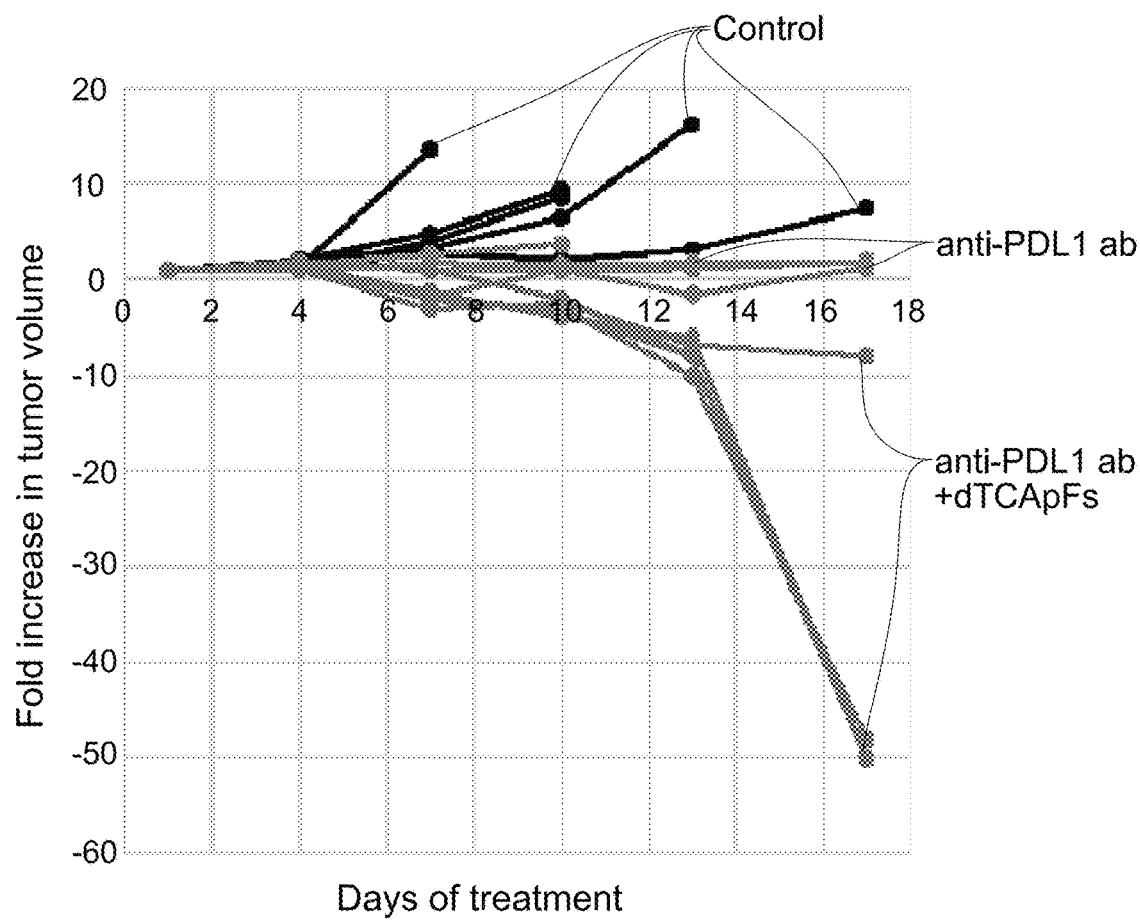
FIG. 18 is a graph showing the change in tumor size during the indicated period of time, in mice inoculated with B16 cells (melanoma tumors) and treated with anti-PDL1 antibodies (twice a week, at 20 mg/kg) alone or in combination with dTCApFs (three times a week, at 1 mg/kg). "Control" represents treatment of mice with 5% mannitol. Abbreviations: anti-PDL1 ab, anti-PDL1 antibodies; anti-PDL1 ab+dTCApFs, anti-PDL1 antibodies in combination with dTCApFs.

As evident from FIG. 18, when mice were treated with an anti-PDL1 antibody per se, there was no significant change in tumor size. However, when the anti-PDL1 antibody was combined with dTCApFs, tumor size significantly decreased (without increasing the concentration of the administered anti-PDL1 antibody).

Figure 19A:
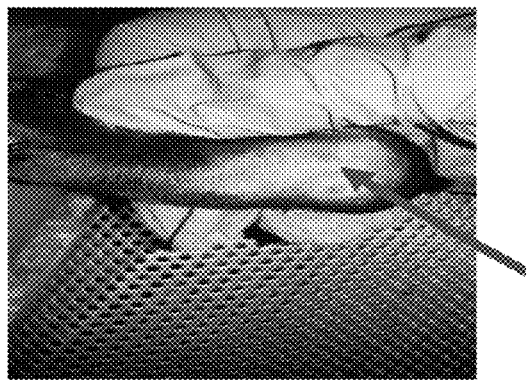
FIG. 19A-FIG. 19B are photographs of a mice inoculated with a melanoma tumor and treated with an a nti-PDL1 antibody in the presence of dTCApFs (FIG. 19A) or in its absence (FIG. 19B). Tumor area is indicated by an arrow.
Figure 19B:
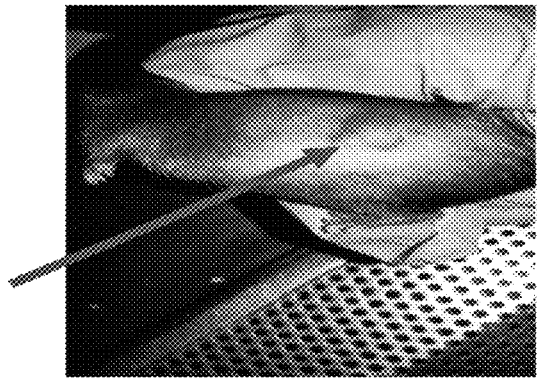

The significant effect of the above combination on tumor size is also demonstrated by comparing FIG. 19A, showing a mouse having a melanoma tumor that was treated with the combination of dTCApFs and an anti-PDL1 antibody under the conditions specified above, to FIG. 19B, showing a mouse having a melanoma tumor that was treated only with the anti-PDL1 antibody. As evident from FIG. 19, the tumor volume was significantly decreased in the presence of the above combination therapy.

Example 12

The Effect of dTCApFs in Combination with an Anti PDL1 Antibody on the Presence of Immune System Cells in the Tumor Micro Environment The effect of administering dTCApFs in combination with anti PDL1 antibodies on cells of the immune system was examined as follows.

B16F10 tumor cells were injected S.C. (200,000 cells/mice) to female C57BL/6 mice (JOlaHsd, 4 weeks old). When tumors reached the size of 0.4-0.5 cm treatment started by administering the mice intraperitoneally (i.p.) with anti-PDL1 antibodies (in vivoMAb anti-mouse PD-L1 (B7-H1) clone 10F.9G2 Lot 615416D1 BioCell USA) on Sundays and Thursdays and with dTCApFs (diluted in 5% mannitol) on Sundays, Mondays and Thursdays. Treatment groups were as follows: Control (treated with 5% mannitol), a group treated with 20 mg/kg anti-PDL1 antibodies and 0.1 mg/kg dTCApFs, a group treated with 20 mg/kg anti-PDL1 antibodies and 0.5 mg/kg dTCApFs and a group treated with 20 mg/kg anti-PDL1 antibodies and 1 mg/kg dTCApFs. All of the groups were treated for 19 days.

Post treatment, the tumors were collected in 4% Formalin and after 24 hours moved to 70% ethanol and then slides were prepared for immunohistochemistry (IHC), according to cell's signaling protocol. Antigen retrieval was with Citrate at pH 6. The first antibody used for natural killer cells detection was anti-NK (MA1-70100 thermo, 1:100 diluted) and the secondary antibody used was an anti-mouse IgG (H+L), F(ab')2 Fragment (Alexa Fluor® 488 Conjugate, #4408 1:1000 diluted). The first antibody used for CD8 cells detection was anti-CD8 (ab203035 abcam, 1:100 diluted) and the secondary antibody used was anti-rabbit IgG (H+L), F(ab')2 Fragment (Alexa Fluor® 488 Conjugate, #4412 1:1000 diluted).

Figure 20A:
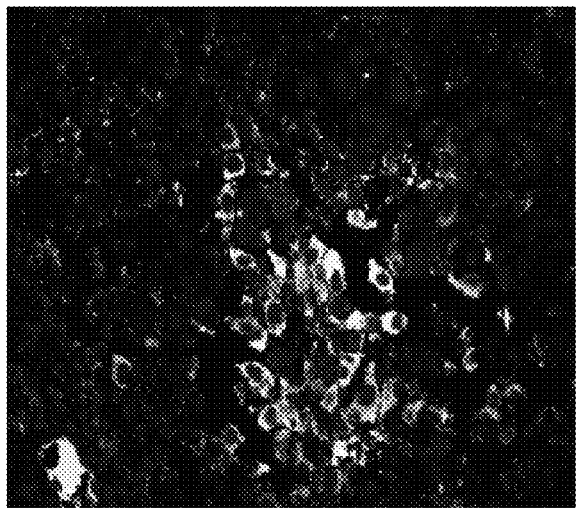
FIG. 20A-FIG. 20D are fluorescence micrographs showing the presence of NK cells and CD8 cells in tumor sections treated with a combination of anti-PDL1 antibodies and dTCApFs (FIG. 20A and FIG. 20B, respectively) or with dTCApFs alone (FIG. 20C and FIG. 20D, respectively).

FIG. 20A is an exemplary micrograph showing the level of NK cells in tumor sections of mice treated with the combination of dTCApFs with anti-PDL1 antibodies. As evident by comparing FIG. 20A to FIG. 20C (which is a micrograph showing the level of NK cells in tumor sections of mice treated only with dTCApFs), the level of NK cells increased as a result of the above combination treatment.

Figure 20B:
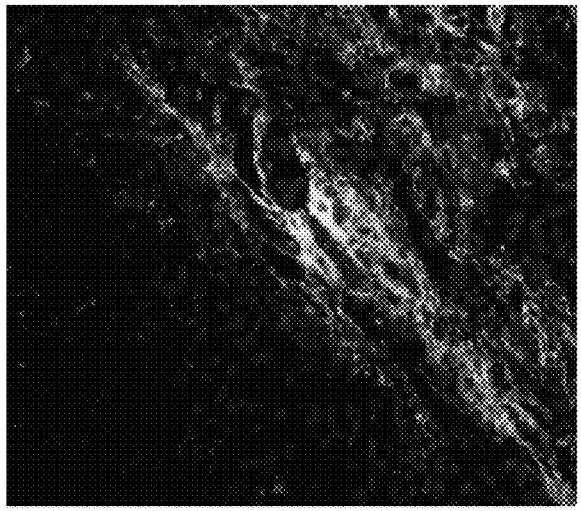
Figure 20C:
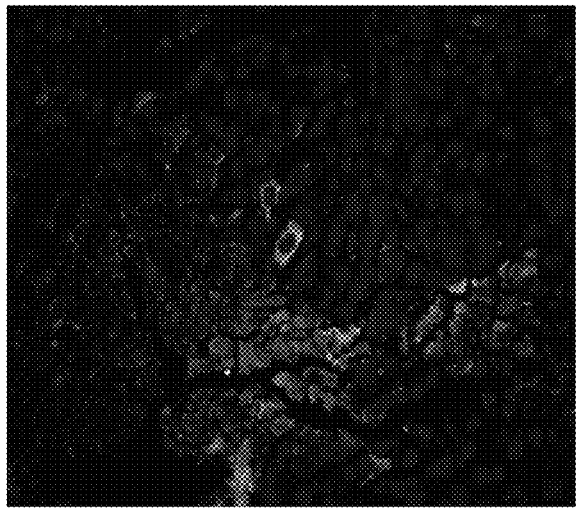
Figure 20D:
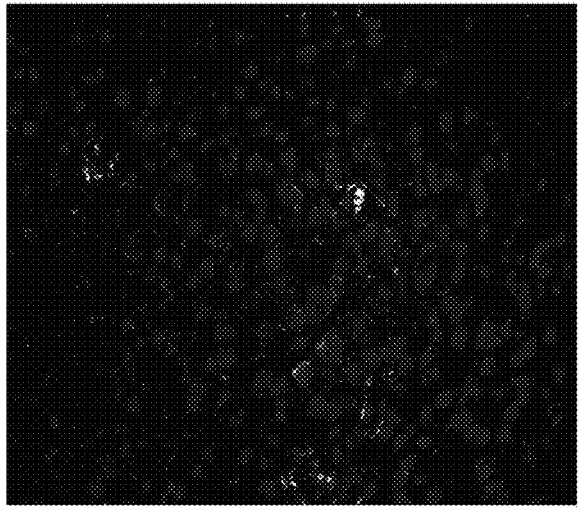

Furthermore, FIG. 20B is an exemplary micrograph showing the level of CD8 cells in tumor sections of mice treated with the combination of dTCApFs with anti-PDL1 antibodies. As evident by comparing FIG. 20B to FIG. 20D (which is a micrograph showing the level of CD8 cells in tumor sections of mice treated only with dTCApFs), the level of CD8 cells also increased as a result of the above combination treatment.

Taken together the above results indicate that the combination of the peptide dTCApFs with the anti-PDL1 antibody can increase the presence of anticancer immune cells in the tumor. These cells can strongly induce death of cancer cells in the tumor.

Example 13

The Effect of dTCApFs in Combination with an Anti PDL1 Antibody on Pancreatic Cancer Tumors The effect of dTCApFs in combination with an anti-PD-L1 antibody was further examined in mice inoculated with cells originating from a pancreatic tumor, as detailed below. C57Bl6 mice (32) were inoculated SC with 0.2 million Panc02 cells per mouse (ATCC). When tumor size exceeded a volume of 50 mm$^3$, the mice were randomly divided into 3 groups, as follows: the "Control" group (n=8) was treated with 5% mannitol, the "anti-PDL1 antibody" group (n=8) was treated with an anti-PDL1 antibody twice a week (at 20 mg/kg); the "dTCApFs" group (n=8) was treated three times per week with dTCApFs at 1 mg/kg; and the "anti-PDL1 antibody+dTCApFs" group (n=8) was treated with dTCApFs three times per week at 1 mg/kg and with the anti-PDL1 antibody twice per week at 20 mg/kg.

As indicated above, the combination of the anti-PDL1 antibodies and the peptide dTCApFs was administered to mice twice a week on the same day, at doses of 20 and 1 mg/kg for the anti-PDL1 antibodies and dTCApFs, respectively, and the weekly regimen also included an additional dose of the peptide dTCApFs, at 1 mg/kg.

Figure 21:
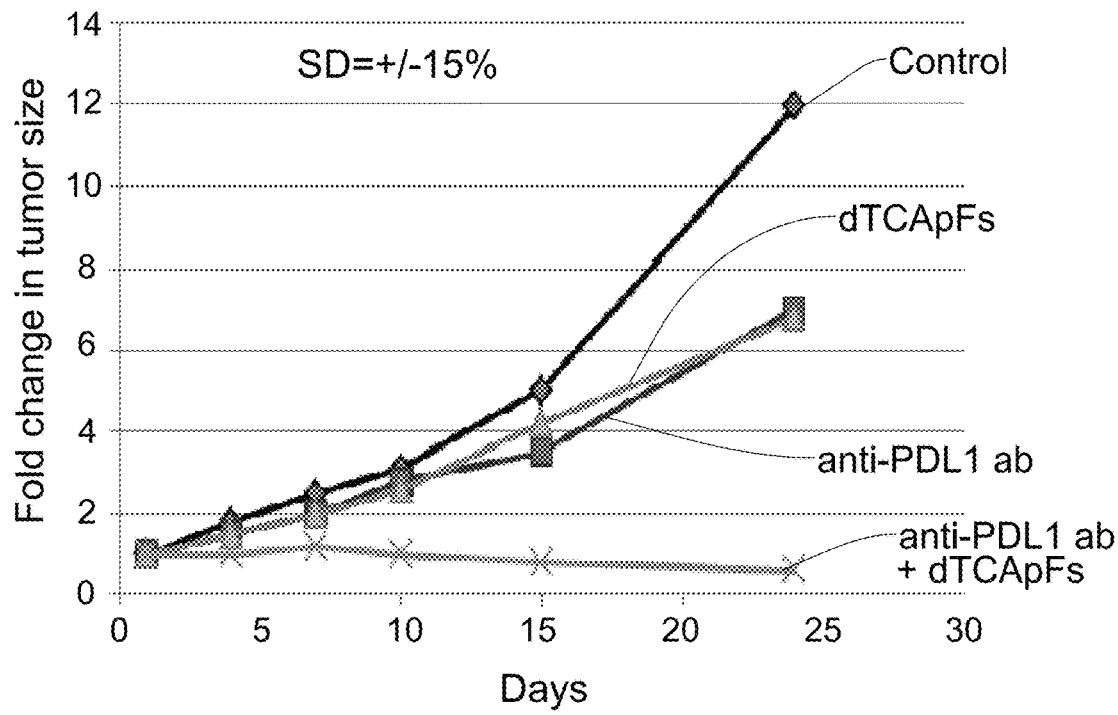
FIG. 21 is a graph showing the change in tumor size during the indicated period of time, in mice inoculated with Panc02 cells and treated with dTCApFs (three times per week, at 1 mg/kg), anti-PDL1 antibodies (twice a week at 20 mg/kg) or with a combination of dTCApFs and anti-PDL1 antibodies, when dTCApFs was administered three times per week at 1 mg/kg and the anti-PDL1 antibodies were administered twice per week, at 20 mg/kg. "Control" represents treatment of mice with 5% mannitol. Abbreviations: anti-PDL1 ab, anti-PDL1 antibodies; anti-PDL1 ab+dTCApFs, anti-PDL1 antibodies in combination with dTCApFs.

As shown in FIG. 21, while in the control group and in the groups treated with either dTCApFs or the anti-PDL1 antibody tumor size increased in a time-dependent manner, when dTCApFs and the anti-PDL1 antibody were administered together (as a combination), there was a slight decrease in tumor size over time, reflecting a synergistic effect between the two agents.

Example 14

The Effect of dTCApFs in Combination with an Anti PDL1 Antibody on Breast Cancer Tumors The effect of dTCApFs in combination with an anti-PD-L1 antibody was further examined in a mouse model of a breast cancer tumor, namely EMT6 cells, as detailed below. To that end, Balb/c mice (32) were inoculated S.C. with 0.8 million EMT6 cells (ATCC) per mouse. When the tumors exceeded a volume of 50 mm$^3$, the mice were randomly divided into 3 groups, as follows: the "control" group (n=8) was treated with 5% mannitol; the "anti-PDL1 antibody" group (n=8) was treated twice a week at 20 mg/kg; the "dTCApFs" group (n=8) was treated three times per week at 1 mg/kg; and the "anti-PDL1 antibody+dTCApFs" group (n=8) was treated with dTCApFs three times per week at 1 mg/kg and with an anti-PDL1 antibody twice a week at 20 mg/kg.

As indicated above, the combination of the anti-PDL1 antibodies and the peptide dTCApFs was administered to mice twice a week on the same day, at doses of 20 and 1 mg/kg for the anti-PDL1 antibodies and dTCApFs, respectively, and the weekly regimen also included an additional dose of the peptide dTCApFs, at 1 mg/kg.

Figure 22:
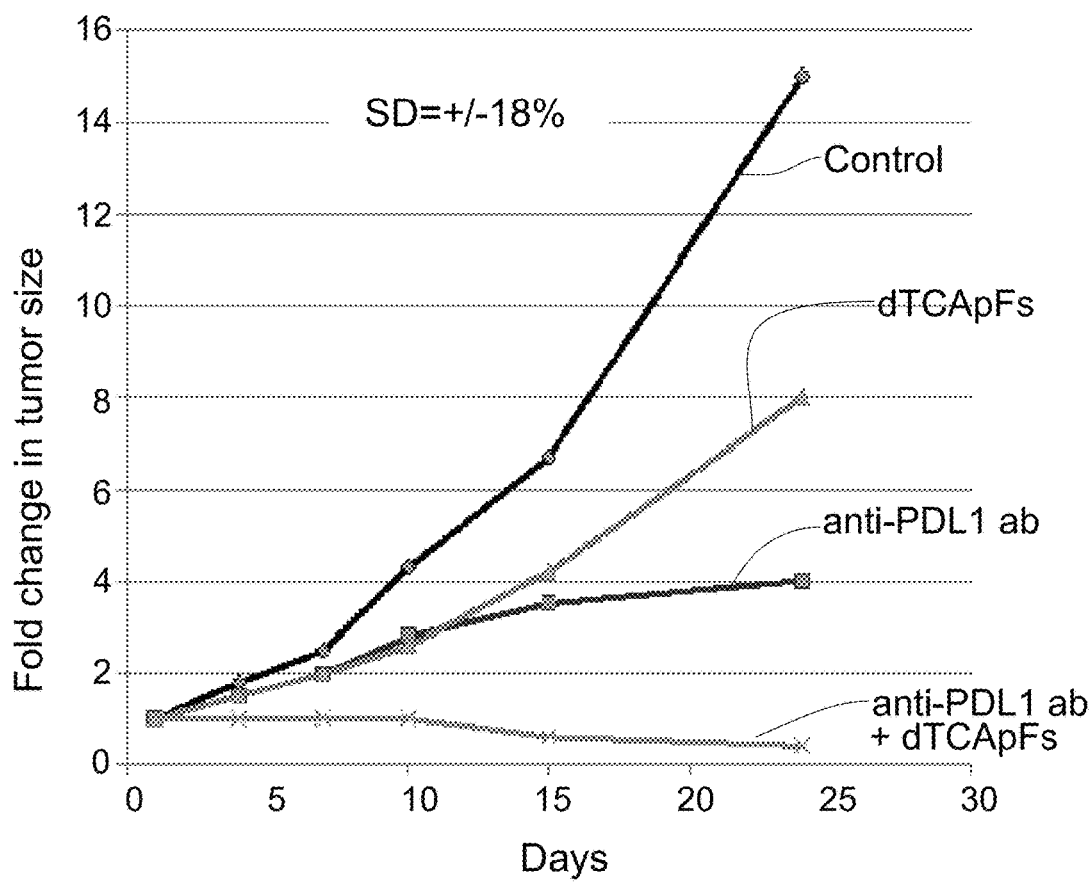
FIG. 22 is a graph showing the change in tumor size during the indicated period of time, in mice inoculated with EMT6 cells and treated with dTCApFs (three times per week, at 1 mg/kg), anti-PDL1 antibodies (twice a week at 20 mg/kg) or with a combination of dTCApFs and anti-PDL1 antibodies, when dTCApFs was administered three times per week at 1 mg/kg and the anti-PDL1 antibodies were administered twice per week, at 20 mg/kg. "Control" represents treatment of mice with 5% mannitol. Abbreviations: anti-PDL1 ab, anti-PDL1 antibodies; anti-PDL1 ab+dTCApFs, anti-PDL1 antibodies in combination with dTCApFs.

As shown in FIG. 22, while in the control group the tumor size rapidly increased in a time-dependent manner, the increase in tumor size was moderate in the groups treated with either dTCApFs or the anti-PDL1 antibody, when administered as a monotherapy.

However, when dTCApFs and the anti-PDL1 antibody were administered together (as a combination), there was a slight decrease in tumor size over time, as observed above for the pancreatic cancer cells. Apparently, dTCApFs and the anti-PDL1 antibody had a synergistic effect in attenuating tumor growth.

Taken together, the above results show that the patient may benefit from the combination treatment described herein, since for a dose of an anti-cancer agent that appears ineffective as a monotherapy, a synergistic beneficial effect is demonstrated when combined with dTCApFs. Lowering the dose of an anti-cancer agent may postpone drug resistance mechanisms, reduce the toxicity associated with the anti-cancer drug, etc.

Without wishing to be bound by theory, dTCApFs induces ER stress rendering the cells more sensitive to low doses of the anti-cancer agents, e.g. doxorubicin, taxol and the anti-PDL1 antibodies, due to induced expression of the protein CHOP. Once cells express CHOP they become very sensitive to low doses of e.g. doxorubicin. More than that, dTCApFs activates the innate immune response and in combination with the induced ER stress in cancer cells it increases cells' sensitivity to anticancer agents.

The invention claimed is:

1. A method of treatment of cancer in a patient in need thereof, comprising administering to said patient a therapeutically effective amount of an isolated peptide comprising the amino acid sequence denoted by SEQ ID NO. 1 or a pharmaceutically acceptable salt of said isolated peptide in combination with doxorubicin, wherein said isolated peptide reduces the standard of care administered dose of doxorubicin.

2. The method according to claim 1, wherein the administered dose of doxorubicin is lower than the standard of care dose of doxorubicin by at least about 1%-50%, about 5%-45%, about 10%-40%, about 15%-35% or about 20%-30%.

3. The method according to claim 1, wherein said isolated peptide and doxorubicin are administered concomitantly or consecutively.

4. The method according to claim 1, wherein said cancer is pancreatic cancer, ovarian cancer, spindle cell neoplasm of neural origin, spindle cell neoplasm, metastatic colorectal cancer, colon cancer, colorectal cancer, colon adenocarcinoma, rectal cancer, rectal adenocarcinoma, lung cancer, non-small cell lung carcinoma, spinal cord neoplasm, breast cancer, skin cancer, renal cancer, multiple myeloma, thyroid cancer, prostate cancer, adenocarcinoma, head and neck cancer, gastrointestinal cancer, stomach cancer, cancer of the small intestine, hepatic carcinoma, liver cancer or malignancies of the female genital tract.

5. The method according to claim 1, wherein said isolated peptide consists of the amino acid sequence denoted by SEQ ID NO. 1 or a pharmaceutically acceptable salt thereof.

6. The method according to claim 1, wherein said isolated peptide or a pharmaceutically acceptable salt thereof is administered at a dose of about 5 mg/m$^2$ to about 100 mg/m$^2$.

7. The method according to claim 1, wherein said isolated peptide or a pharmaceutically acceptable salt thereof is administered at a frequency of once, twice or thrice per week.

8. The method according to claim 1, wherein said method further comprises administering at least one additional anti-cancer agent.

* * * * *